(12) United States Patent
Faham et al.

(10) Patent No.: US 9,228,232 B2
(45) Date of Patent: *Jan. 5, 2016

(54) METHODS OF MONITORING CONDITIONS BY SEQUENCE ANALYSIS

(71) Applicant: Sequenta, Inc., South San Francisco, CA (US)

(72) Inventors: Malek Faham, Pacifica, CA (US); Thomas Willis, San Francisco, CA (US)

(73) Assignee: Sequenta, LLC., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/329,873

(22) Filed: Jul. 11, 2014

(65) Prior Publication Data

US 2014/0342367 A1    Nov. 20, 2014

Related U.S. Application Data

(63) Continuation of application No. 13/459,701, filed on Apr. 30, 2012, which is a continuation of application No. 12/615,263, filed on Nov. 9, 2009, now Pat. No. 8,236,503.

(60) Provisional application No. 61/112,693, filed on Nov. 7, 2008.

(51) Int. Cl.
  *C12Q 1/68* (2006.01)
  *C12N 15/10* (2006.01)

(52) U.S. Cl.
  CPC .......... *C12Q 1/6869* (2013.01); *C12N 15/1072* (2013.01); *C12Q 1/6827* (2013.01); *C12Q 1/6881* (2013.01); *C12Q 1/6883* (2013.01); *C12Q 1/6886* (2013.01); *C12Q 2600/118* (2013.01)

(58) Field of Classification Search
  USPC .............................................. 435/6.12, 91.2
  See application file for complete search history.

(56) References Cited

U.S. PATENT DOCUMENTS

| 5,296,351 | A | 3/1994 | Morley |
|---|---|---|---|
| 5,298,396 | A | 3/1994 | Kotzin et al. |
| 5,336,598 | A | 8/1994 | Kotzin et al. |
| 5,418,134 | A | 5/1995 | Morley |
| 5,627,052 | A | 5/1997 | Schrader |
| 5,635,354 | A | 6/1997 | Kourilsky et al. |
| 5,698,396 | A | 12/1997 | Pfreundschuh |
| 5,776,708 | A | 7/1998 | Kotzin et al. |
| 5,837,447 | A | 11/1998 | Gorski |
| 6,087,096 | A | 7/2000 | Dau et al. |
| 6,090,592 | A | 7/2000 | Adams et al. |
| 6,143,496 | A | 11/2000 | Brown et al. |
| 6,258,568 | B1 | 7/2001 | Nyren |
| 6,416,948 | B1 | 7/2002 | Pilarski et al. |
| 6,440,706 | B1 | 8/2002 | Vogelstein et al. |
| 6,524,829 | B1 | 2/2003 | Seeger |
| 6,596,492 | B2 | 7/2003 | Avery et al. |
| 6,667,159 | B1 | 12/2003 | Walt |
| 6,919,434 | B1 | 7/2005 | Goto et al. |
| 6,964,850 | B2 | 11/2005 | Bevilacqua |
| 7,148,040 | B2 | 12/2006 | Meagher et al. |
| 7,306,906 | B2 | 12/2007 | Maruyama et al. |
| 7,375,211 | B2 | 5/2008 | Kou |
| 7,691,994 | B2 | 4/2010 | Brewer et al. |
| 7,741,463 | B2 | 6/2010 | Gormley et al. |
| 7,749,697 | B2 | 7/2010 | Oleksiewicz et al. |
| 7,785,783 | B2 | 8/2010 | Morley et al. |
| 7,915,015 | B2 | 3/2011 | Vogelstein et al. |
| 8,236,503 | B2 | 8/2012 | Faham et al. |
| 8,283,294 | B2 | 10/2012 | Kastrup et al. |
| 8,507,205 | B2 | 8/2013 | Faham et al. |
| 8,628,927 | B2 | 1/2014 | Faham et al. |
| 8,691,510 | B2 | 4/2014 | Faham et al. |
| 8,748,103 | B2 | 6/2014 | Faham et al. |
| 8,795,970 | B2 | 8/2014 | Faham et al. |
| 9,043,160 | B1 | 5/2015 | Moorhead et al. |
| 2002/0076725 | A1 | 6/2002 | Toyosaki-Maeda et al. |
| 2002/0110807 | A1 | 8/2002 | Pilarski et al. |
| 2003/0096277 | A1 | 5/2003 | Chen |
| 2003/0120061 | A1 | 6/2003 | Zhang |
| 2003/0162197 | A1 | 8/2003 | Morley et al. |
| 2004/0132050 | A1 | 7/2004 | Monforte |
| 2004/0248172 | A1 | 12/2004 | Samoszuk et al. |
| 2005/0064421 | A1 | 3/2005 | Gehrmann et al. |

(Continued)

FOREIGN PATENT DOCUMENTS

| CN | 101225441 A | 7/2008 |
|---|---|---|
| EP | 1544308 A1 | 6/2005 |

(Continued)

OTHER PUBLICATIONS

Stranten et al. Journal of Translational Medicine, 2004, vol. 2(11), p. 1-10.*
U.S. Appl. No. 61/045,586, Filed Apr. 16, 2008, Han et al.
PCT/US2014/017416, Appln filed Feb. 20, 2014, Pepin et al.
U.S. Appl. No. 12/945,678, filed Nov. 12, 2010, Faham et al.
U.S. Appl. No. 13/174,086, filed Jun. 30, 2011, Faham et al.
U.S. Appl. No. 13/369,031, filed Feb. 8, 2012, Faham et al.
U.S. Appl. No. 13/627,497, filed Sep. 26, 2012, Faham et al.
U.S. Appl. No. 14/075,075, filed Nov. 8, 2013, Faham et al.
U.S. Appl. No. 14/173,712, filed Feb. 5, 2014, Faham et al.
U.S. Appl. No. 14/176,551, filed Feb. 10, 2014, Faham et al.
U.S. Appl. No. 14/185,846, filed Feb. 20, 2014, Pepin et al.
U.S. Appl. No. 14/197,615, filed Mar. 5, 2014, Carlton et al.
U.S. Appl. No. 14/202,990, filed Mar. 10, 2014, Zheng.
U.S. Appl. No. 14/242,520, filed Apr. 1, 2014, Klinger et al.
U.S. Appl. No. 14/343,286, filed Mar. 6, 2014, Faham et al.
U.S. Appl. No. 14/350,516, filed Apr. 8, 2014, Faham et al.

(Continued)

Primary Examiner — Kenneth R. Horlick
Assistant Examiner — Joyce Tung
(74) Attorney, Agent, or Firm — Cooley LLP

(57) ABSTRACT

There is a need for improved methods for determining the diagnosis and prognosis of patients with conditions, including autoimmune disease and cancer. Provided herein are methods for using DNA sequencing to identify personalized biomarkers in patients with autoimmune disease and other conditions. Identified biomarkers can be used to determine the disease state for a subject with an autoimmune disease or other condition.

23 Claims, 27 Drawing Sheets

(56) References Cited

U.S. PATENT DOCUMENTS

| | | |
|---|---|---|
| 2005/0255482 A1 | 11/2005 | Morley et al. |
| 2006/0046258 A1 | 3/2006 | Lapidus et al. |
| 2006/0085139 A1 | 4/2006 | Collette et al. |
| 2006/0088876 A1 | 4/2006 | Bauer |
| 2006/0134125 A1 | 6/2006 | Luxembourg et al. |
| 2006/0147925 A1 | 7/2006 | Morley et al. |
| 2006/0228350 A1 | 10/2006 | Wu et al. |
| 2006/0233812 A1 | 10/2006 | Burnie et al. |
| 2006/0234234 A1 | 10/2006 | Van Dongen et al. |
| 2006/0259248 A1 | 11/2006 | Collette et al. |
| 2007/0020670 A1 | 1/2007 | Loken et al. |
| 2007/0105105 A1 | 5/2007 | Clelland et al. |
| 2007/0117134 A1 | 5/2007 | Kou |
| 2007/0160994 A1 | 7/2007 | Lim et al. |
| 2007/0161001 A1 | 7/2007 | Leshkowitz |
| 2007/0238099 A1 | 10/2007 | Cohen et al. |
| 2007/0243564 A1 | 10/2007 | Lawson et al. |
| 2007/0286849 A1 | 12/2007 | Chaturvedi |
| 2008/0050780 A1 | 2/2008 | Lee et al. |
| 2008/0069770 A1 | 3/2008 | Hercend et al. |
| 2008/0108509 A1 | 5/2008 | Haupl et al. |
| 2008/0166704 A1 | 7/2008 | Marche et al. |
| 2008/0166718 A1 | 7/2008 | Lim et al. |
| 2008/0248484 A1 | 10/2008 | Bauer |
| 2008/0274904 A1 | 11/2008 | Gormley et al. |
| 2008/0280774 A1 | 11/2008 | Burczynski |
| 2008/0286777 A1 | 11/2008 | Candeias et al. |
| 2009/0026082 A1* | 1/2009 | Rothberg et al. ............ 204/556 |
| 2009/0053184 A1 | 2/2009 | Morgan et al. |
| 2009/0181859 A1 | 7/2009 | Muraguchi |
| 2009/0197257 A1 | 8/2009 | Harris |
| 2009/0226975 A1 | 9/2009 | Sabot et al. |
| 2009/0253581 A1 | 10/2009 | Van Eijk et al. |
| 2009/0280489 A1 | 11/2009 | Devinder et al. |
| 2009/0298060 A1 | 12/2009 | Lal et al. |
| 2010/0021896 A1 | 1/2010 | Han |
| 2010/0021984 A1 | 1/2010 | Edd |
| 2010/0027896 A1 | 2/2010 | Geva et al. |
| 2010/0035764 A1 | 2/2010 | Chen |
| 2010/0040606 A1 | 2/2010 | Lantto et al. |
| 2010/0042329 A1 | 2/2010 | Hood et al. |
| 2010/0151471 A1 | 6/2010 | Faham et al. |
| 2010/0159456 A1 | 6/2010 | Albitar |
| 2010/0167353 A1 | 7/2010 | Walder et al. |
| 2010/0173394 A1 | 7/2010 | Colston, Jr. |
| 2010/0255471 A1 | 10/2010 | Clarke |
| 2010/0285975 A1 | 11/2010 | Mathies |
| 2010/0330571 A1 | 12/2010 | Robins et al. |
| 2011/0003291 A1 | 1/2011 | Pasqual |
| 2011/0129830 A1 | 6/2011 | Ladner et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2012/0058902 A1 | 3/2012 | Livingston et al. |
| 2012/0135409 A1 | 5/2012 | Faham et al. |
| 2012/0220466 A1 | 8/2012 | Fire et al. |
| 2013/0005584 A1 | 1/2013 | Faham et al. |
| 2013/0017957 A1 | 1/2013 | Faham et al. |
| 2013/0065768 A1 | 3/2013 | Zheng et al. |
| 2013/0136799 A1 | 5/2013 | Faham et al. |
| 2013/0150252 A1 | 6/2013 | Faham et al. |
| 2013/0196328 A1 | 8/2013 | Pepin et al. |
| 2013/0202718 A1 | 8/2013 | Pepin et al. |
| 2013/0236895 A1 | 9/2013 | Faham et al. |
| 2013/0253842 A1 | 9/2013 | Sherwood et al. |
| 2013/0267427 A1 | 10/2013 | Faham et al. |
| 2013/0288237 A1 | 10/2013 | Robins et al. |
| 2013/0302801 A1 | 11/2013 | Asbury et al. |
| 2013/0324422 A1 | 12/2013 | Faham et al. |
| 2013/0344066 A1 | 12/2013 | Faham et al. |
| 2014/0057799 A1 | 2/2014 | Johnson et al. |
| 2014/0127699 A1 | 5/2014 | Han |
| 2014/0155277 A1 | 6/2014 | Wiley |
| 2014/0186848 A1 | 7/2014 | Robins et al. |
| 2014/0194295 A1 | 7/2014 | Robins et al. |
| 2014/0206548 A1 | 7/2014 | Robins et al. |
| 2014/0206549 A1 | 7/2014 | Robins et al. |
| 2014/0213463 A1* | 7/2014 | Robins et al. ............ 506/2 |
| 2014/0221220 A1 | 8/2014 | Robins et al. |
| 2014/0234835 A1 | 8/2014 | Pepin et al. |
| 2014/0235454 A1 | 8/2014 | Faham et al. |
| 2014/0255929 A1 | 9/2014 | Zheng |
| 2014/0255944 A1 | 9/2014 | Carlton et al. |
| 2014/0256567 A1 | 9/2014 | Robins et al. |
| 2014/0256592 A1 | 9/2014 | Faham et al. |
| 2014/0315725 A1 | 10/2014 | Faham et al. |
| 2014/0322716 A1 | 10/2014 | Robins |
| 2014/0336059 A1 | 11/2014 | Faham et al. |
| 2014/0342360 A1 | 11/2014 | Faham et al. |
| 2014/0349883 A1 | 11/2014 | Faham |
| 2014/0356339 A1 | 12/2014 | Faham et al. |
| 2015/0031043 A1 | 1/2015 | Faham et al. |
| 2015/0031553 A1 | 1/2015 | Faham et al. |
| 2015/0038346 A1 | 2/2015 | Faham |
| 2015/0065352 A1 | 3/2015 | Faham et al. |

FOREIGN PATENT DOCUMENTS

| | | |
|---|---|---|
| EP | 1549764 B1 | 7/2005 |
| EP | 2062982 A1 | 5/2009 |
| EP | 2088432 A1 | 8/2009 |
| EP | 2364368 B1 | 1/2014 |
| JP | 2005-245381 A | 9/2005 |
| JP | 2007-536939 A | 12/2007 |
| JP | 2008099588 A | 5/2008 |
| WO | WO 93/01838 A1 | 2/1993 |
| WO | WO 2005/059176 A1 | 6/1995 |
| WO | WO 95/28481 A1 | 10/1995 |
| WO | WO 97/13877 A1 | 4/1997 |
| WO | WO 97/18330 A1 | 5/1997 |
| WO | WO 97/46706 A1 | 12/1997 |
| WO | WO 98/01738 A1 | 1/1998 |
| WO | WO 03/044225 A2 | 5/2003 |
| WO | WO 03/059155 A2 | 7/2003 |
| WO | WO 03/044225 A3 | 12/2003 |
| WO | WO 2004/003820 A2 | 1/2004 |
| WO | WO 03/059155 A3 | 3/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/046098 A3 | 8/2004 |
| WO | WO 2004/096985 A2 | 11/2004 |
| WO | WO 2005/005651 A2 | 1/2005 |
| WO | WO 2005/042774 A2 | 5/2005 |
| WO | WO 2005/053603 A2 | 6/2005 |
| WO | WO 2005/084134 A2 | 9/2005 |
| WO | WO 2006/076205 A2 | 7/2006 |
| WO | WO 2006/110855 A2 | 10/2006 |
| WO | WO 2006/116155 A2 | 11/2006 |
| WO | WO 2006/138284 A2 | 12/2006 |
| WO | WO 2008/026927 A2 | 3/2008 |
| WO | WO 2008/026927 A3 | 4/2008 |
| WO | WO 2008/039694 A2 | 4/2008 |
| WO | WO 2008/108803 A2 | 9/2008 |
| WO | WO 2008/108803 A3 | 12/2008 |
| WO | WO 2008/147879 A1 | 12/2008 |
| WO | WO 2009/015296 A1 | 1/2009 |
| WO | WO 2009/019657 A2 | 2/2009 |
| WO | WO 2009/021215 A1 | 2/2009 |
| WO | WO 2006/076205 A3 | 4/2009 |
| WO | WO 2009/045898 A2 | 4/2009 |
| WO | WO 2009/070767 A2 | 6/2009 |
| WO | WO 2009/019657 A3 | 8/2009 |
| WO | WO 2009/095567 A2 | 8/2009 |
| WO | WO 2009/108860 A2 | 9/2009 |
| WO | WO 2009/108866 A2 | 9/2009 |
| WO | WO 2009/070767 A3 | 10/2009 |
| WO | WO 2009/108866 A3 | 10/2009 |
| WO | WO 2009/137255 A2 | 11/2009 |
| WO | WO 2009/137832 A2 | 11/2009 |
| WO | WO 2009/145925 A1 | 12/2009 |
| WO | WO 2009/151628 A2 | 12/2009 |

(56) References Cited

FOREIGN PATENT DOCUMENTS

| WO | WO 2009/158521 A2 | 12/2009 |
|---|---|---|
| WO | WO 2009/108860 A3 | 1/2010 |
| WO | WO 2009/137255 A3 | 1/2010 |
| WO | WO 2010/011894 A1 | 1/2010 |
| WO | WO 2009/151628 A3 | 2/2010 |
| WO | WO 2010/036352 A1 | 4/2010 |
| WO | WO 2009/158521 A3 | 5/2010 |
| WO | WO 2010/053587 A2 | 5/2010 |
| WO | WO 2010/151416 A1 | 12/2010 |
| WO | WO 2011/083296 A1 | 7/2011 |
| WO | WO 2011/106738 A2 | 9/2011 |
| WO | WO 2011/139371 A1 | 11/2011 |
| WO | WO 2011/139372 A1 | 11/2011 |
| WO | WO 2011/140433 A2 | 11/2011 |
| WO | WO 2011/106738 A3 | 12/2011 |
| WO | WO 2012/027503 A2 | 3/2012 |
| WO | WO 2012/048340 A2 | 4/2012 |
| WO | WO 2012/048340 A3 | 6/2012 |
| WO | WO 2012/083069 A2 | 6/2012 |
| WO | WO 2012/083225 A2 | 6/2012 |
| WO | WO 2013/036459 A2 | 3/2013 |
| WO | WO 2013/055595 A1 | 4/2013 |
| WO | WO 2013/059725 A1 | 4/2013 |
| WO | WO 2013/066726 A1 | 5/2013 |
| WO | WO 2013/085855 A1 | 6/2013 |
| WO | WO 2013/086450 A1 | 6/2013 |
| WO | WO 2013/086462 A1 | 6/2013 |
| WO | WO 2013/090390 A2 | 6/2013 |
| WO | WO 2013/090469 A1 | 6/2013 |
| WO | WO 2013/096480 A2 | 6/2013 |
| WO | WO 2013/134162 A2 | 9/2013 |
| WO | WO 2013/134302 A1 | 9/2013 |
| WO | WO 2013/155119 A1 | 10/2013 |
| WO | WO 2013/158936 A1 | 10/2013 |
| WO | WO 2013/181428 A2 | 12/2013 |
| WO | WO 2013/188471 A2 | 12/2013 |
| WO | WO 2014/018460 A1 | 1/2014 |
| WO | WO 2014/026031 A1 | 2/2014 |
| WO | WO 2014/062945 A1 | 4/2014 |
| WO | WO 2014/062959 A1 | 4/2014 |
| WO | WO 2014/066184 A1 | 5/2014 |
| WO | WO 2014/130685 A1 | 8/2014 |
| WO | WO 2015/002908 A1 | 1/2015 |
| WO | WO 2015/013461 A2 | 1/2015 |

OTHER PUBLICATIONS

U.S. Appl. No. 14/350,785, filed Apr. 9, 2014, Faham et al.

Alatrakchi, et al. T-cell clonal in patients with B-cell lymphoproliferative disorders. J Immunother. Sep. 1998;21(5):363-70.

Andreasson, et al. The human IgE-encoding transcriptome to assess antibody repertoires and repertoire evolution. J Mol Biol. Sep. 15, 2006;362(2):212-27. Epub Aug. 14, 2006.

Arstila et al., "A direct estimate of the human αβ T cell receptor diversity," Science 286:958-961 (1999).

Bagnara, et al. IgV gene intraclonal diversification and clonal evolution in B-cell chronic lymphocytic leukaemia. Br J Haematol. Apr. 2006;133(1):50-8.

Batzoglou. The many faces of sequence alignment. Briefings in Bioinformatics. 2005; 6:6-22.

Beishuizen, et al. Analysis of Ig and T-cell receptor genes in 40 childhood acute lymphoblastic leukemias at diagnosis and subsequent relapse: implications for the detection of minimal residual disease by polymerase chain reaction analysis. Blood. Apr. 15, 1994;83(8):2238-47.

Bene, et al. How and why minimal residual disease studies are necessary in leukemia: a review from WP10 and WP12 of the European LeukaemiaNet. Haematologica. Aug. 2009;94(8):1135-50. Epub Jul. 7, 2009.

Benichou, et al. Rep-Seq: uncovering the immunological repertoire through next-generation sequencing. Immunology. Mar. 2012;135(3):183-91. doi: 10.1111/j.1365-2567.2011.03527.x.

Bonarius, et al. Monitoring the T-Cell Receptor Repertoire at Single-Clone Resolution. PLoS One. Dec. 20, 2006;1:e55.

Boria, et al. Primer sets for cloning the human repertoire of T cell receptor variable regions. BMC Immunology. 2008; 9:50.

Boyd et al. Measurement and clinical monitoring of human lymphocyte clonality by massively parallel VDJ pyrosequencing. Sci Transl. Med. 1(12):12ra23 (2009).

Boyd, et al. Individual variation in the germline Ig gene repertoire inferred from variable region gene rearrangements. J Immunol Jun. 15, 2010;184(12):6986-92. Epub May 21, 2010.

Brehm-Stecher, et al. Single-cell microbiology: tools, technologies, and applications. Microbiology and molecular biology reviews. 2004; 68(3):538-559.

Brisco, et al. Determining the repertoire of IGH gene rearrangements to develop molecular markers for minimal residual disease in B-lineage acute lymphoblastic leukemia. J Mol Diagn. May 2009;11(3):194-200. Epub Mar. 26, 2009.

Bruggemann, et al. Clinical significance of minimal residual disease quantification in adult patients with standard-risk acute lymphoblastic leukemia. Blood. Feb. 1, 2006;107(3):1116-23. Epub Sep. 29, 2005.

Bruggemann, et al. Standardized MRD quantification in European ALL trials: proceedings of the Second International Symposium on MRD assessment in Kiel, Germany, Sep. 18-20, 2008. Leukemia. Mar. 2010;24(3):521-35. doi: 10.1038/leu.2009.268. Epub Dec. 24, 2009.

Campana. Minimal residual disease in acute lymphoblastic leukemia. Semin Hematol. Jan. 2009;46(1):100-6.

Campbell et al., "Subclonal phylogenetic structures in cancer revealed by ultra-deep sequencing," PNAS 105(35):13081-13086 (2008).

Chen, A novel approach for the analysis of T-cell reconstitution by using a T-cell receptor beta-based oligonucleotide microarray in hematopoietic stem cell transplantation. Exp Hematol. May 2007;35(5):831-41.

Choi, et al. Clonal evolution in B-lineage acute lymphoblastic leukemia by contemporaneous VH-VH gene replacements and VH-DJH gene rearrangements. Blood. Mar. 15, 1996;87(6):2506-12.

Choi, et al. Relapse in children with acute lymphoblastic leukemia involving selection of a preexisting drug-resistant subclone. Blood. Jul. 15, 2007;110(2):632-9. Epub Mar. 19, 2007.

The International Search Report for PCT Application PCT/US2009/006053 dated Jun. 15, 2010.

Costabile, et al. Molecular approaches in the diagnosis of primary immunodeficiency diseases. Hum Mutat. Dec. 2006;27(12):1163-73.

Cronn, et al. Multiplex sequencing of plant chloroplast genomes using Solexa sequencing-by-synthesis technology. Nucleic Acids Res. Nov. 2008;36(19):e122.

Curran et al., "Nucleotide sequencing of psoriatic arthritis tissue before and during methotrexate administration reveals a complex inflammatory T cell infiltrate with very few clones exhibiting features that suggest they drive the inflammatory process by recognizing autoantigens," J Immunol 172:1935-1944 (2004).

Currier, et al. Spectratype/immunoscope analysis of the expressed TCR repertoire. Current Protocols in Immunology. 2000; Supplement 38:10.28.1-10.28.24.

Davi, et al. Lymphocytic progenitor cell origin and clonal evolution of human B-lineage acute lymphoblastic leukemia. Blood. Jul. 15, 1996;88(2):609-21.

Davis, et al. Staining of cell surface human CD4 with 2-F-pyrimidine-containing RNA amptamers for flow cytometry. Nucleic Acids Research. 1998; 26(17):3915-3924.

Deng et al., "Gene profiling involved in immature CD4+ T lymphocyte responsible for systemic lupus erythematosus," Molecular Immunology 43:1497-1507 (2006).

Dohm, et al. Substantial biases in ultra-short read data sets from high throughput DNA sequencing. Nucleic Acids Research. 2008; 36:e105.

Dou, et al. Analysis of T cell receptor Vbeta gene usage during the course of disease in patients with chronic hepatitis B. J Biomed Sci. Nov.-Dec. 1998;5(6):428-34.

(56) References Cited

OTHER PUBLICATIONS

Du et al., "TCR spectratyping revealed T lymphocytes associated with graft-versushost disease after allogeneic hematopoietic stem cell transplantation," Leukemia & Lymphoma 48(8):1618-1627 (2007).
Edd, et al. Controlled encapsulation of single cells into monodisperse picoliter drops. Lap Chip. 2008; 8(8):1262-1264.
European office action dated Mar. 28, 2012 for EP Application No. 09764927.1.
European search report and opinion dated Mar. 13, 2014 for EP Application No. 13195379.6.
European search report and opinion dated Jul. 26, 2013 for EP Application No. 11777704.5.
Ewing et al, "Base-calling of automated sequencer traces using Phred. I. Accuracy Assessment," Genome Research, 8: 175-185 (1998).
Freeman et al., "Profiling the T-cell receptor beta-chain repertoire by massively parallel sequencing," Genome Res. 19(10):1817-1824 (2009).
Fritz et al., "Alterations in the spinal cord T cell repertoire during relapsing experimental autoimmune encephalomyelitis," J Immunol 164:6662-6668 (2000).
Garcia-Castello, et al. Detection of clonal immunoglobulin and T-cell receptor gene recombination in hematological malignancies: monitoring minimal residual disease. Cardiovascular & Haematological Disorders-Drug Targets. 2009; 9:124-135.
Gerlinger, et al. How Darwinian models inform therapeutic failure initiated by clonal heterogeneity in cancer medicine. Br J Cancer. Oct. 12, 2010;103(8):1139-43. doi: 10.1038/sj.bjc.6605912. Epub Sep. 28, 2010.
Germano, et al. Clonality profile in relapsed precursor-B-All children by GeneScan and sequencing analyses. Consequences on minimal residual disease monitoring. Leukemia. Aug. 2003;17(8):1573-82.
Giuggio, et al. Evolution of the intrahepatic T cell repertoire during chronic hepataitis C virus infection. Viral Immunol. 2005;18(1):179-89.
Golembowski, et al. Clonal evolution in a primary cutaneous follicle center B cell lymphoma revealed by single cell analysis in sequential biopsies. Immunobiology. Apr. 2000;201(5):631-44.
Gonzalez, et al. Incomplete DJH rearrangements as a novel tumar target for minimal residual disease quantitation in multiple myeloma using real-time PCR. Leukemia. 2003; 17:1051-1057.
Gonzalez, et al. Incomplete DJH rearrangements of the IgH gene are frequent in multiple myelioma patients: immunobioligcal characteristics and clinical applications. Leukemia. 2003; 17:1398-1403.
Gorski, et al. Circulating T cell repertoire complexity in normal individuals and bone marrow recipients analyzed by CDR3 size spectratyping. Correlation with immune status. J Immunol May 15, 1994;152(10):5109-19.
Green, et al. Clonal diversity of Ig and T-cell-receptor gene rearrangements identifies a subset of childhood B-precursor acute lymphoblastic leukemia with increased risk of relapse. Blood. Aug. 1, 1998;92(3):952-8.
Greenberg, et al. Profile of immunoglobulin heavy chain variable gene repertoires and highly selective detection of malignant clonotypes in acute lymphoblastic leukemia. J Leukoc Biol. Jun. 1995;57(6):856-64.
Guo, et al. Sequence changes at the V-D junction of the VH1 heavy chain of anti-phosphocholine antibodies alter binding to and protection against *Streptococcus pneumoniae*. Int Immunol May 1997;9(5):665-77.
Gurrieri, et al. Chronic lymphocytic leukemia B cells can undergo somatic hypermutation and intraclonal immunoglobulin V(H)DJ(H) gene diversification. J Exp Med. Sep. 2, 2002;196(5):629-39.
Han, et al. Immunorepertoire analysis by multiplex PCR amplification and high throughput sequencing . Abstract. The 96 Annual Meeting of The American Association of Immunologists, Seattle, Washington, May 8-12, 2009. Available at http://jimmunol.org//cgi/content/meeting_abstract/182/1_MeetingAbstracts/42.6?sid=25 7929f1-97a9-4330-8e96-1750aa240e69. Accessed Nov. 24, 2010.

Heger, M. Studies Highlight Challenges of Immune Repertoire Sequencing's Clinical Applicability. Available at http://www.genomeweb.com/sequencing/studies-highlight-challenges-immune-repertoire-sequencings-clinical-applicabilit?hq_e=el&hq_m=966798&hq_1=10&hq_v=2357e2f0b3. Accessed Apr. 6, 2011.
Holt, "Q &A: BC cancer agency's Robert Holt on sequencing the immune repertoire in immune reconstitution," Genome Web (www.genomeweb.com) Jun. 30, 2009.
Howe, et al. T cell receptor clonotype analysis of T cell responses: Diagnostic application of a clonotypic database. Blood. 2003; 102:Abstract 3918.
Illumina. Data Sheet: Sequencing. Genomic Sequencing. Pub. No. 770.2008-016 Copyright 2010. Reference states: "Current as of Jan. 30, 2009.".
International preliminary report on patentability dated May 19, 2011 for PCT/US2009/006053.
International search report and written opinion dated Sep. 22, 2011 for PCT Application No. US11/000791.
International search report and written opinion dated Oct. 19, 2011 for PCT Application No. US11/000792.
Ishii et al., "Isolation and expression profiling of genes upregulated in the peripheral blood cells of systemic lupus erythematosus patients," DNA Research 12:429-439 (2005).
Jacobi et al., "Activated memory B cell subsets correlate with disease activity in systemic lupus erythematosus: delineation by expression of CD27, IgD, and CD95," Arthritis & Rheumatism 58(6):1762-1773 (2008).
Jacobi et al., "Correlation between circulating CD27high plasma cells and disease activity in patients with systemic lupus erythematosus," Arthritis & Rheumatism 48(5):1332-1342 (2003).
Jena, et al. Amplification of genes, single transcripts and cDNA libraries from one cell and direct sequence analysis of amplified products derived from one molecule. J. Immunol. Methods. 1996; 190:199-213.
Kato et al., "Analysis of accumulated T cell clonotypes in patients with systemic lupus erythematosus," Arthritis & Rheumatism 43(12):2712-2721 (2000).
Kim, et al An efficient and reliable DNA extraction method for preimplantation genetic diagnosis: a comparison of allele drop out and amplification rates using different single cell iysis methods. Fertility and Sterility. 2009; 92: 814-818.
Kim, et al. Polony multiplex analysis of gene expression (PMAGE) in mouse hypertrophic cardiomyopathy. Science. Jun. 8, 2007;316(5830):1481-4.
Kita, et al. T cell receptor clonotypes in skin lesions from patients with systemic lupus erythematosus. J Invest Dermatol. Jan. 1998;110(1):41-6.
Kneba, et al. Analysis of rearranged T-cell receptor beta-chain genes by polymerase chain reaction (PCR() DNA sequencing and automated high resolution PCR fragment analysis. Blood. 1995; 86:3930-3937.
Kobari, et al. T cells accumulating in the inflamed joints of a spontaneous murine model of rheumatoid arthritis become restricted to common clonotypes during disease progression. Int Immunol. Jan. 2004;16(1):131-8.
Kou, et al. T-Cell receptor Vbeta repertoire CDR3 length diversity differs within CD45RA and CD45RO T-cell subsets in healthy and human immunodeficiency virus-infected children. Clin Diagn Lab Immunol. Nov. 2000;7(6):953-9.
Langerak, et al. Immunoglobulin/T-cell receptor clonality diagnostics. Exoert Opin. Med. Diagn. 2007; 1(3):451-461.
Langerak, et al. Polymerase chain reaction-based clonality testing in tissue samples with reactive lymphoproliferations: usefulness and pitfalls. A report of the Biomed-2 Concerted Action BMH4-CT98-3936. Leukemia. Feb. 2007;21(2):222-9. Epub Dec. 14, 2006.
Laplaud et al., "Blood T-cell receptor 13 chain transcriptome in multiple sclerosis. Characterization of the T cells with altered CDR3 length distribution," Brain 127:981-995 (2004).
Laplaud et al., "Serial blood T cell repertoire alterations in multiple sclerosis patients; correlation with clinical and MRI parameters," J Neroimmunol 177:151-160 (2006).

(56) References Cited

OTHER PUBLICATIONS

Li, et al. An improved one-tube RT-PCR protocol for analyzing single-cell gene expression in individual mammalian cells. Anal. Bioanal. Chem. 2010; 397: 1853-1859.
Li, et al. Clonal rearrangements in childhood and adult precursor B acute lymphoblastic leukemia: a comparative polymerase chain reaction study using multiple sets of primers. Eur J Haematol. Oct. 1999;63(4):211-8.
Li, et al. Detailed clonality analysis of relapsing precursor B acute lymphoblastic leukemia: implications for minimal residual disease detection. Leukemia Research. 2001; 25:1033-1045.
Li, et al. Sequence analysisn of clonal immunoglobulin and T-cell receptor gene rearrangements in children with acute lymphoblastic leukemia at diagnosis and at relapse: implications for pathogenesis and for the clinical utility of PCR-based methods of minimal residual disease detection. Blood. 2003; 102:4520-4526.
Li, et al. Utilization of Ig heavy chain variable, diversity, and joining gene segments in children with B-lineage acute lymphoblastic leukemia: implications for the mechanisms of VDJ recombination and for pathogenesis. Blood. Jun. 15, 2004;103(12):4602-9. Epub Mar. 9, 2004.
Logan, et al. High-throughput VDJ sequencing for quantification of minimal residual disease in chronic lymphocytic leukemia and immune reconstitution assessment. Proc Natl Acad Sci U S A. Dec. 27, 2011;108(52):21194-9. Epub Dec. 12, 2011.
Lovisa, et al. IGH and Igk gene rearrangements as PCR targets for pediatric Burkitt's lymphoma and mature B-ALL MRD analysis. Lab Invest. Oct. 2009;89(10):1182-6. Epub Aug. 10, 2009.
Luo et al., "Analysis of the interindividual conservation of T cell receptor α- and β-chain variable regions gene in the peripheral blood of patients with systemic lupus erythematosus," Clin Exp Immunol 154:316-324 (2008).
Margulies, et al. Genome sequencing in microfabricated high-density picolitre reactors. Nature. Sep. 15, 2005;437(7057):376-80. Epub Jul. 31, 2005.
Mato et al., "Correlation of clonal T cell expansion with disease activity in systemic lupus erythematosus," Int Immunol 9(4):547-554 (1997).
Matolcsy, et al. Clonal evolution of B cells in transformation from low- to high-grade lymphoma. Eur J Immunol. Apr. 1999;29(4):1253-64.
Matsumoto et al., "CDR3 spectratyping analysis of the TCR repertoire in myasthenia gravis," J Immunol 176:5100-5107 (2006).
Matsumoto et al., "Complementarity-determining region 3 spectratyping analysis of the TCR repertoire in multiple sclerosis," J Immunol 170:4846-4853 (2003).
Meleshko, et al. Rearrangements of IgH, TCRD and TCRG genes as clonality marker of childhood acute lymphoblastic leukemia. Exp Oncol. Dec. 2005;27(4):319-24.
Menezes et al., "A public T cell clonotype within a heterogeneous autoreactive repertoire is dominant in driving Eae," J Clin Invest 117(8):2176-2185 (2007).
Michalek, et al. Detection and long-term in vivo monitoring of individual tumor-specific T cell clones in patients with metastatic melanoma. J Immunol Jun. 1, 2007;178(11):6789-95.
Miqueu, et al. Statistical analysis of CDR3 length distributions for the assessment of T and B cell repertoire biases. Mol Immunol Feb. 2007;44(6):1057-64. Epub Aug. 22, 2006.
Moss, et al. The human T cell reeptor in health and disease. Annu. Rev. Immunol. 1992; 10:71-96.
Muraro et al., "Molecular tracking of antigen-specific T cell clones in neurological immune-mediated disorders," Brain 126:20-31 (2003).
Nardi, et al. Quantitative monitoring by polymerase colony assay of known mutations resistant to ABL kinase inhibitors. Oncogene. Jan. 31, 2008;27(6):775-82. Epub Aug. 6, 2007, 1-8.
Neale, et al. Comparative analysis of flow cytometry and polymerase chain reaction for the detection of minimal residual disease in childhood acute lymphoblastic leukemia. Leukemia. May 2004;18(5):934-8.

Nguyen, et al. Identification of errors introduced during high throughput sequencing of the T cell receptor repertoire. BMC Genomics. Feb. 11, 2011;12:106.
Notice of allowance dated Jan. 27, 2014 for U.S. Appl. No. 13/100,365.
Notice of allowance dated Feb. 21, 2014 for U.S. Appl. No. 13/468,323.
Notice of allowance dated Mar. 14, 2012 for U.S. Appl. No. 12/615,263.
Notice of allowance dated Aug. 30, 2013 for U.S. Appl. No. 13/763,978.
Notice of allowance dated Nov. 6, 2013 for U.S. Appl. No. 13/100,389.
Notice of allowance dated Dec. 5, 2013 for U.S. Appl. No. 13/214,111.
Notification of Grant dated Jul. 26, 2011 for patent serial No. GB 2467704.
Novak, et al. Single-cell multiplex gene detection and sequencing With microfluidically generated agarose emulsions. Angewandte Chemie. 2011; 50: 390-395, with supplemental material.
Office action dated Feb. 18, 2014 for U.S. Appl. No. 13/459,701.
Office action dated Mar. 13, 2013 for U.S. Appl. No. 13/763,978.
Office action dated Mar. 20, 2013 for U.S. Appl. No. 13/487,980.
Office action dated Apr. 4, 2014 for U.S. Appl. No. 13/459,701.
Office action dated Apr. 22, 2013 for U.S. Appl. No. 13/214,111.
Office action dated May 9, 2012 for U.S. Appl. No. 13/100,395.
Office action dated May 16, 2014 for U.S. Appl. No. 13/196,885.
Office action dated Jun. 6, 2013 for U.S. Appl. No. 13/100,365.
Office action dated Jun. 6, 2013 for U.S. Appl. No. 13/100,389.
Office action dated Jun. 20, 2013 for U.S. Appl. No. 13/214,111.
Office action dated Jul. 5, 2013 for U.S. Appl. No. 13/763,978.
Office action dated Sep. 15, 2011 for U.S. Appl. No. 12/615,263.
Office action dated Oct. 7, 2013 for U.S. Appl. No. 13/459,701.
Office action dated Oct. 16, 2013 for U.S. Appl. No. 13/487,980.
Office action dated Nov. 6, 2013 for U.S. Appl. No. 13/468,323.
Office action dated Nov. 27, 2013 for U.S. Appl. No. 13/196,885.
Office action dated Dec. 6, 2012 for U.S. Appl. No. 13/100,395.
Ogle, et al. Direst measurement of lymphocyte receptor diversity. Nucleic Acids Research. 2003; 31(22):e139.
Okajima et al., "Analysis of T cell receptor Vβ diversity in peripheral CD4+ and CD8+ T lymphocytes in patients with autoimmune thyroid diseases," Clin Exp Immunol 155:166-172 (2008).
Packer et al., "Optimized clonotypic analysis of T-cell receptor repertoire in immune reconstitution," Exp. Hematol 35(3):516-521 (2007).
Panzer-Grumayer, et al. Immunogenotype changes prevail in relapses of young children with TEL-AML1-positive acute lymphoblastic leukemia and derive mainly from clonal selection. Clin Cancer Res. Nov. 1, 2005;11(21):7720-7.
Pels, et al. Clonal evolution as pathogenetic machanism in relapse of primary CNS lymphoma. Neurology. Jul. 13, 2004;63(1):167-9.
Pira, et al. Human naive CD4 T-cell clones specific for HIV envelope persist for years in vivo in the absence of antigenic challenge. J Acquir Immune Defic Syndr. Oct. 1, 2005;40(2):132-9.
Pop, et al. Bioinformatics challenges of new sequencing technology. Trends Genet. Mar. 2008;24(3):142-9.
Ray, et at. Single cell multiplex PCR amplification of five dystrophin gene exons combined with gender determination. Molecular Human Reproduction. 2001; 7(5): 489-494.
Reddy, et al. Systems analysis of adaptive immunity by utilization of high-throughput technologies. Curr Opin Biotechnol. Aug. 2011;22(4):584-9. Epub May 12, 2011.
Reinartz, et al. Massively parallel signature sequencing (MPSS) as a tool for in-depth quantitative gene expression profiling in all organisms. Brief Funct Genomic Proteomic. Feb. 2002;1(1):95-104.
Ria, et al. Collagen-specific T-cell repertoire in blood and synovial fluid varies with disease activity in early rheumatoid arthritis. Arthritis Res Ther. 2008;10(6):R135. Epub Nov. 17, 2008.
Rickison, et al. Human cytotoxic T lymphocyte responses to Epstein-Barr virus infection. Annu Rev Immunol 1997;15:405-31.
Risitano et al., "In-vivo dominant immune responses in aplastic anaemia: molecular tracking of putatively pathogenetic T-cell clones by TCR β-CDR3 sequencing," Lancet 364:355-364 (2004).

(56) References Cited

OTHER PUBLICATIONS

Robins et al., "Comprehensive assessment of T-cell receptor beta-chain diversity in alphabeta T cells," Blood 114(19):4099-4107 (2009).
Robins, et al. Ultra-sensitive detection of rare T cell clones. Immunol Methods. Jan. 31, 2012;375(1-2):14-9. Epub Sep. 10, 2011.
Rosenquist, et al. Clonal evolution as judged by immunoglobulin heavy chain gene rearrangements in relapsing precursor-B acute lymphoblastic leukemia. Eur J Haematol. Sep. 1999;63(3):171-9.
Rougemont, et al. Probabilistic base calling of Solexa sequencing data. BMC Bioinformatics. 2008; 9:431.
Ryan, et al. Clonal evolution of lymphoblastoid cell lines. Lab Invest. Nov. 2006;86(11):1193-200. Epub Oct. 2, 2006.
Schaufelberger, et al. An uneven expression of T cell receptor V genes in the arterial wall and peripheral blood in giant cell arteritis. Inflammation. Dec. 2008;31(6):372-83.
Scholler, et al. Analysis of T cell receptor alpha beta variability in lymphocytes infiltrating melanoma primary tumours and metastatic lesions. Cancer Immunol Immunother. Oct. 1994;39(4):239-48.
Schwab et al., "CD8+ T-cell clones dominate brain infiltrates in *Rasmussen encephalitis* and persist in the periphery," Brain 132:1236-1246 (2009).
Sfanos, et al. Phenotypic analysis of prostate-infiltrating lymphocytes reveals TH17 and Treg skewing. Clin Cancer Res. Jun. 1, 2008;14(11):3254-61. doi: 10.1158/1078-0432.CCR-07-5164.
Shen, et al. Comparing platforms for C. elegans mutant identification using high-throughput whole-genome sequencing. PLoS One. 2008;3(12):e4012.
Sing, et al. A molecular comparison of T lymphocyte populations infiltrating the liver and circulating in the blood of patients with chronic hepatitis B: evidence for antigen-driven selection of a public complementarity-determining region 3 (CDR3) motif. Hepatology. May 2001;33(5):1288-98.
Skulina et al., "Multiple sclerosis: brain-infiltrating CD8+ T cells persist as clonal expansions in the cerebrospinal fluid and blood," PNAS 101(8):2428-2433 (2004).
Sramkova, et al. Detectable minimal residual disease before allogeneic hematopoietic stem cell transplantation predicts extremely poor prognosis in children with acute lymphoblastic leukemia. Pediatr Blood Cancer. Jan. 2007;48(1):93-100.
Steenbergen, et al. Distinct ongoing Ig heavy chain rearrangement processes in childhood B-precursor acute lymphoblastic leukemia. Blood. Jul. 15, 1993;82(2):581-9.
Steward, et al. A polymerase chain reaction study of the stability of Ig heavy-chain and T-cell receptor delta gene rearrangements between presentation and relapse of childhood B-lineage acute lymphoblastic leukemia. Blood. Mar. 1, 1994;83(5):1355-62.
Stewart et al, "Immunoglobulin V regions and the B cell," Blood, 83(7): 1717-1730 (1994).
Struyk, et al. T cell receptors in rheumatoid arthritis. Arthritis Rheum. May 1995;38(5):577-89.
Sumida et al., "T cell receptor repertoire of infiltrating T cells in lips of Sjögren's syndrome patients," J Clin Invest 89:681-685 (1992).
Sumida et al., "T cell receptor Vα repertoire of infiltrating T cells in labial salivary glands from patients with Sjögren's syndrome," J Rheumatol 21: 1655-1661 (1994).
Szczepanski, et al. Comparative analysis of Ig and TCR gene rearrangements at diagnosis and at relapse of childhood precursor-B-ALL provides improved strategies for selection of stable PCR targets for monitoring of minimal residual disease. Blood. Apr. 1, 2002;99(7):2315-23.
Szczepanski, et al. Why and how to quantify minimal residual disease in acute lymphoblastic leukemia? Leukemia. Apr. 2007;21(4):622-6. Epub Feb. 15, 2007.
Tackenberg et al., "Clonal expansions of CD4+ β helper T cells in autoimmune myasthenia gravis," Eur J Immunol 37:849-863 (2007).
Tajiri, et al. Cell-microarray analysis of antigen-specific B-cells: single cell analysis of antigen receptor expression and specificity. Cytometry Part A. 2007; 71A: 961-967.

Thor Straten, et al. T-cell clonotypes in cancer. J Transl Med. Apr. 8, 2004;2(1):11.
Thornhill, et al. A comparison of different lysis buffers to assess allele dropout from single cells for preimplantation genetic diagnosis. Prenatal Diagnosis. 2001; 21:490-497.
Tokimitsu, et al. Single lymphocyte analysis with a microwell array chip. Cytometry. 2007; Part A, 71A: 1003-1010.
UK combined search and examination report dated Mar. 20, 2013 for GB 1300533.5.
UK Combined Search Report and Office action dated Jun. 29, 2012 for UK application No. GB1209668.1.
UK Combined Search Report and Office action dated May 26, 2011 for UK application No. GB1105068.9.
UK office action dated May 25, 2011 for UK application No. GB1009641.0.
UK office action dated Oct. 20, 2010 for UK application No. GB1009641.0.
UK Search Report and office action dated Jan. 12, 2012 for UK application No. GB1120209.0.
UK Search Report and office action dated Jul. 7, 2010 for UK application No. GB1009641.0.
Umibe et al., "Clonal expansion of T cells infiltrating in the airways of non-atopic asthmatics," Clin Exp Immunol 119:390-397 (2000).
Van Der Velden, et al. Analysis of minimal residual disease by Ig/TCR gene rearrangements: guidelines for interpretation of real-time quantitative PCR data. Leukemia. Apr. 2007;21(4):604-11. Epub Feb. 8, 2007.
Van Der Velden, et al. Detection of minimal residual disease in hematologic malignancies by real-time quantitative PCR: principles, approaches, and laboratory aspects. Leukemia. Jun. 2003;17(6):1013-34.
Van Dongen, et al. Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia. Dec. 2003;17(12):2257-317.
Wang, et al. High throughput sequencing reveals a complex pattern of dynamic interrelationships among human T cell subsets. Proc Natl Acad Sci U S A. Jan. 26, 2010; 107(4): 1518-1523.
Wang, et al. Quantitative measurement of pathogen-specific human memory T cell repertoire diversity using a CDR3 beta-specific microarray. BMC Genomics. Sep. 19, 2007;8:329.
Warren et al., "Profiling model T-cell metagenomes with short reads," Bioinformatics 25(4):458-464 (2009).
Warren, et al. Exhaustive T-cell repertoire sequencing of human peripheral blood samples reveals signatures of antigen selection and a directly measured repertoire size of at least 1 million clonotypes. Genome Res. Feb. 24, 2011. [Epub ahead of print].
Weinstein et al., "High-throughput sequencing of the zebrafish antibody repertoire," Science 324:807-810 (2009).
Wells, et al. Strategies for preimplantation genetic diagnosis of single gene disorders by DNA amplification. Prenatal Diagnosis. 1998; 18: 1389-1401.
Wetmur, et al. An emulsion polymerase chain reaction-based method for molecular haplotyping. Methods in Molecular Biology. 1996; 410: 351-361.
Wetmur, et al. Linking emulsion PCR haplotype analysis. chapter 11, in Park (editor), PCR Protocols, Methods En Molecular Biology. 2011; 687: 165-175.
Wetmur, et al. Molecular haplotyping by linking emulsion PCR: analysis of paraoxonase 1 haplotypes and phenotypes. Nucleic Acids Research. 2005; 33(8):2615-2619.
Wlodarski, et al. Molecular strategies for detection and quantitation of the clonal cytotoxic T-cell responses in aplastic anemia and myelodysplastic syndrome. Blood. 2006; 108:2632-2641.
Wlodarski, et al. Pathologic clonal cytotoxic T-cell responses: nonrandom nature of the T-cell-receptor restriction in large granular lymphocyte leukemia. Blood. 2005; 106:2769-2779.
Wu, et al. High-throughput sequencing detects minimal residual disease in acute T lymphoblastic leukemia. Sci Transl Med. May 16, 2012;4(134):134ra63. doi:10.1126/scitranslmed.3003656.
Yin et al., "Antiretroviral therapy restores diversity in the T-cell receptor Vβ repertoire of CD4 T-cell subpopulations among human

(56) References Cited

OTHER PUBLICATIONS immunodeficiency virus type 1-infected children and adolescents," Clin Vac Immunol 16(9):1293-1301 (2009).
Yon, et al. Precise gene fusion by PCR. Nucleic Acids Research. 1989; 17(12):4895.
Zaliova, et al. Quantification of fusion transcript reveals a subgroup with distinct biological properties and predicts relapse in BCR/ABL-positive ALL: implications for residual disease monitoring. Leukemia. May 2009;23(5):944-51. Epub Jan. 22, 2009.
Zeng, et al. High-performance single cell genetic analysis using microfluidic emulsion generator arrays. Anal. Chem. 2010; 82:3183-3190.
Zhou, et al. High throughput analysis of TCR-beta rearrangement and gene expression in single cells. 2006; 86:314-321.
Office action dated Aug. 11, 2014 for U.S. Appl. No. 13/196,885.
PCT/US2014/044971, Appln filed Jun. 30, 2014, Asbury et al.
PCT/US2014/047909, Appln filed Jul. 31, 2014, Klinger et al.
U.S. Appl. No. 14/317,087, filed Jun. 27, 2014, Asbury et al.
U.S. Appl. No. 14/363,276, filed Jun. 5, 2014, Faham et al.
U.S. Appl. No. 14/363,956, filed Jun. 9, 2014, Faham et al.
U.S. Appl. No. 14/364,961, filed Jun. 12, 2014, Faham et al.
U.S. Appl. No. 14/366,840, filed Jun. 19, 2014, Faham.
U.S. Appl. No. 14/383,101, filed Sep. 4, 2014, Faham et al.
U.S. Appl. No. 14/383,102, filed Sep. 4, 2014, Faham
Nie, et al. Optical detection of single molecules. Annu Rev Biophys Biomol Struct. 1997;26:567-96.
Office action dated Aug. 26, 2014 for U.S. Appl. No. 14/075,075.
U.S. Appl. No. 61/112,693, filed Nov. 7, 2008, Faham et al.
Abath, et al. Single-tube nested PCR using immobilized internal primers. Biotechniques. Dec. 2002;33(6):1210-2, 1214.
Altin, et al. The role of CD45 and CD45-associated molecules in T cell activation. Immunol Cell Biol. Oct. 1997;75(5):430-45.
Arnaout. Specificity and overlap in gene segment-defined antibody repertoires. C Genomics. Oct. 28, 2005;6:148.
Damle, et al. B-cell chronic lymphocytic leukemia cells express a surface membrane phenotype of activated, antigen-experienced B lymphocytes. Blood. Jun. 1, 2002;99(11):4087-93.
De Bona, et al. Optimal spliced alignments of short sequence reads. Bioinformatics. Aug. 15, 2008;24(16):i174-80. doi: 10.1093/bioinformatics/btn300.
Diluvio, et al. Identical TCR beta-chain rearrangements in streptococcal angina and skin lesions of patients with psoriasis vulgaris. J Immunol. Jun. 1, 2006;176(11):7104-11.
Dressman, et al. Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Droege, et al. The Genome Sequencer FLX System—longer reads, more applications, straight forward bioinformatics and more complete data sets. J Biotechnol. Aug. 31, 2008;136(1-2):3-10. doi: 10.1016/j.jbiotec.2008.03.021. Epub Jun. 21, 2008.
Eisenstein. Personalized, sequencing-based immune profiling spurs startups. Nat Biotechnol. Mar. 2013;31(3):184-6. doi: 10.1038/nbt0313-184b.
Erlich, et al. Alta-Cyclic: a self-optimizing base caller for next-generation sequencing. Nat Methods. Aug. 2008;5(8):679-82. doi: 10.1038/nmeth.1230. Epub Jul. 6, 2008.
European opposition dated Oct. 14, 2014 for EP Application No. 09764971.1. Reference# 547-7.
European opposition dated Oct. 14, 2014 for EP Application No. 09764971.1. Reference# BRO-O001EP.
European opposition dated Oct. 15, 2014 for EP Application No. 09764971.1. (in French only).
Furmanski, et al. Public T cell receptor beta-chains are not advantaged during positive selection. J Immunol. Jan. 15, 2008;180(2):1029-39.
Giga—Roche 454 FLX technology how it works. Fiche technique du Centre Interdisciplinaire de Genoproteomique Appliquee (Universite de Liege, Belgique). Accessed Oct. 15, 2014.
Gomes, et al. Single-tube nested PCR using immobilized internal primers for the identification of dengue virus serotypes. J Virol Methods. Oct. 2007;145(1):76-9. Epub Jun. 15, 2007.
Gupta. Single-molecule DNA sequencing technologies for future genomics research. Trends Biotechnol. Nov. 2008;26(11):602-11. doi: 10.1016/j.tibtech.2008.07.003. Epub Aug. 21, 2008.
Heger. Roche's 454 Eyes Immune Repertoire Sequencing as Key Application for Long-Read Platform. Feb. 2, 2010. http://www.genomeweb.com/print/932624.
IlluminA Systems & Software, Technology Spotlight, DNA Sequencing with Solexa® Technology, Illumina, Inc., Pub. No. 770-2007-002, 2007.
Jurkat, Clone 6-1 (ATCC TIB-152) Webpage retrievable from the ATCC under http://www.lgcstandards-atcc.org/Products/A11MB-152.aspx#characteristics. Accessed Oct. 14, 2014.
Lin, et al. Multiplex genotype determination at a large number of gene loci. Proc Natl Acad Sci U S A. Mar. 19, 1996;93(6):2582-7.
Lowe, et al. A computer program for selection of oligonucleotide primers for polymerase chain reactions. Nucleic Acids Res. Apr. 11, 1990;18(7):1757-61.
Mardis. Next-generation DNA sequencing methods. Annu Rev Genomics Hum Genet. 2008;9:387-402. doi: 10.1146/annurev.genom.9.081307.164359.
Miceli, et al. The roles of CD4 and CD8 in T cell activation. Semin Immunol. May 1991;3(3):133-41. Abstract only.
Office action dated May 2, 2011 for U.S. Appl. No. 12/425,310.
Office action dated May 8, 2014 for U.S. Appl. No. 12/425,310.
Office action dated Aug. 6, 2010 for U.S. Appl. No. 12/425,310.
Quick. SOLiD System—a next-gen DNA sequencing platform announced, Gizmag online magazine, http://www.mizmag.com/go/8248, pp. 1-5, Oct. 2007.
Robins. Immunosequencing: applications of immune repertoire deep sequencing. Curr Opin Immunol. Oct. 2013;25(5):646-52. doi: 10.1016/j.coi.2013.09.017. Epub Oct. 16, 2013.
Sequenta and iRepertoire Join Forces on Blood Cancer Testing. BusinessWire. Aug. 8, 2013. http://www.businesswire.com/news/home/20130808005363/en/Sequenta-iRepertoire-Join-Forces-Blo . . . #.VGTT9Wd0yUk.
Shendure, et al. Advanced sequencing technologies: methods and goals. Nat Rev Genet. May 2004;5(5):335-44.
Shendure, et al. Next-generation DNA sequencing. Nat Biotechnol. Oct. 2008;26(10):1135-45. doi: 10.1038/nbt1486.
Stanley. Essentials of Immunology & Serology, Delmar, Thomson Learning, Chapter 7, T cells, p. 95, 2002.
Striebich, et al. Selective accumulation of related CD4+ T cell clones in the synovial fluid of patients with rheumatoid arthritis. J Immunol Oct. 15, 1998;161(8):4428-36.
Supplemental material of Weinstein, et al. High-throughput sequencing of the zebrafish antibody repertoire. Science. May 8, 2009;324(5928):807-10. doi: 10.1126/science.1170020.www.sciencemag.org/cgi/content/full/324/5928/807/DC1.
Vanderborght, et al. Dynamic T cell receptor clonotype changes in synovial tissue of patients with early rheumatoid arthritis: effects of treatment with cyclosporin A (Neoral). J Rheumatol. Mar. 2002;29(3):416-26.
Wang, et al. HIV integration site selection: analysis by massively parallel pyrosequencing reveals association with epigenetic modifications. Genome Res. Aug. 2007;17(8):1186-94. Epub Jun. 1, 2007.
Notice of allowance dated Sep. 12, 2014 for U.S. Appl. No. 13/214,111.
Office action dated Oct. 8, 2014 for U.S. Appl. No. 13/459,701.
Bertness, et al. T-cell receptor gene rearrangements as clinical markers of human T-cell lymphomas. N Engl J Med. Aug. 29, 1985;313(9):534-8.
Qu, et al. Efficient frequency-based de novo short-read clustering for error trimming in next-generation sequencing. Genome Res. Jul. 2009;19(7):1309-15. doi: 10.1101/gr.089151.108. Epub May 13, 2009.
Weiss, et al. Clonal rearrangements of T-cell receptor genes in mycosis fungoides and dermatopathic lymphadenopathy. N Engl J Med. Aug. 29, 1985;313(9):539-44.
Office action dated Apr. 10, 2015 for U.S. Appl. No. 13/214,111.
Office action dated Apr. 3, 2015 for U.S. Appl. No. 13/861,941.

(56) References Cited

OTHER PUBLICATIONS

Sandberg, et al. Capturing whole-genome characteristics in short sequences using a naive Bayesian classifier. Genome Res. Aug. 2001;11(8):1404-9.
U.S. Appl. No. 14/611,878, filed Feb. 2, 2015, Moorhead et al.
U.S. Appl. No. 14/640,145, filed Mar. 6, 2015, Robins et al.
Akatsuka, et al. Rapid screening of T-cell receptor (TCR) variable gene usage by multiplex PCR: application for assessment of clonal composition. Tissue Antigens. Feb. 1999;53(2):122-34.
Alexandre, D., et al. "H. sapiens rearranged T-cell receptor gamma chain gene, V3RS-J1 (hybrid joint)," GenBank accession No: X57740, NCBI, Feb. 11, 1997, 8 pages [online] [retrieved on Jun. 26, 2013] Retrieved from the internet <URL:http://www.ncbi.nlm.nih.gov/nuccore/x57740>.
Alexandre, D., et al. "H. sapiens rearranged T-cell receptor gamma chain gene, V2-JP1," GenBank accession No: X57737, NCBI, Nov. 14, 2006, 8 pages [online] [retrieved on Jun. 26, 2013] Retrieved from the internet <URL:http://www.ncbi.nlm.nih.gov/nuccore/x57737>.
Al-Lazikani, et al. Standard conformations for the canonical structures of immunoglobulins. J Mol Biol. Nov. 7, 1997;273(4):927-48.
Bahloul, et al. Clinical impact of molecular diagnostics in low-grade lymphoma. Best Pract Res Clin Haematol. Mar. 2005;18(1):97-111.
Bernardin, et al. Estimate of the total number of CD8+ clonal expansions in healthy adults using a new DNA heteroduplex-tracking assay for CDR3 repertoire analysis. J Immunol Methods. Mar. 1, 2003;274(1-2):159-75.
Blow. PCR's next frontier. Nature Methods. Oct. 2007; 4(10):869-875.
Bradfield, et al. Graft-versus-leukemia effect in acute lymphoblastic leukemia: the importance of tumor burden and early detection. Leukemia. Jun. 2004;18(6):1156-8.
Brenan, et al. High throughput, nanoliter quantitative PCR. Drug Discov Today Technol. 2005 Autumn;2(3):247-53. doi: 10.1016/j.ddtec.2005.08.017.
Buck, et al. Design strategies and performance of custom DNA sequencing primers. Biotechniques. Sep. 1999;27(3):528-36.
Cave, et al. Clinical significance of minimal residual disease in childhood acute lymphoblastic leukemia. European Organization for Research and Treatment of Cancer—Childhood Leukemia Cooperative Group. N Engl J Med. Aug. 27, 1998;339(9):591-8.
Chothia, et al. Canonical structures for the hypervariable regions of immunoglobulins. J Mol Biol. Aug. 20, 1987;196(4):901-17.
Chothia, et al. Conformations of immunoglobulin hypervariable regions. Nature. Dec. 21-28, 1989;342(6252):877-83.
Ciudad, et al. Detection of abnormalities in B-cell differentiation pattern is a useful tool to predict relapse in precursor-B-ALL. Br J Haematol. Mar. 1999;104(4):695-705.1
Coustan-Smith, et al. Clinical importance of minimal residual disease in childhood acute lymphoblastic leukemia. Blood. Oct. 15, 2000;96(8):2691-6.
Coustan-Smith, et al. Early T-cell precursor leukaemia: a subtype of very high-risk acute lymphoblastic leukaemia. Lancet Oncol. Feb. 2009;10(2):147-56. doi: 10.1016/S1470-2045(08)70314-0. Epub Jan. 13, 2009.
Coustan-Smith, et al. Prognostic importance of measuring early clearance of leukemic cells by flow cytometry in childhood acute lymphoblastic leukemia. Blood. Jul. 1, 2002;100(1):52-8.
Curran-Everett. Multiple comparisons: philosophies and illustrations. Am J Physiol Regul Integr Comp Physiol. Jul. 2000;279(1):R1-8.
De Jonge, et al. Evidence based selection of housekeeping genes. PLoS One. Sep. 19, 2007;2(9):e898.
Denucci, et al. Integrin function in T-cell homing to lymphoid and nonlymphoid sites: getting there and staying there. Crit Rev Immunol Sep. 15, 2009;29(2):87-109.
Dheda, et al. Validation of housekeeping genes for normalizing RNA expression in real-time PCR. Biotechniques. Jul. 2004;37(1):112-4, 116, 118-9.
Dik, et al. New insights on human T cell development by quantitative T cell receptor gene rearrangement studies and gene expression profiling. J Exp Med. Jun. 6, 2005;201(11):1715-23. Epub May 31, 2005.
Droese, et al. Validation of Biomed-2 multiplex PCR tubes for detection of TCRB gene rearrangements in T-cell malignancies. Leukemia. Sep. 2004;18(9):1531-8.
Duby, et al. Human T-cell receptor aberrantly rearranged beta-chain J1.5-Dx-J2.1 gene. Proc. Natl. Acad. Sci. USA (1986) GenBank accession No. M13574.1, bases 1 to 100.
Edwards, et al. Multiplex PCR: advantages, development, and applications. PCR Methods Appl. Feb. 1994;3(4):S65-75.
Elnifro, et al. Multiplex PCR: optimization and application in diagnostic virology. Clin Microbiol Rev. Oct. 2000;13(4):559-70.
European search report and opinion dated May 29, 2012 for EP Application No. 10732172.1.
Flohr, et al. Minimal residual disease-directed risk stratification using real-time quantitative PCR analysis of immunoglobulin and T-cell receptor gene rearrangements in the international multicenter trial AIEOP-BFM ALL 2000 for childhood acute lymphoblastic leukemia. Leukemia. Apr. 2008;22(4):771-82. doi: 10.1038/leu.2008.5. Epub Jan. 31, 2008.
Henegariu, et al. Multiplex PCR: critical parameters and step-by-step protocol. Biotechniques. Sep. 1997;23(3):504-11.
Hwang, et al. Identification of a commonly used CDR3 region of infiltrating T cells expressing Vbeta13 and Vbeta15 derived from psoriasis patients. J Invest Dermatol. Mar. 2003;120(3):359-64.
International Preliminary Report on Patentability dated Apr. 24, 2014 for PCT/US2013/040221.
Kalinina, et al. Nanoliter scale PCR with TaqMan detection. Nucleic Acids Res. May 15, 1997;25(10):1999-2004.
Kaplinski, et al. MultiPLX Automatic Grouping and Evaluation of PCR Primers. In Methods in Molecular Biology, vol. 402: PCR Primer Design, Nov. 25, 2004, pp. 287-303.
Katz, et al. T cell infiltrate predicts long-term survival following resection of colorectal cancer liver metastases. Ann Surg Oncol. Sep. 2009;16(9):2524-30. doi: 10.1245/s10434-009-0585-3. Epub Jul. 1, 2009.
Kehrl, et al. Chemoattract receptor signaling and its role in lymphocyte motility and trafficking. Curr Top Microbiol Immunol Mar. 25, 2009;334:107-27. doi: 10.1007/978-3-540-93864-4_5.
Kiianitsa, et al., "Development of Tools for T-Cell Repertoire Analysis (TCRB Spectratyping) for the Canine Model of Hematopoietic Cell Transplantation", Blood, ASH—Annual Meeting Abstracts, Nov. 2007, 110(11), Abstract 4873.
Ladetto, et al. Real-time polymerase chain reaction in multiple myeloma: quantitative analysis of tumor contamination of stem cell harvests. Exp Hematol. Jun. 2002;30(6):529-36.
Ladetto, et al. Real-Time polymerase chain reaction of immunoglobulin rearrangements for quantitative evaluation of minimal residual disease in multiple myeloma. Biol Blood Marrow Transplant. 2000;6(3):241-53.
Lucio, et al. Flow cytometric analysis of normal B cell differentiation: a frame of reference for the detection of minimal residual disease in precursor-B-ALL. Leukemia. Mar. 1999;13(3):419-27.
Mariani, et al. Comprehensive assessment of the TCRBV repertoire in small T-cell samples by means of an improved and convenient multiplex PCR method. Exp Hematol. Jun. 2009;37(6):728-38. doi: 10.1016/j.exphem.2009.03.003.
Markoulatos, et al. Multiplex polymerase chain reaction: a practical approach. J Clin Lab Anal. 2002;16(1):47-51.
Maryanski, et al. A quantitative, single-cell PCR analysis of an antigen-specific TCR repertoire selected during an in vivo CD8 response: direct evidence for a wide range of clone sizes with uniform tissue distribution. Mol Immunol. Aug. 1999;36(11-12):745-53.
Maslanka, et al. Molecular analysis of T cell repertoires. Spectratypes generated by multiplex polymerase chain reaction and evaluated by radioactivity or fluorescence. Hum Immunol. Sep. 1995;44(1):28-34.
Merriam-Webster (attached; definition of "e.g.," accessed Apr. 25, 2014) http://www.merriam-webster.com/dictionary/e.g.

(56) References Cited

OTHER PUBLICATIONS

Merriam-Webster (attached; definition of "substantial," accessed Apr. 25, 2014) http://www.merriam-webster.com/dictionary/substantial.
Monod, et al. IMGT/JunctionAnalysis: the first tool for the analysis of the immunoglobulin and T cell receptor complex V-J and V-D-J JUNCTIONs. Bioinformatics. Aug. 4, 2004;20 Suppl 1:i379-85.
NCBI Accession No. L36092 "Homo sapiens germline beta T-cell receptor locus," NCBI, Jun. 26, 2009, 254 Pages, can be retrieved at <URL:http://www.ncbi.nlm.nih.gov/nuccore/L36092>.
Nicot, et al. Housekeeping gene selection for real-time RT-PCR normalization in potato during biotic and abiotic stress. J Exp Bot. Nov. 2005;56(421):2907-14. Epub Sep. 27, 2005.
Nolan, et al. Quantification of mRNA using real-time RT-PCR. Nat Protoc. 2006;1(3):1559-82.
Notice of allowance dated Feb. 17, 2015 for U.S. Appl. No. 12/425,310.
Notice of allowance dated Oct. 10, 2013 for U.S. Appl. No. 12/794,507.
Office action dated Jan. 16, 2014 for U.S. Appl. No. 13/656,265.
Office action dated Feb. 27, 2015 for U.S. Appl. No. 14/075,075.
Office action dated Apr. 4, 2014 for U.S. Appl. No. 12/794,507.
Office action dated Apr. 26, 2013 for U.S. Appl. No. 12/794,507.
Office action dated May 16, 2014 for U.S. Appl. No. 14/183,163.
Office action dated Jun. 6, 2014 for U.S. Appl. No. 14/183,177.
Office action dated Jun. 16, 2014 for U.S. Appl. No. 14/252,189.
Office action dated Jul. 10, 2013 for U.S. Appl. No. 13/217,126.
Office action dated Jul. 10, 2014 for U.S. Appl. No. 12/794,507.
Office action dated Jul. 11, 2014 for U.S. Appl. No. 13/217,126.
Office action dated Jul. 18, 2014 for U.S. Appl. No. 13/656,265.
Office action dated Oct. 1, 2014 for U.S. Appl. No. 14/183,177.
Office action dated Oct. 2, 2014 for U.S. Appl. No. 14/183,163.
Office action dated Oct. 9, 2014 for U.S. Appl. No. 14/252,189.
Office action dated Nov. 7, 2012 for U.S. Appl. No. 12/794,507.
Office action dated Dec. 2, 2014 for U.S. Appl. No. 14/095,629.
Office action for Australian Patent Application No. 2010263172, Jul. 9, 2014, 4 Pages.
Office Action for Canadian Patent Application No. 2,765,949, Mailed Apr. 3, 2014, 4 Pages.
Office Action for European Patent Application No. EP 10722512.0, Dec. 17, 2012, 5 Pages.
Office Action for Israel Patent Application No. IL 217200, Jan. 21, 2013, 4 Pages.
Office action for Israel Patent Application No. IL 217200, Mar. 18, 2014, 8 Pages.
Office action for Korean Patent Application No. 10-2011-7030953, May 30, 2014, 5 Pages.
Office action for Russian Patent Application No. 2012101828/10(002474), Mar. 28, 2014, 5 Pages.
PCT International Search Report and Written Opinion for PCT/US2013/040221, Sep. 23, 2013, 16 Pages.
PCT International Search Report and Written Opinion, PCT Application No. PCT/US2010/021264, Apr. 14, 2010, 7 pages.
PCT International Search Report and Written Opinion, PCT/2013/045994, Oct. 25, 2013, 16 Pages.
PCT International Search Report and Written Opinion, PCT/US2010/037477, Sep. 24, 2010, 10 pages.
PCT International Search Report and Written Opinion, PCT/US2011/049012, Apr. 10, 2012, 9 Pages.
PCT International Search Report and Written Opinion, PCT/US2011/026373, Oct. 20, 2011, 14 Pages.
PCT International Search Report and Written Opinion, PCT/US2012/061193, Mar. 28, 2013, 12 Pages.
PCT International Search Report and Written Opinion, PCT/US2012/068617, Jun. 13, 2013, 8 Pages.
PCT International Search Report and Written Opinion, PCT/US2013/062925, Nov. 25, 2013, 12 Pages.
Pohl, et al. Principle and applications of digital PCR. Expert Rev Mol Diagn. Jan. 2004;4(1):41-7.
Puisieux, et al. Oligoclonality of tumor-infiltrating lymphocytes from human melanomas. J Immunol. Sep. 15, 1994;153(6):2807-18.
Rasmussen, et al. Quantitation of minimal residual disease in multiple myeloma using an allele-specific real-time PCR assay. Exp Hematol. Sep. 2000;28(9):1039-45.
Reischl, et al. Quantitative PCR. A survey of the present technology. Mol Biotechnol. Feb. 1995;3(1):55-71.
Rock, et al. CDR3 length in antigen-specific immune receptors. J Exp Med. Jan. 1, 1994;179(1):323-8.
Rozen, et al. Primer3 on the WWW for general users and for biologist programmers. Methods Mol Biol. 2000;132:365-86.
Saada, et al. Models for antigen receptor gene rearrangement: CDR3 length. Immunol Cell Biol. Jun. 2007;85(4):323-32. Epub Apr. 3, 2007.
Santalucia. Physical principles and visual-OMP software for optimal PCR design. Methods Mol Biol. 2007;402:3-34.
Santamaria, et al. Beta-cell-cytotoxic CD8+ T cells from nonobese diabetic mice use highly homologous T cell receptor alpha-chain CDR3 sequences. J Immunol Mar. 1, 1995;154(5):2494-503.
Silver, et al. Selection of housekeeping genes for gene expression studies in human reticulocytes using real-time PCR. BMC Mol Biol. Oct. 6, 2006;7:33.
Standard Sequencing Primers, Max Planck Genome Center Cologne, Jan. 15, 2011, downloaded from https://genomecentre.mpipz.mpg.de/SeqOrderDB/export/sequencing-primers.html.
Stein, et al. Chemokine control of lymphocyte trafficking: a general overview. Immunology. Sep. 2005;116(1):1-12.
Steinmetz, et al. Chemokines and B cells in renal inflammation and allograft rejection. Frontiers in Bioscience (Schol. Ed.), Jun. 1, 2009, vol. 1, pp. 13-22.
Szczepanski, et al. Minimal residual disease in leukaemia patients. Lancet Oncol. Jul. 2001;2(7):409-17.
Tewhey, et al. Microdroplet-based PCR enrichment for large-scale targeted sequencing. Nat Biotechnol. Nov. 2009;27(11):1025-31. doi: 10.1038/nbt.1583. Epub Nov. 1, 2009.
Triebel, et al. A unique V-J-C-rearranged gene encodes a gamma protein expressed on the majority of CD3+ T cell receptor-alpha/beta- circulating lymphocytes. J Exp Med. Feb. 1, 1988;167(2):694-9.
Van Der Velden, et al. Optimization of PCT-based minimal residual disease diagnostics for childhood acute lymphoblastic leukemia in a multi-center setting. Leukemia. Apr. 2007;21(4):706-13. Epub Feb. 8, 2007.
Van Der Velden, et al. Real-time quantitative PCR for detection of minimal residual disease before allogeneic stem cell transplantation predicts outcome in children with acute lymphoblastic leukemia. Leukemia. Sep. 2001;15(9):1485-7.
Van Dongen, et al. Prognostic value of minimal residual disease in acute lymphoblastic leukaemia in childhood. Lancet. Nov. 28, 1998;352(9142):1731-8.
Venturi, et al. TCR beta-chain sharing in human CD8+ T cell responses to cytomegalovirus and EBV. J Immunol. Dec. 1, 2008;181(11):7853-62.
Venturi, et al. The molecular basis for public T-cell responses? Nat Rev Immunol. Mar. 2008;8(3):231-8. doi: 10.1038/nri2260.
Verhagen, et al. Application of germline IGH probes in real-time quantitative PCR for the detection of minimal residual disease in acute lymphoblastic leukemia. Leukemia. Aug. 2000;14(8):1426-35.
Vogelstein, et al. Digital PCR. Proc Natl Acad Sci U S A. Aug. 3, 1999;96(16):9236-41.
Ward, et al. Mechanisms of chemokine and antigen-dependent T-lymphocyte navigation. Biochem J. Feb. 15, 2009;418(1):13-27. doi: 10.1042/BJ20081969.
Wood. 9-color and 10-color flow cytometry in the clinical laboratory. Arch Pathol Lab Med. May 2006;130(5):680-90.
U.S. Appl. No. 14/640,145, filed Mar. 6, 2015, Livingston et al.
Office action dated Apr. 17, 2015 for U.S. Appl. No. 13/459,701.
Office action dated Jun. 19, 2015 for U.S. Appl. No. 13/905,406.
Han, et al. Immunorepertoire analysis by multiplex PCR amplification and high throughput sequencing. J. of Immunol., vol. 182, Apr. 15, 2009. Abstract.

(56) References Cited

OTHER PUBLICATIONS

Wang, et al. Immunorepertoire analysis by multiplex PCR amplification and high throughput sequencing. Poster-Program 42.6, The 96th Annual Meeting of the America Association of Immunologists, Seattle, USA. May 8-12, 2009.
U.S. Appl. No. 14/436,851, filed Apr. 17, 2015, Klinger et al.
U.S. Appl. No. 14/436,855, filed Apr. 17, 2015, Carlton et al.
U.S. Appl. No. 14/437,470, filed Apr. 21, 2015, Faham.
Office action dated May 8, 2015 for U.S. Appl. No. 14/242,299.
Office action dated Jun. 4, 2015 for U.S. Appl. No. 13/908,813.
Office action dated Jul. 8, 2015 for U.S. Appl. No. 14/176,551.
Office action dated May 22, 2015 for U.S. Appl. No. 14/243,875.
Office action dated Jul. 17, 2015 for U.S. Appl. No. 14/075,075.
U.S. Appl. No. 14/404,435, filed Nov. 26, 2014, Faham et al.
Notice of allowance dated Dec. 15, 2014 for U.S. Appl. No. 13/196,885.
PCT/US2014/061260, Appln filed Oct. 17, 2014, Faham et al.
Drossman, et al. High-speed separations of DNA sequencing reactions by capillary electrophoresis. Anal Chem. May 1, 1990;62(9):900-3.
Office action dated Nov. 20, 2014 for U.S. Appl. No. 13/214,111.
US 8,642,750, 02/2014, Robins et al. (withdrawn)

\* cited by examiner

FIG. 4

A. BCR amplification- C side

```
J00230|IGHG2*01|Homo    -CCTCCACCAAGGGCCCATCCGTCTTCCCCCTGGCGCCCTGCTCCAGGAG  49
AJ250170|IGHG2*02|Homo  -CCTCCACCAAGGGCCCATCCGTCTTCCCCCTGGCGCCCTGCTCCAGGAG  49
AL928742|IGHG2*06|Homo  -CCTCCACCAAGGGCCCATCCGTCTTCCCCCTGGCGCCCTGCTCCAGGAG  49
AF449617|IGHG2*04|Homo  -CCTCCACCAAGGGCCCATCCGTCTTCCCCCTGGCGCCCTGCTCCAGGAG  49
K01316|IGHG4*01|Homo    -CTTCCACCAAGGGCCCATCCGTCTTCCCCCTGGCGCCCTGCTCCAGGAG  49
AL928742|IGHG4*04|Homo  -CTTCCACCAAGGGCCCATCCGTCTTCCCCCTGGCGCCCTGCTCCAGGAG  49
                        * ************************* **** **************  
```

Primary PCR

Secondary PCR

P5

Cluster formation

Sequencing primer

FIG. 4 cont.

B. BCR amplification- V side

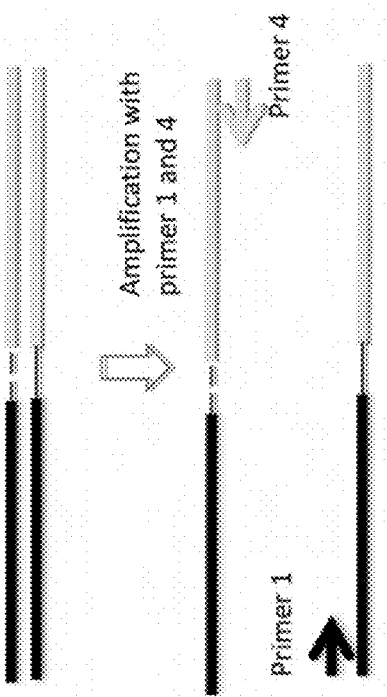
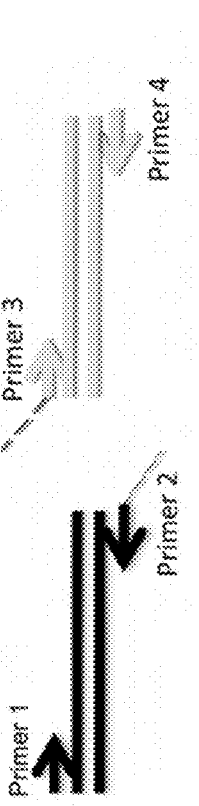
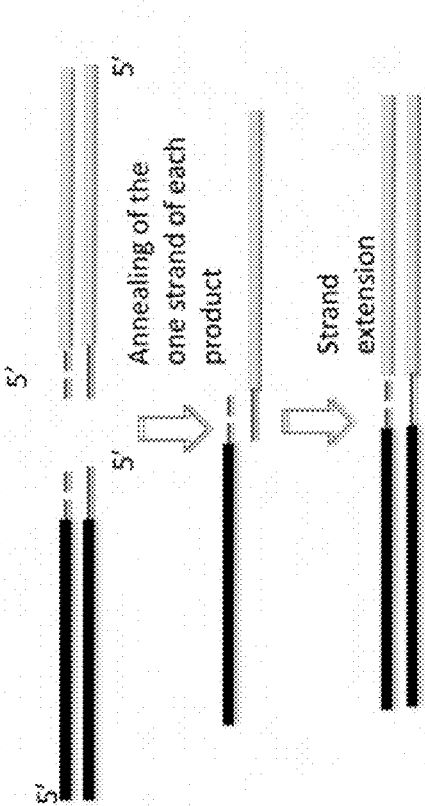
FIG. 9

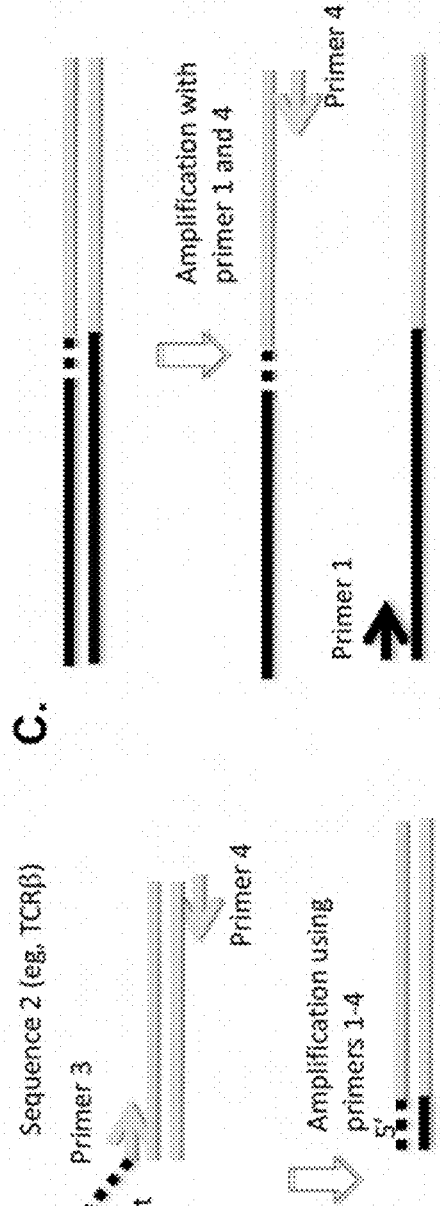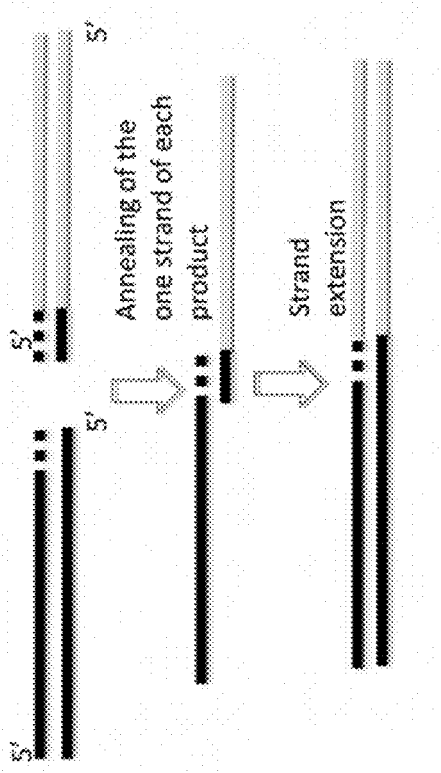
FIG. 10

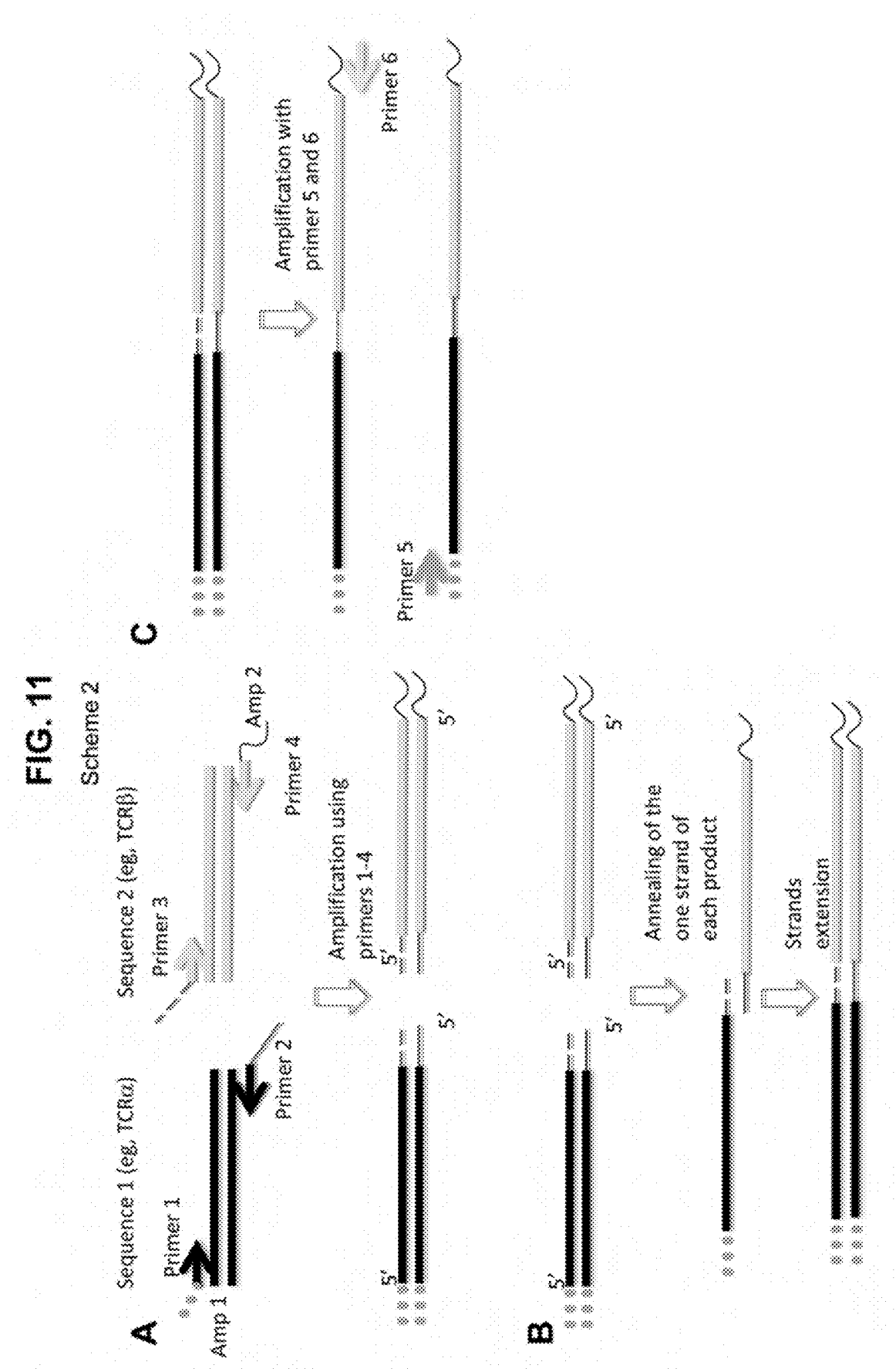

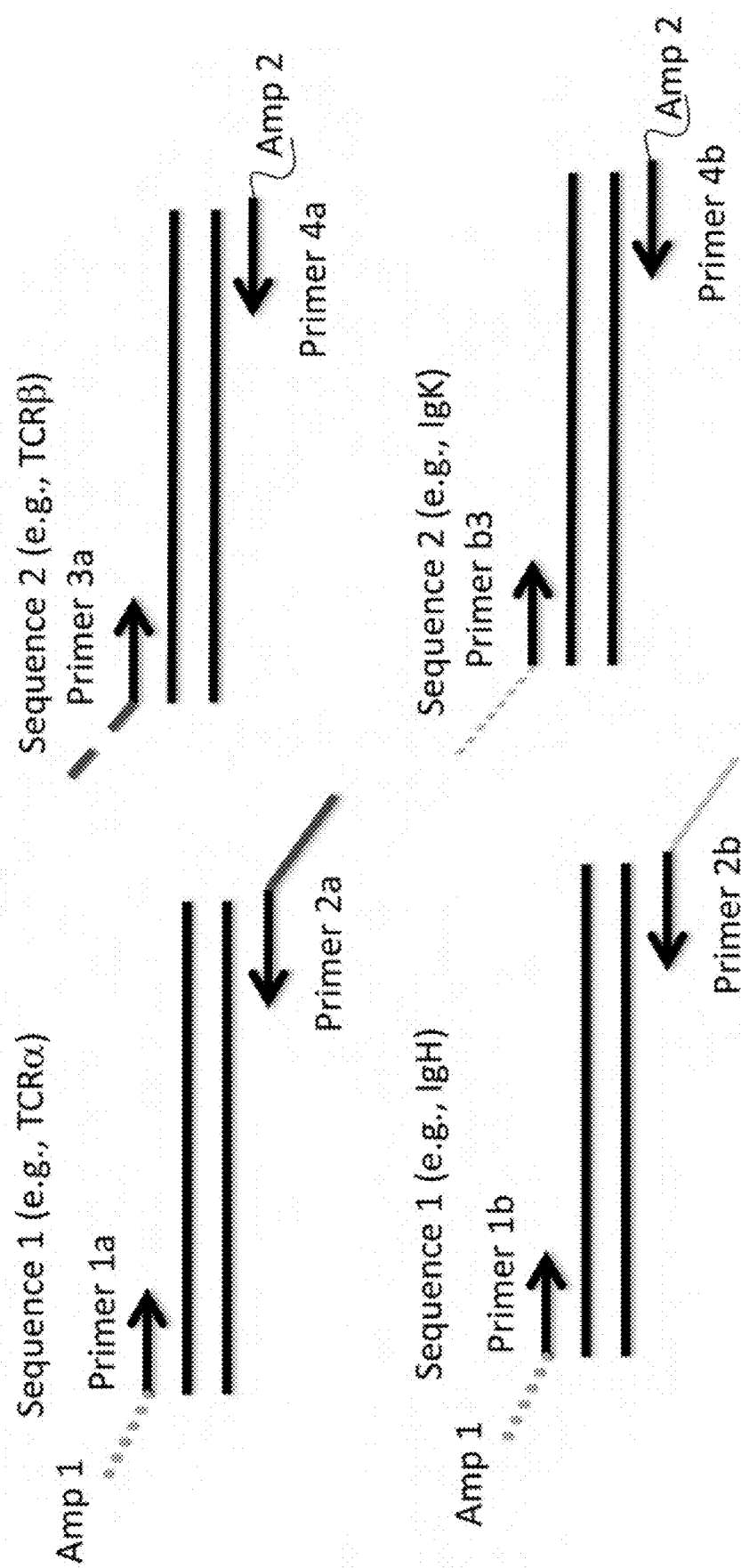

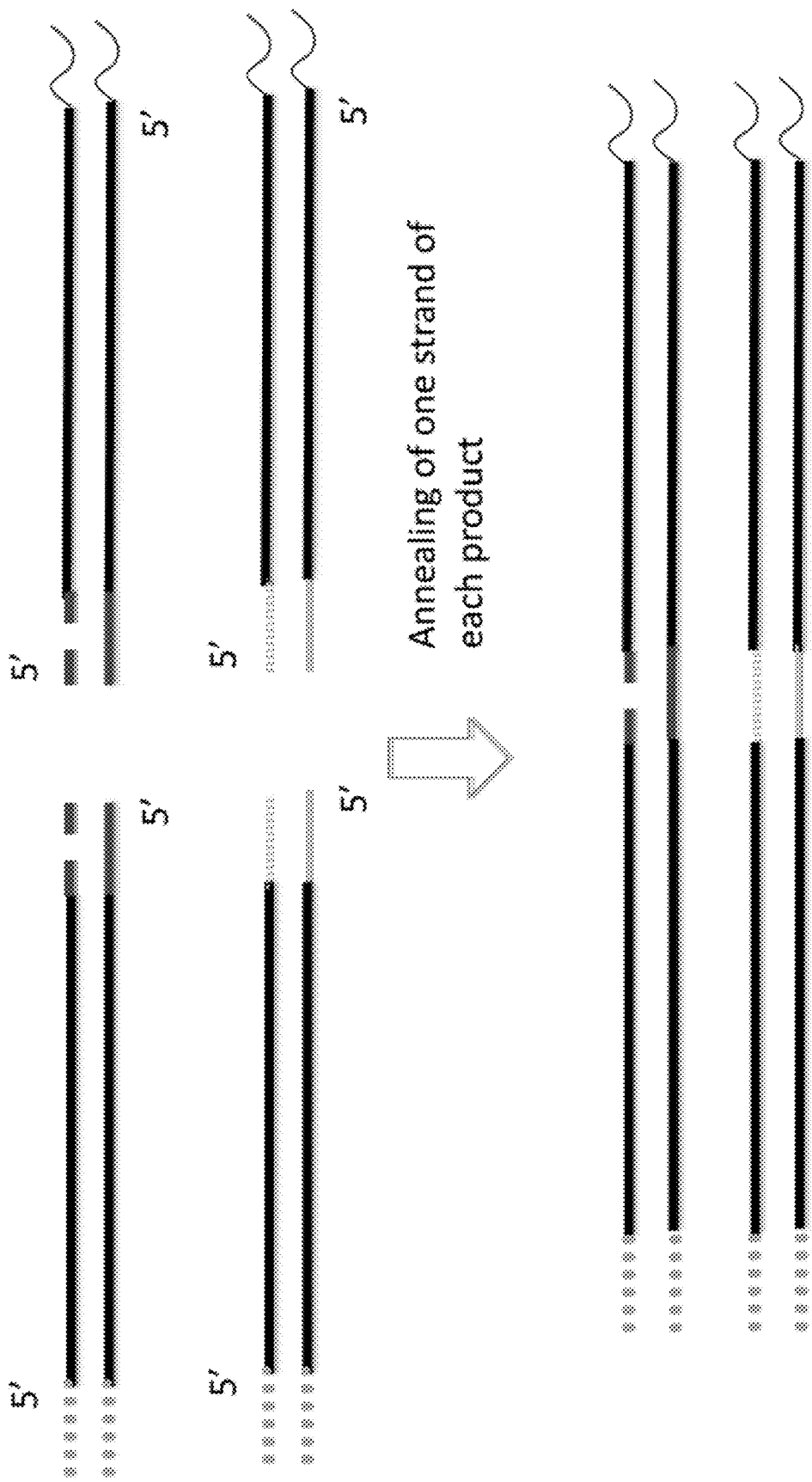

Linking 3 pieces

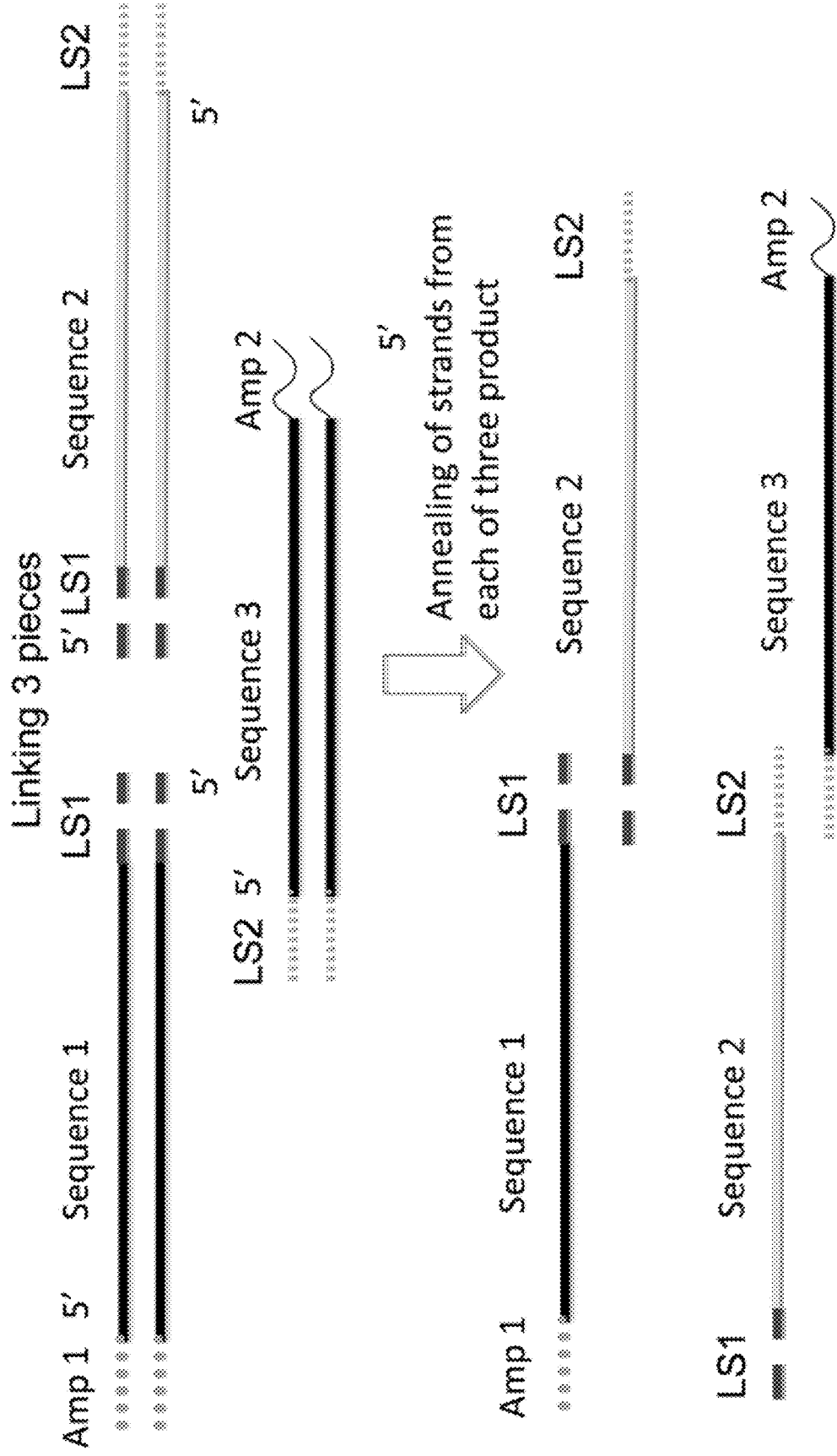

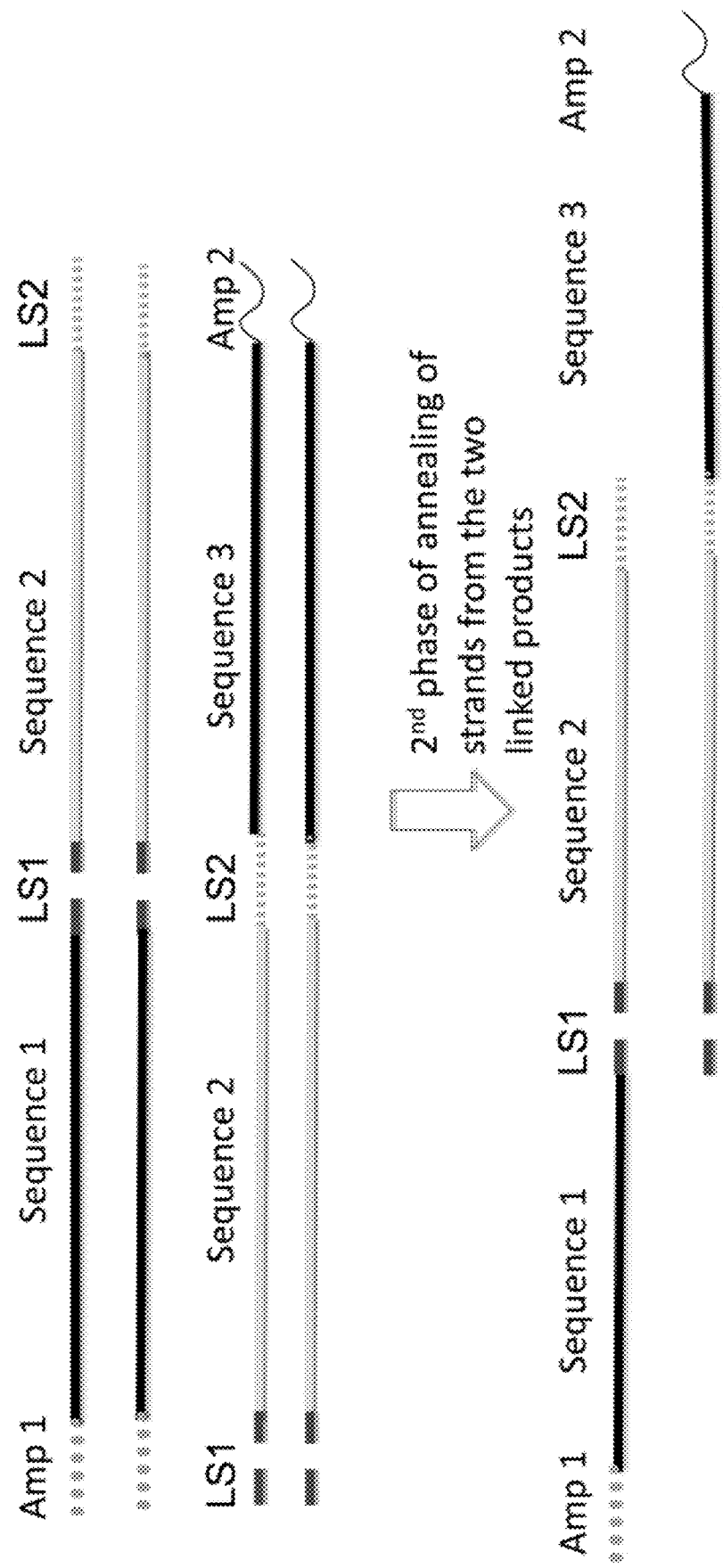

Linking 3 pieces

Monitoring Test without using a calibration test

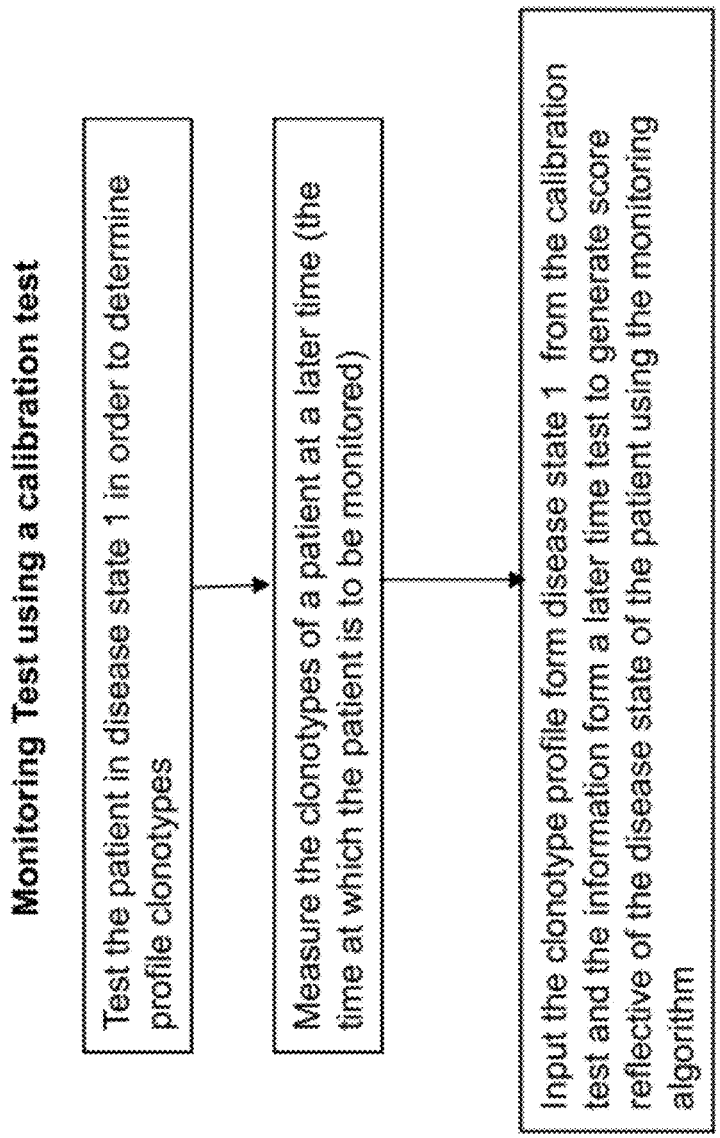

METHODS OF MONITORING CONDITIONS BY SEQUENCE ANALYSIS

CROSS REFERENCE

This application is a continuation application of co-pending U.S. utility application Ser. No. 13/459,701 filed 30 Apr. 2012, which is a continuation application of U.S. utility application Ser. No. 12/615,263 filed 9 Nov. 2009, now U.S. Pat. No. 8,236,503, which patent claims the benefit of U.S. provisional application Ser. No. 61/112,693 filed 7 Nov. 2008; each of the foregoing applications is incorporated by reference in its entirety.

SEQUENCE LISTING

The instant application contains a Sequence Listing which has been submitted via EFS-Web and is hereby incorporated by reference in its entirety. Said ASCII copy, created on Jul. 24, 2012, is named 37623-701-305Seqlist.txt, and is 31 Kilobytes in size.

BACKGROUND OF THE INVENTION

The immune system comprises the innate and the adaptive immunity systems. The innate immune system comprises the cells and mechanisms utilizing generic methods to recognize foreign pathogens. Cells involved in innate immunity include neutrophils, natural killer cells, macrophages, monocytes, basophils, eosinphils, mast, and dentritic cells. These cells carry out the act of phagocytosis as well as the release of many chemicals that kill invading pathogens. In addition, these cells are involved in innate immunity defense mechanisms including the complement cascade and inflammation. Finally, some of these cells participate in the antigen presentation process that plays a role in the adaptive immunity system.

The adaptive immunity system has evolved to attack specific features on their targets. The occurrence of one response to a specific target provides the host with "memory" of it, causing it to mount a stronger response if it were to appear another time. Usually any protein or polysaccharide can serve as the target for some subset of the adaptive immune response cells or their products that recognize specific epitopes on the target. The adaptive immune response is divided into two types: the humoral and the cell-mediated immune response, and B-cells and T-cells play the specificity roles in these responses, respectively.

Since autoimmune disease involves the recognition of some element of the adaptive immune system to self targets, aspects of the adaptive immune system have been examined to aid in diagnosis and prognosis. Using standard immunological techniques, the humoral immune system has been investigated by looking for circulating autoantibodies. Autoantibodies, like antinuclear, anti-dsDNA, and rheumatoid factor, have been identified for several diseases. These antibodies may not themselves be pathological, nor is the target they recognize in the body necessarily the same as that tested for in vitro; however, measurement of their levels aids in the diagnosis and in some cases has some prognostic and treatment implications.

Another methodology to study the adaptive immune system in autoimmune disease is based on the analysis of the diversity of the adaptive immune cells. Activation of the adaptive immune cells leads to their clonal expansion. Evidence of this clonal expansion is usually achieved by amplification from the blood RNA or DNA of part of the nucleic acid sequence coding for the antigen recognition region. For example, PCR primers to amplify sequences that have a specific V segment of the β chain in T-cell receptor (analogous to antibody heavy chain) are used to amplify the J segments or J and D segments connected to the specific V segment. When a diverse cell population is present it is expected to amplify fragments with a distribution of slightly different size amplicons, but clonal expansion causes specific sizes to become enriched and thus more intense as visualized as bands on a gel. In the technique called spectratyping each of the V segments is amplified with the J and D segments to assess whether any of these amplicons shows a clonal expansion.

One problem of the spectratyping approach is that many distinct sequences can have the same length and hence are indistinguishable. Therefore only dramatic clonal expansion can be discerned by this technique. There is need to improve methods of diagnosing and aiding prognosis of autoimmune disease and autoimmune disease states as well as other diseases for which the immune system plays a central role.

While additional specificity in profiling the immune system would be of great utility in allowing its impact on human health to be better predicted, still greater utility would be delivered if methods were developed that would allow the specific T and B cells involved in disease processes to be identified even if those particular sequences had never before been observed. The vast diversity of the immune system provides it with an immense reserve of potentially useful cells but also presents a challenge to the researcher trying to use this repertoire for predictive purposes. Any single sequence targeting an antigen is one of a vast number that could be involved with and/or correlated to the disease process in a given individual. Methods that would identify which of the many cells in a given individual are involved with disease processes would be of great value to human health.

SUMMARY OF THE INVENTION

In one aspect, a method for determining a profile of recombined DNA sequences in T-cells and/or B-cells is provided comprising: obtaining a sample from a subject comprising T-cells and/or B-cells, spatially isolating individual molecules of genomic DNA from said cells; sequencing said spatially isolated individual molecules of genomic DNA, and determining the levels of different sequences from said sample to generate said profile of recombined DNA sequences.

In another aspect, a method for determining a profile of recombined DNA sequences in T-cells and/or B-cells is provided comprising: obtaining a sample from a subject comprising T-cells and/or B-cells, spatially isolating individual molecules of genomic DNA from said cells, amplifying said individual molecules of genomic DNA, sequencing said amplified DNA, and determining the levels of different sequences from said sample to generate said profile of recombined DNA sequences.

In another aspect, a method for determining a profile of recombined DNA sequences in T-cells and/or B-cells is provided comprising: obtaining a sample from a subject comprising T-cells and/or B-cells, amplifying genomic DNA from said cells, spatially isolating individual molecules of said amplified DNA, sequencing said spatially isolated individual molecules of amplified DNA; and determining the levels of different sequences from said sample to generate said profile of recombined DNA sequences.

In another aspect, a method for determining a profile of recombined DNA sequences in T-cells and/or B-cells is provided comprising: obtaining a sample from a subject comprising T-cells and/or B-cells, amplifying genomic DNA from said cells, spatially isolating individual molecules of said amplified DNA, re-amplifying said amplified DNA molecules, sequencing said re-amplified DNA molecules, and determining the levels of different sequences from said sample to generate said profile of recombined DNA sequences.

In another aspect, a method for determining a profile of sequences of recombined DNA in T-cells and/or B-cells is provided comprising: obtaining a sample from a subject comprising T-cells and/or B-cells, reverse transcribing RNA from said cells to form cDNA, spatially isolating individual molecules of said cDNA, optionally re-amplifying said spatially isolated individual molecules of cDNA, sequencing said cDNA and/or re-amplified cDNA; and determining the levels of different sequences from said sample to generate said profile of recombined DNA sequences.

In another aspect, a method for determining a profile of recombined DNA sequences in T-cells and/or B-cells is provided comprising: obtaining a sample from a subject comprising T-cells and/or B-cells; spatially isolating individual cells in said sample, sequencing individual molecules of nucleic from said cells; and determining the levels of different sequences from said sample to generate said profile of recombined DNA sequences.

In one embodiment, said amplifying and/or re-amplifying comprises PCR, multiplex PCR, TMA, NASBA, or LAMP. In another embodiment, said spatially isolating comprises subcloning said DNA or cDNA in vectors used to transform bacteria, separating said DNA or cDNA in two dimensions on a solid support, separating said DNA or cDNA in three dimensions in a solution with micelles, or separating molecules using micro-reaction chambers. In another embodiment, said amplifying and/or re-amplifying is by growth of bacteria harboring subcloned DNA or cDNA, amplification of DNA or cDNA on a slide, or amplification of DNA or cDNA on a bead.

In another embodiment, said sequencing comprises dideoxy sequencing. In another embodiment, said sequencing comprises sequencing by synthesis using reversibly terminated labeled nucleotides. In another embodiment, said sequencing comprises detection of pyrophosphate release on nucleotide incorporation. In another embodiment, said sequencing comprises allele specific hybridization to a library of labeled oligonucleotide probes. In another embodiment, said sequencing comprises sequencing by synthesis using allele specific hybridization to a library of labeled oligonucleotide probes followed by ligation of said probes. In another embodiment, said sequencing comprises real time monitoring of the incorporation of labeled nucleotides during a polymerization step.

In another embodiment, said recombined DNA sequences comprise T-cell receptor genes and/or immunoglobulin genes. In another embodiment, said sequencing comprises sequencing a subset of the full clonal sequences of immunoglobulin and/or T-cell receptor genes.

In another embodiment, said subset of the full clonal sequence comprises the V-D junction, D-J junction of an immunoglobulin or T-cell receptor gene, the full variable region of an immunoglobulin or T-cell receptor gene, the antigen recognition region, or the complementarity determining region 3 (CDR3). In another embodiment, said T-cell receptor genes comprise T-cell receptor $\beta$ genes. In another embodiment, said immunoglobulin genes comprise immunoglobulin heavy genes. In another embodiment, said amplifying or re-amplifying comprises a plurality of primers complementary to V segments and one primer complementary to a C segment. In another embodiment, said amplifying or re-amplifying comprises a plurality of primers complementary to V segments and a plurality of primers complementary to C segments.

In another embodiment, said plurality of primers complementary to V segments comprises at least three different primers for each V segment and the plurality of primers complementary to C segments comprises at least 1, at least 2, at least 3, at least 4, at least 5, or at least 6 primers.

In another embodiment, said T- or B-cells are subsets of the total T and B cells. In another embodiment, said subset of T-cells are CD4+, CD8+ cells, or CD27$^{high}$ cells. In another embodiment, said sample comprises at least 100,000, at least 500,000, at least 750,000, of at least 1,000,000 T-cells.

In another embodiment, said sequencing comprises at least 1000 reads per run, at least 10,000 reads per run, at least 100,000 reads per run, or at least 1,000,000 reads per run. In another embodiment, said sequencing comprises generating about 30 bp, about 40 bp, about 50 bp, about 60 bp, about 70 bp, about 80 bp, about 90 bp, about 100 bp, about 110, or about 120 bp per read.

In another embodiment, said sample is taken when the subject is at a flare state of an autoimmune disease. In another embodiment, said sample is taken from a subject having or suspected of having systemic lupus erythematosus.

In another aspect, a method for determining one or more correlating clonotypes in a subject is provided comprising: generating one or more clonotype profiles by nucleic acid sequencing individual, spatially isolated molecules from at least one sample from the subject, wherein the at least one sample is related to a first state of the disease, and determining one or more correlating clonotypes in the subject based on the one or more clonotype profiles.

In one embodiment, said at least one sample is from a tissue affected by the disease. In another embodiment, said determination of one or more correlating clonotypes comprises comparing clonotype profiles from at least two samples.

In another embodiment, the first state of the disease is a peak state of the disease. In another embodiment, said one or more correlating clonotypes are present in the peak state of the disease. In another embodiment, said one or more correlating clonotypes are absent in the peak state of the disease. In another embodiment, said one or more correlating clonotypes are high in the peak state of the disease. In another embodiment, said one or more correlating clonotypes are low in the peak state of the disease.

In another embodiment, said sample comprises T-cells and/or B-cells. In another embodiment, said T-cells and/or B-cells comprise a subset of T-cells and/or B-cells. In another embodiment, said subset of T-cells and/or B-cells are enriched by interaction with a marker. In another embodiment, said marker is a cell surface marker on the subset of T-cells and/or B-cells. In another embodiment, said subset of T-cells and/or B-cells interact with an antigen specifically present in the disease.

In another embodiment, the disease is systemic lupus erythematosus or multiple sclerosis.

In another aspect, a method for developing an algorithm that can predict one or more correlating clonotypes in any sample from a subject with a disease is provided comprising: a) generating a plurality of clonotype profiles from a set of samples, wherein the samples are relevant to the disease, b) identifying one or more correlating clonotypes from the set of samples, c) using sequence parameters and/or functional data from one or more correlating clonotypes identified in b) to develop the algorithm that can predict correlating clonotypes in any sample from a subject with the disease.

In one embodiment, the set of samples are taken from one or more tissues affected by the disease.

In another embodiment, said identification of one or more correlating clonotypes comprises comparing clonotype profiles from at least two samples.

In another embodiment, said functional data include binding ability of markers on T-cell and/or B-cell surface or interaction with antigen by a T-cell or B-cell.

In another embodiment, said sequence parameters comprise nucleic acid sequence and predicted amino acid sequence.

In another embodiment, the samples are from one or more individuals at a peak stage of the disease. In another embodiment, said one or more correlating clonotypes are present in the peak state of the disease. In another embodiment, said one or more correlating clonotypes are at a high level in the peak state of the disease. In another embodiment, said one or more correlating clonotypes are at a low level in the peak state of the disease. In another embodiment, the one or more correlating clonotypes are absent at the peak state of the disease. In another embodiment, the disease is systemic lupus erythematosus or multiple sclerosis.

In another embodiment, a method for discovering one or more correlating clonotypes for an individual is provided, comprising inputting a clonotype profile from a sample from the individual into an algorithm, and using the algorithm to determine one or more correlating clonotypes for the individual. In one embodiment, the algorithm is an algorithm that can predict one or more correlating clonotypes in any sample from a subject with a disease is provided comprising, said algorithm being developed by: a) generating a plurality of clonotype profiles from a set of samples, wherein the samples are relevant to the disease, b) identifying one or more correlating clonotypes from the set of samples, c) using sequence parameters and/or functional data from one or more correlating clonotypes identified in b) to develop an algorithm that can predict correlating clonotypes in any sample from a subject with the disease.

In one embodiment, said sample is at taken at a peak state of disease. In another embodiment, the sample is taken from disease affected tissue.

In another aspect, a method for generating an algorithm that calculates a disease activity score is provided comprising: developing an algorithm that uses a set of factors to combine levels of correlating clonotypes into a disease activity score, comparing the disease activity score to clinical data regarding the disease state, and optimizing the factors in order to maximize the correlation between clinical data and the disease activity score.

In one embodiment, method for monitoring the disease state of an individual is provided comprising: a) determining a clonotype profile from a sample from the individual, b) inputting the clonotype profile information from a) into an algorithm that calculates a disease activity score, wherein is algorithm is generated by developing an algorithm that uses a set of factors to combine levels of correlating clonotypes into a disease activity score, comparing the disease activity score to clinical data regarding the disease state, and optimizing the factors in order to maximize the correlation between clinical data and the disease activity score, and c) using the algorithm that calculates a disease activity score to generate a score predictive of the disease state of the individual.

In another embodiment, the method for monitoring the disease state of an individual further comprises determining one or more correlating clonotypes in the individual, and inputting information the one or more correlating clonotypes into the algorithm.

In another embodiment, said determining one or more correlating clonotypes in the individual comprises a) generating one or more clonotype profiles by nucleic acid sequencing individual, spatially isolated molecules from at least one sample from the subject, wherein the at least one sample is related to a first state of the disease, and b) determining one or more correlating clonotypes in the subject based on the one or more clonotype profiles.

In another embodiment, said determining one or more correlating clonotypes in the individual comprises a) inputting a clonotype profile from a sample from the individual into an algorithm that can predict one or more correlating clonotypes, wherein said algorithm that can predict one or more correlating clonotypes is developed by i) generating a plurality of clonotype profiles from a set of samples, wherein the samples are relevant to the disease, ii) identifying one or more correlating clonotypes from the set of samples, iii) using sequence parameters and/or functional data from one or more correlating clonotypes identified in ii) to develop the algorithm that can predict correlating clonotypes in any sample from a subject with the disease, and c) using the algorithm that can predict one or more correlating clonotypes to determine one or more correlating clonotypes for the individual.

In another embodiment, the disease is systemic lupus erythematosus or multiple sclerosis.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A discloses SEQ ID NOS 130 and 130-131, respectively, in order of appearance. FIG. 2B is a schematic representation of primers that may be useful in the primary and secondary PCR in accordance with one aspect of the invention.

FIGS. 4A and 4B illustrate a PCR scheme for amplifying isotype sequences. FIG. 4A discloses SEQ ID NOS 132, 132, 132 and 132-134, respectively, in order of appearance.

illustrates a flow diagram for determining the algorithm by a discovery study.

FIG. 9 illustrates one embodiment of a scheme for linking two sequences to form one amplicon during an amplification reaction. Information on the presence of these two sequences in the same sample (e.g., cell) can then be preserved even if they are mixed with a pool of sequences from other samples.

FIG. 10 illustrates another embodiment of an amplification scheme for linking two sequences.

FIG. 11 illustrates another embodiment of an amplification scheme for linking two sequences.

FIGS. 12A and 12B illustrate a scheme for multiplexing the a reaction linking two sequences by PCR.

FIGS. 13A-13D illustrate a scheme for linking three sequences together.

Figure 14:
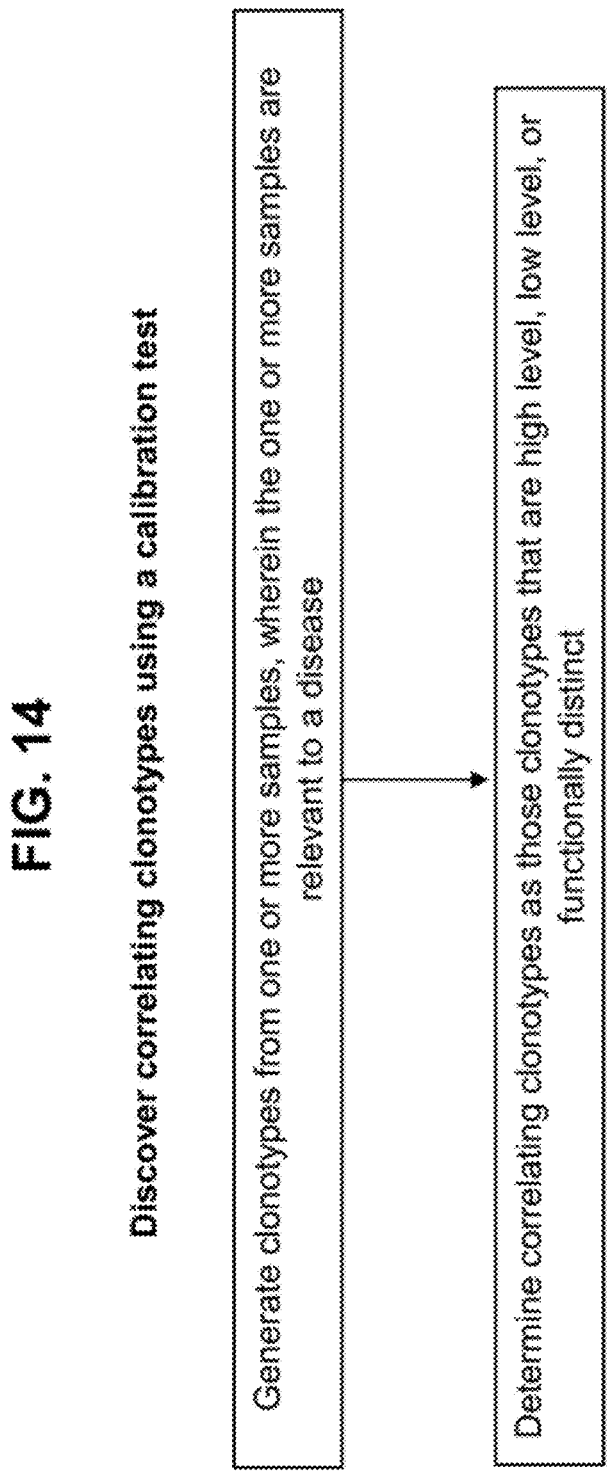

FIG. 14 illustrates a flow diagram for discovering correlating clonotypes using a calibration test.

Figure 15:
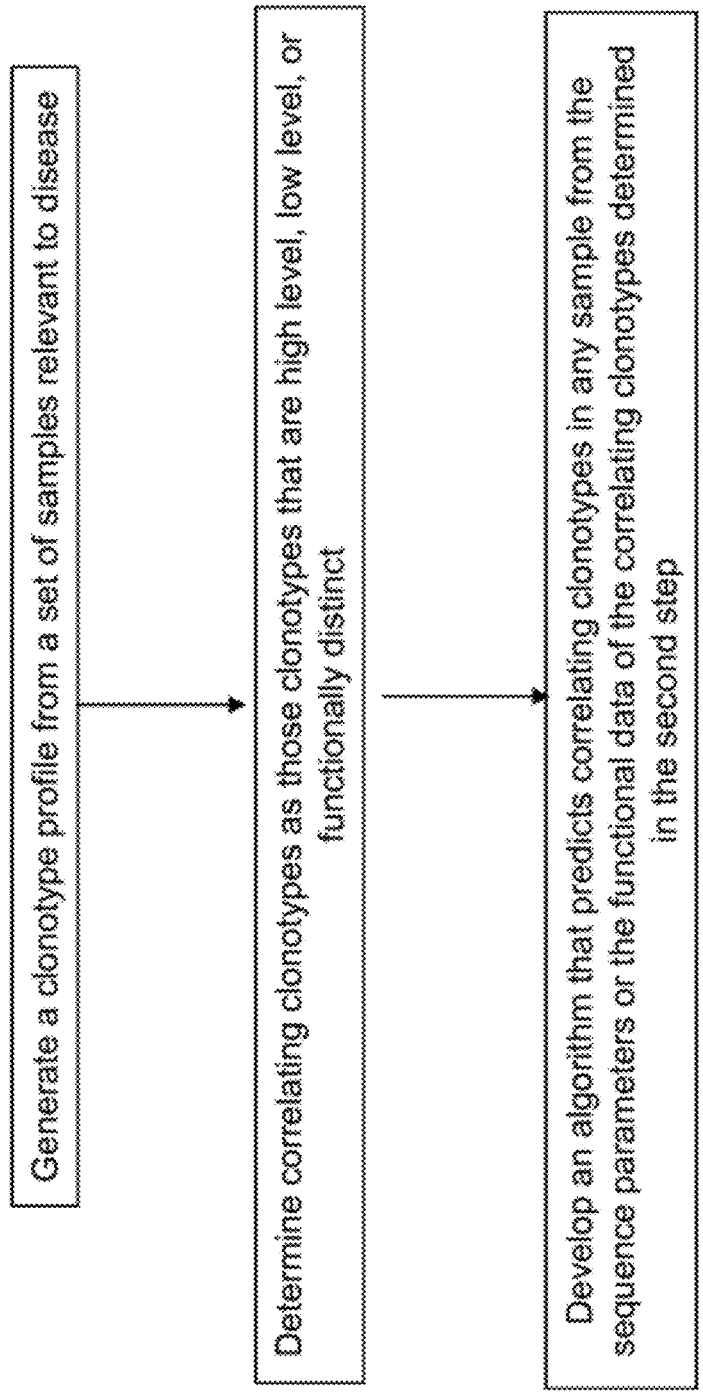

FIG. 15 illustrates a flow diagram for discovering correlating clonotypes using a population study.

Figure 16:
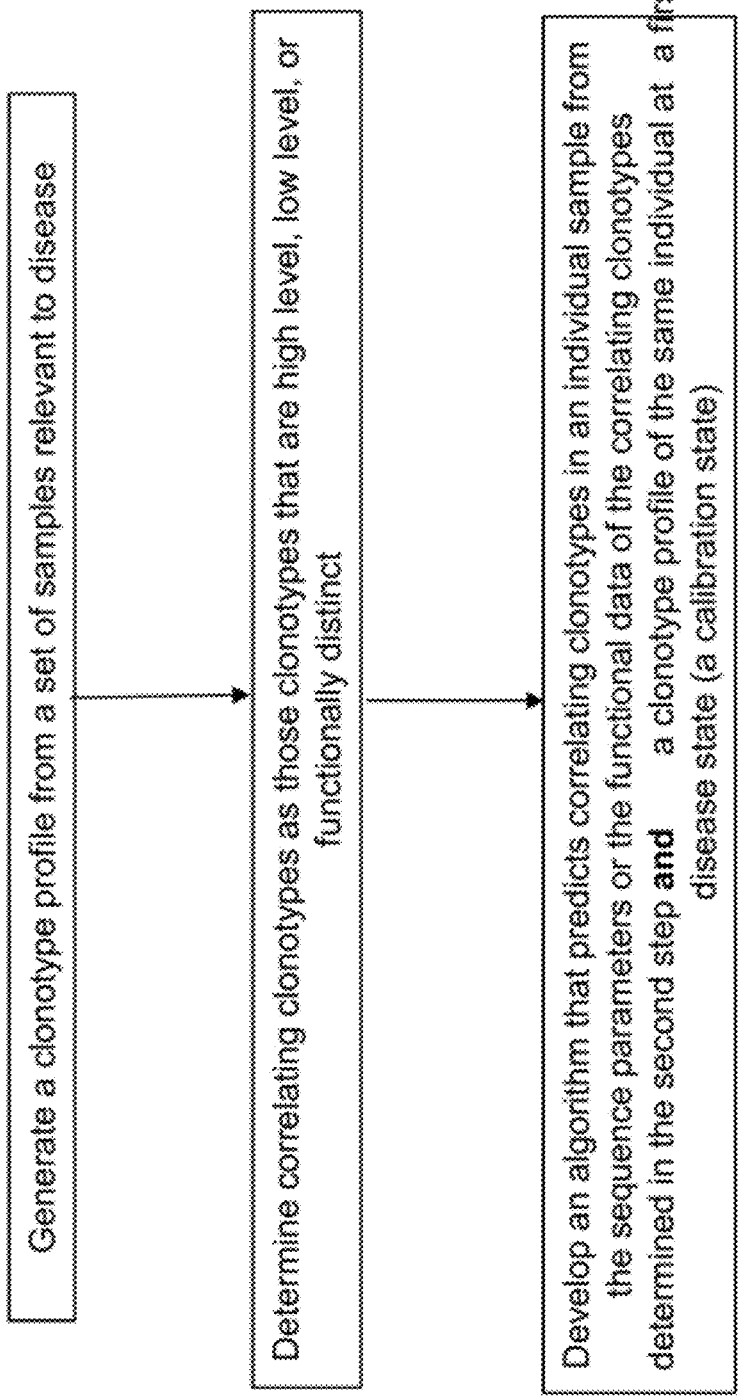

FIG. 16 illustrates a flow diagram for discovering correlating clonotypes using a population study and a calibration test.

Figure 17:
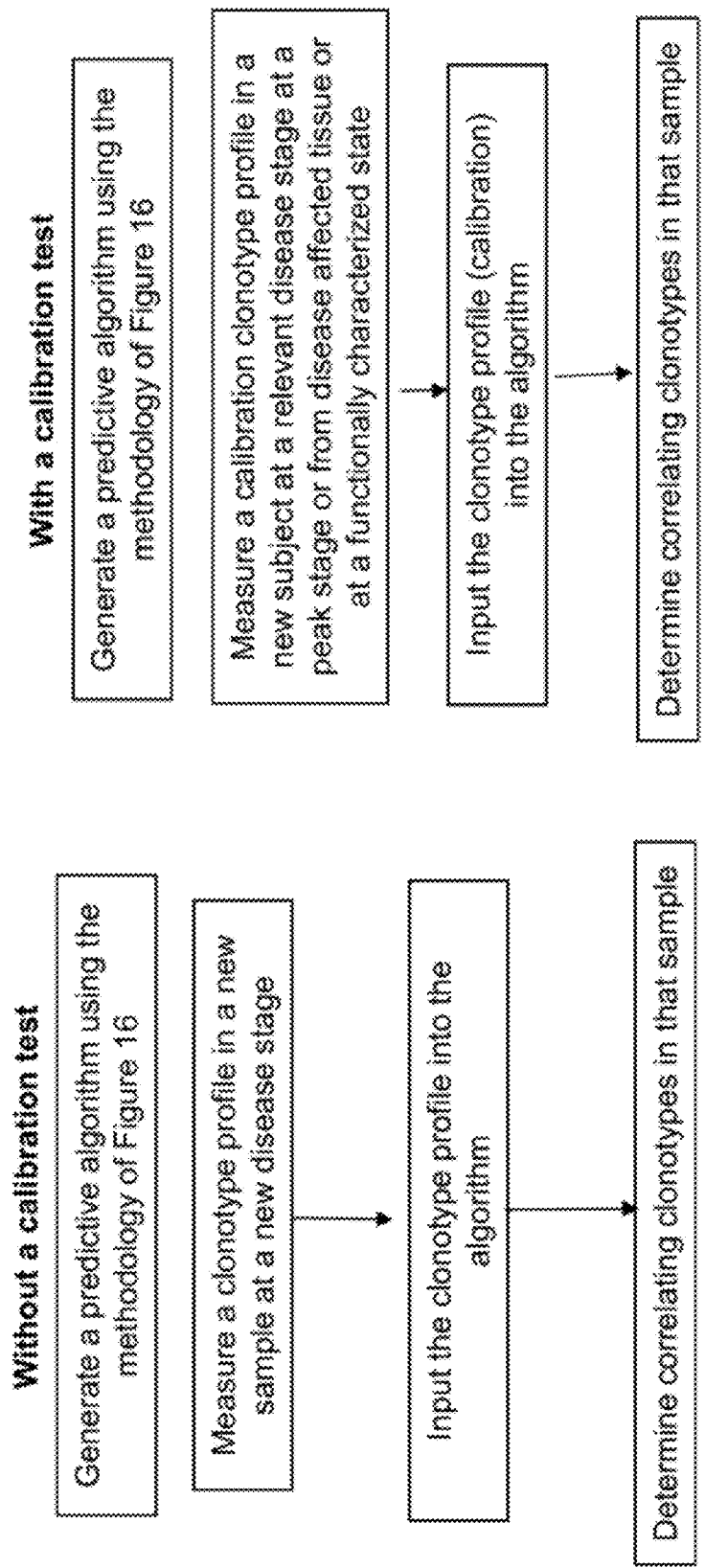

FIG. 17 illustrates algorithms that can predict correlating clonotypes in a sample.

Figure 18:
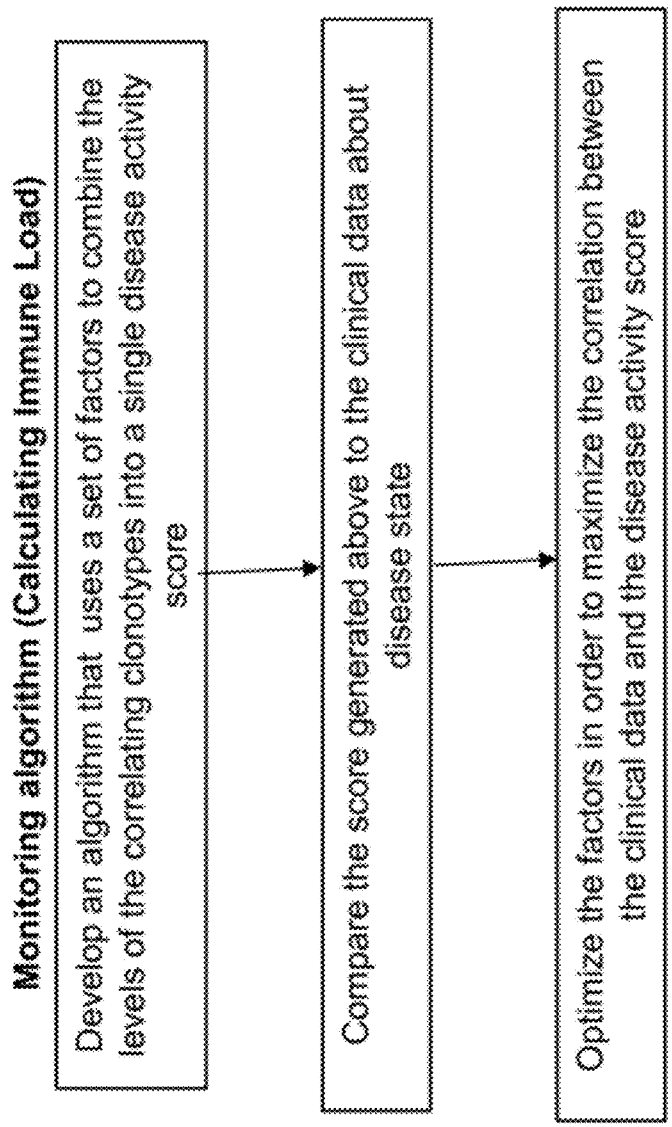

FIG. 18 illustrates a flow diagram for generating a monitoring algorithm for calculating Immune Load.

Figure 19:
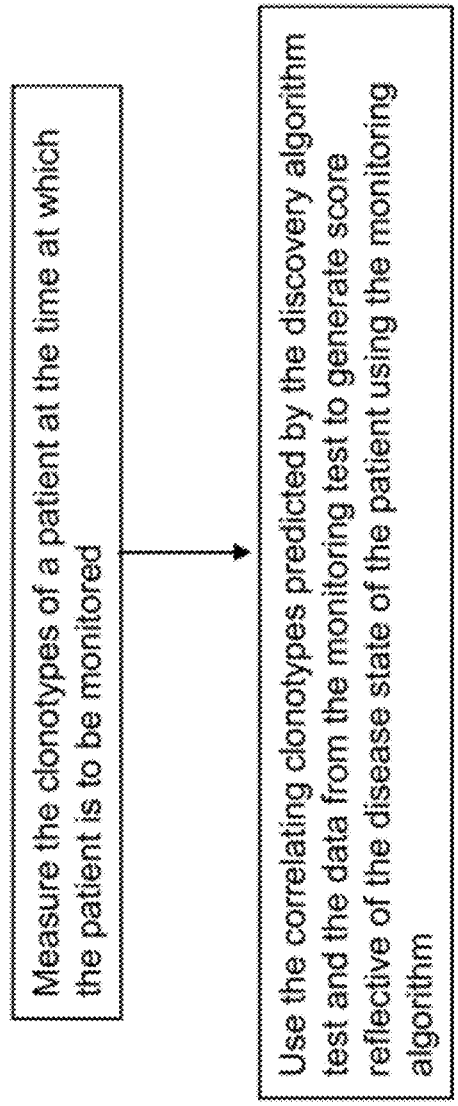

FIG. 19 illustrates a flow diagram for performing a monitoring test without a calibration test.

FIG. 20 illustrates a flow diagram for performing a monitoring test using a calibration test.

DETAILED DESCRIPTION OF THE INVENTION

Overview

In general, the provided invention includes methods for applying nucleic acid sequencing techniques to the task of monitoring the repertoire of adaptive immunity cells for profiling the immune system. The profiles of the immune system generated can be used for diagnosis of diseases and disorders, and for diagnosis of states of diseases and disorders. The methods of immune profiling of the provided invention can be used in monitoring diseases and disorders and assessing treatment of diseases and disorders. These diseases and disorders that the methods of the provided invention can be applied to include autoimmune disease, including systemic lupus erythematosus (SLE), multiple sclerosis (MS), rheumatoid arthritis (RA), and ankylosing spondylitis. The methods of the provided invention can be applied to the diagnosis, monitoring, and treatment of transplant rejection and immune aging. Furthermore, the methods of immune profiling of the provided invention can be used for diagnosing, monitoring, and treating other diseases related to the immune system, including cancer and infectious disease.

Sequencing individual amplified molecules can distinguish different sequences and hence has the sensitivity to detect quantitative changes in clonal expansion. In general, in one embodiment of the provided invention, a method for determining a profile of recombined DNA sequences in T-cells and/or B-cells is provided. The method can comprise steps including isolating samples from a subject, one or more rounds of nucleic acid amplification, spatially isolating individual nucleic acids, and sequencing nucleic acids. The nucleic acids can be DNA or RNA. The recombined DNA sequences in T-cells and/or B-cells can be termed clonotypes.

In one aspect, a method for determining one or more correlating clonotypes in a subject or individual is provided. In another aspect, a method for developing an algorithm that can predict one or more correlating clonotypes in any sample from a subject with a disease is provided. In another aspect, a method for discovering one or more correlating clonotypes for an individual using an algorithm that can predict one or more correlating clonotypes in any sample from a subject is provided. In another aspect, a method for generating an algorithm that calculates a disease activity score is provided. In another aspect, a method for monitoring the disease state of an individual is provided.

I. Methods of Determining Clonotype Profiles

A. Overview

The methods of the provided invention can be used to generate profiles of recombined DNA sequences, or clonotypes, in sample from a subject.

In one embodiment, a method for determining a profile of recombined DNA sequences in T-cells and/or B-cells is provided including obtaining a sample from a subject comprising T-cells and/or B-cells, isolating individual molecules of genomic DNA from said cells, sequencing the isolated individual molecules of genomic DNA, and determining the levels of different sequences from the sample to generate said profile of recombined DNA sequences.

In another embodiment, a method for determining a profile of recombined DNA sequences in T-cells and/or B-cells is provided including obtaining a sample from a subject comprising T-cells and/or B-cells, isolating individual molecules of genomic DNA from the cells, amplifying the individual molecules of genomic DNA, sequencing the amplified DNA, and determining the levels of different sequences from the sample to generate said profile of recombined DNA sequences.

In another embodiment, a method for determining a profile of recombined DNA sequences in T-cells and/or B-cells is provided including obtaining a sample from a subject comprising T-cells and/or B-cells, amplifying genomic DNA from the cells, isolating individual molecules of the amplified DNA, sequencing the isolated individual molecules of amplified DNA, and determining the levels of different sequences from the sample to generate the profile of recombined DNA sequences.

In another embodiment, a method for determining a profile of recombined DNA sequences in T-cells and/or B-cells is provided including obtaining a sample from a subject including T-cells and/or B-cells, amplifying genomic DNA from the cells, isolating individual molecules of the amplified DNA, re-amplifying the amplified DNA molecules, sequencing the re-amplified DNA molecules, and determining the levels of different sequences from the sample to generate the profile of recombined DNA sequences.

In another embodiment, a method for determining a profile of sequences of recombined DNA in T-cells and/or B-cells is provided including obtaining a sample from a subject comprising T-cells and/or B-cells, isolating RNA from said sample, reverse transcribing the RNA from said cells to form cDNA, isolating individual molecules of said cDNA, optionally re-amplifying said cDNA, sequencing said isolated individual molecules of said cDNA or re-amplified DNA, and determining the levels of different sequences from said sample to generate said profile of recombined DNA sequences.

In another embodiment, a method for determining a profile of sequences of recombined DNA in T-cells and/or B-cells is provided including obtaining a sample from a subject including T-cells and/or B-cells, isolating individual molecules of RNA from said sample, sequencing the individual molecules of RNA, and determining the levels of different sequences from said sample to generate the profile of recombined DNA sequences.

B. Subjects and Samples

1. Subjects

The methods of the provided invention can use samples from subjects or individuals (e.g., patients). The subject can be a patient, for example, a patient with an autoimmune disease. The subject can be a patient with an infectious disease or cancer. The subject can be a mammal, for example, a human. The subject can be male or female. The subject can be an infant, a child, or an adult.

2. Samples

Samples used in the methods of the provided invention can include, for example, a bodily fluid from a subject, including amniotic fluid surrounding a fetus, aqueous humor, bile, blood and blood plasma, cerumen (earwax), Cowper's fluid or pre-ejaculatory fluid, chyle, chyme, female ejaculate, interstitial fluid, lymph, menses, breast milk, mucus (including snot and phlegm), pleural fluid, pus, saliva, sebum (skin oil), semen, serum, sweat, tears, urine, vaginal lubrication, vomit, water, feces, internal body fluids, including cerebrospinal fluid surrounding the brain and the spinal cord, synovial fluid surrounding bone joints, intracellular fluid is the fluid inside cells, and vitreous humour the fluids in the eyeball. In one embodiment, the sample is a blood sample. The blood sample can be about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 mL. The sample can be Cerebral Spinal Fluid (CSF) when the subject has multiple sclerosis, synovial fluid when the subject has rheumatoid arthritis, and skin (or other organ) biopsy when the subject has systemic lupus. In one embodiment, the clonotpe can be identified from the available body fluid/tissue most likely to reflect pathology followed by later monitoring the levels of the clonotypes form a different body fluid, for example, blood.

Samples can be analyzed at a time when the disease is inactive.

The sample can be obtained by a health care provider, for example, a physician, physician assistant, nurse, veterinarian, dermatologist, rheumatologist, dentist, paramedic, or surgeon. The sample can be obtained by a research technician. More than one sample from a subject can be obtained.

The sample can be a biopsy, e.g., a skin biopsy. The biopsy can be from, for example, brain, liver, lung, heart, colon, kidney, or bone marrow. Any biopsy technique used by those skilled in the art can be used for isolating a sample from a subject. For example, a biopsy can be an open biopsy, in which general anesthesia is used. The biopsy can be a closed biopsy, in which a smaller cut is made than in an open biopsy. The biopsy can be a core or incisional biopsy, in which part of the tissue is removed. The biopsy can be an excisional biopsy, in which attempts to remove an entire lesion are made. The biopsy can be a fine needle aspiration biopsy, in which a sample of tissue or fluid is removed with a needle.

The sample can include immune cells. The immune cells can include T-cells and/or B-cells. T-cells (T lymphocytes) include, for example, cells that express T cell receptors. T-cells include Helper T cells (effector T cells or Th cells), cytotoxic T cells (CTLs), memory T cells, and regulatory T cells. The sample can include a single cell in some applications (e.g., a calibration test to define relevant T cells) or more generally at least 1,000, at least 10,000, at least 100,000, at least 250,000, at least 500,000, at least 750,000, or at least 1,000,000 T-cells.

B-cells include, for example, plasma B cells, memory B cells, B1 cells, B2 cells, marginal-zone B cells, and follicular B cells. B-cells can express immunoglobulins (antibodies, B cell receptor). The sample can include a single cell in some applications (e.g., a calibration test to define relevant B cells) or more generally at least 1,000, at least 10,000, at least 100,000, at least 250,000, at least 500,000, at least 750,000, or at least 1,000,000 B-cells.

The sample can include nucleic acid, for example, DNA (e.g., genomic DNA or mitochondrial DNA) or RNA (e.g., messenger RNA or microRNA). The nucleic acid can be cell-free DNA or RNA. In the methods of the provided invention, the amount of RNA or DNA from a subject that can be analyzed includes, for example as low as a single cell in some applications (e.g., a calibration test) and as many as 10 millions of cells or more translating to a range of DNA of 6 pg-60 ug, and RNA of approximately 1 pg-10 ug.

C. Means for Isolating, Amplifying and Re-Amplifying Nucleic Acid

1. Characteristics of TCR and BCR Genes

Since the identifying recombinations are present in the DNA of each individual adaptive immunity cell as well as their associated RNA transcripts, either RNA or DNA can be sequenced in the methods of the provided invention. A recombined sequence from a T-cell or B-cell can also be referred to as a clonotype. The DNA or RNA can correspond to sequences from T-cell receptor (TCR) genes or immunoglobulin (Ig) genes that encode antibodies. For example, the DNA and RNA can correspond to sequences encoding $\alpha$, $\beta$, $\gamma$, or $\delta$ chains of a TCR. In a majority of T-cells, the TCR is a heterodimer consisting of an $\alpha$-chain and $\beta$-chain. The TCR$\alpha$ chain is generated by VJ recombination, and the $\beta$ chain receptor is generated by V(D)J recombination. For the TCR$\beta$ chain, in humans there are 48 V segments, 2 D segments, and 13 J segments. Several bases may be deleted and others added (called N and P nucleotides) at each of the two junctions. In a minority of T-cells, the TCRs consist of $\gamma$ and $\delta$ delta chains. The TCR $\gamma$ chain is generated by VJ recombination, and the TCR $\delta$ chain is generated by V(D)J recombination (Kenneth Murphy, Paul Travers, and Mark Walport, *Janeway's Immunology* 7th edition, Garland Science, 2007, which is herein incorporated by reference in its entirety.

The DNA and RNA analyzed in the methods of the provided invention can correspond to sequences encoding heavy chain immunoglobulins (IgH) with constant regions ($\alpha$, $\delta$, $\epsilon$, $\gamma$, or $\mu$) light chain immunoglobulins (IgK or IgL) with constant regions $\lambda$ or $\kappa$. Each antibody has two identical light chains and two identical heavy chains. Each chain is composed of a constant (C) and a variable region. For the heavy chain, the variable region is composed of a variable (V), diversity (D), and joining (J) segments. Several distinct sequences coding for each type of these segments are present in the genome. A specific VDJ recombination event occurs during the development of a B-cell, marking that cell to generate a specific heavy chain. Diversity in the light chain is generated in a similar fashion except that there is no D region so there is only VJ recombination. Somatic mutation often occurs close to the site of the recombination, causing the addition or deletion of several nucleotides, further increasing the diversity of heavy and light chains generated by B-cells. The possible diversity of the antibodies generated by a B-cell is then the product of the different heavy and light chains. The variable regions of the heavy and light chains contribute to form the antigen recognition (or binding) region or site.

Added to this diversity is a process of somatic hypermutation which can occur after a specific response is mounted against some epitope. In this process mutations occur in those B-cells that are able to recognize the specific epitope leading to greater diversity in antibodies that may be able to bind the specific epitope more strongly. All these factors contribute to great diversity of antibodies generated by the B-cells. Many billions and maybe more than a trillion distinct antibodies may be generated. The basic premise for generating T-cell diversity is similar to that for generating antibodies by B-cells. An element of T-cell and B-cell activation is their binding to foreign epitopes. The activation of a specific cell leads to the production of more of the same type of cells leading to a clonal expansion.

Complementarity determining regions (CDR), or hypervariable regions, are sequences in the variable domains of antigen receptors (e.g., T cell receptor and immunoglobulin) that can complement an antigen. The chain of each antigen receptor contains three CDRs (CDR1, CDR2, and CDR3). The two polypeptides making T cells ($\alpha$ and $\beta$) and immunoglobulin (IgH and IgK or IgL) contribute to the formation of the three CDRs.

The part of CDR1 and CDR2 that is coded for by TCR$\beta$ lies within one of 47 functional V segments. Most of the diversity of CDRs is found in CDR3, with the diversity being generated by somatic recombination events during the development of T lymphocytes.

A great diversity of BCR is present inter and intra-individuals. The BCR is composed of two genes IgH and IgK (or IgL) coding for antibody heavy and light chains. Three Complementarity Determining Region (CDR) sequences that bind antigens and MHC molecules have the most diversity in IgH and IgK (or IgL). The part of CDR1 and CDR2 coded for by IgH lies within one of 44 functional V segments. Most of the diversity in naïve B cells emerges in the generation of CDR3 through somatic recombination events during the development of B lymphocytes. The recombination can generate a molecule with one of each of the V, D, and J segments. In humans, there are 44 V, 27 D, and 6 J segments; thus, there is a theoretical possibility of more than 7,000 combinations. In a small fraction of BCRs (~5%) two D segments are found. Furthermore, several bases may be deleted and others added (called N and P nucleotides) at each of the two junctions generating a great degree of diversity. After B cell activation a process of affinity maturation through somatic hypermutation occurs. In this process progeny cells of the activated B cells accumulate distinct somatic mutations throughout the gene with higher mutation concentration in the CDR regions leading to generating antibodies with higher affinity to the antigens. Therefore multiple primers can be utilized to amplify sequences after somatic hypermutation. In addition to somatic hypermutation activated B cells undergo the process of isotype switching Antibodies with the same variable segments can have different forms (isotypes) depending on the constant segment. Whereas all naïve B cells express IgM (or IgD), activated B cells mostly express IgG but also IgM, IgA and IgE. This expression switching from IgM (and/or IgD) to IgG, IgA, or IgE occurs through a recombination event causing one cell to specialize in producing a specific isotype. There is one segment for each IgM, IgD, and IgE, two segments for IgA, and four segments for IgG.

2. Amplification Reactions

Polymerase chain reaction (PCR) can be used to amplify the relevant regions from a collection of cells. Transcription Mediated Amplification (TMA) can be used to produce RNA amplicons from a target nucleic acid. The nucleic acid from each cell can be analyzed separately, as each cell will carry its own unique signature.

Figure 2:
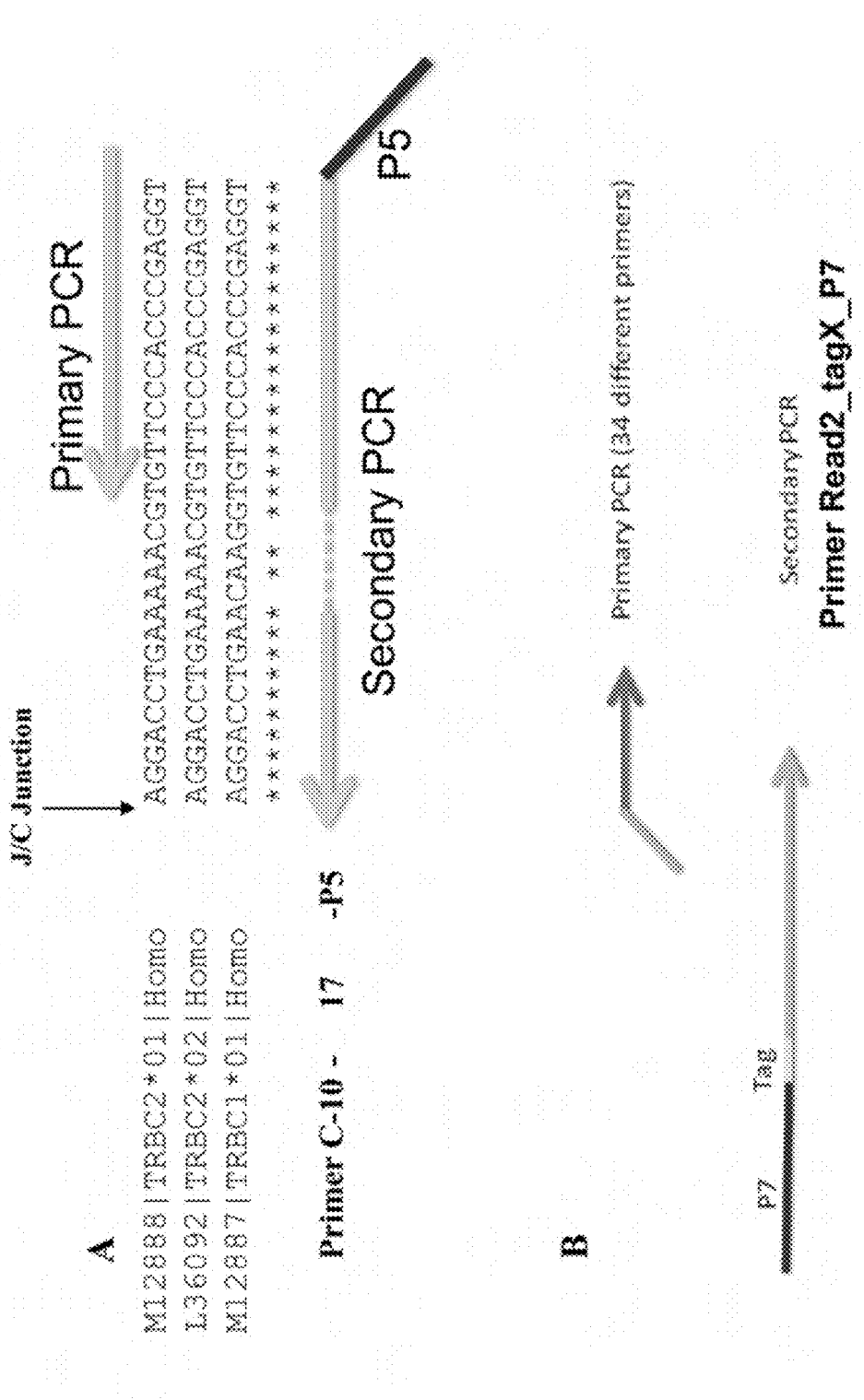
FIG. 2 shows a PCR scheme for amplifying TCRβ genes.
Figure 4:
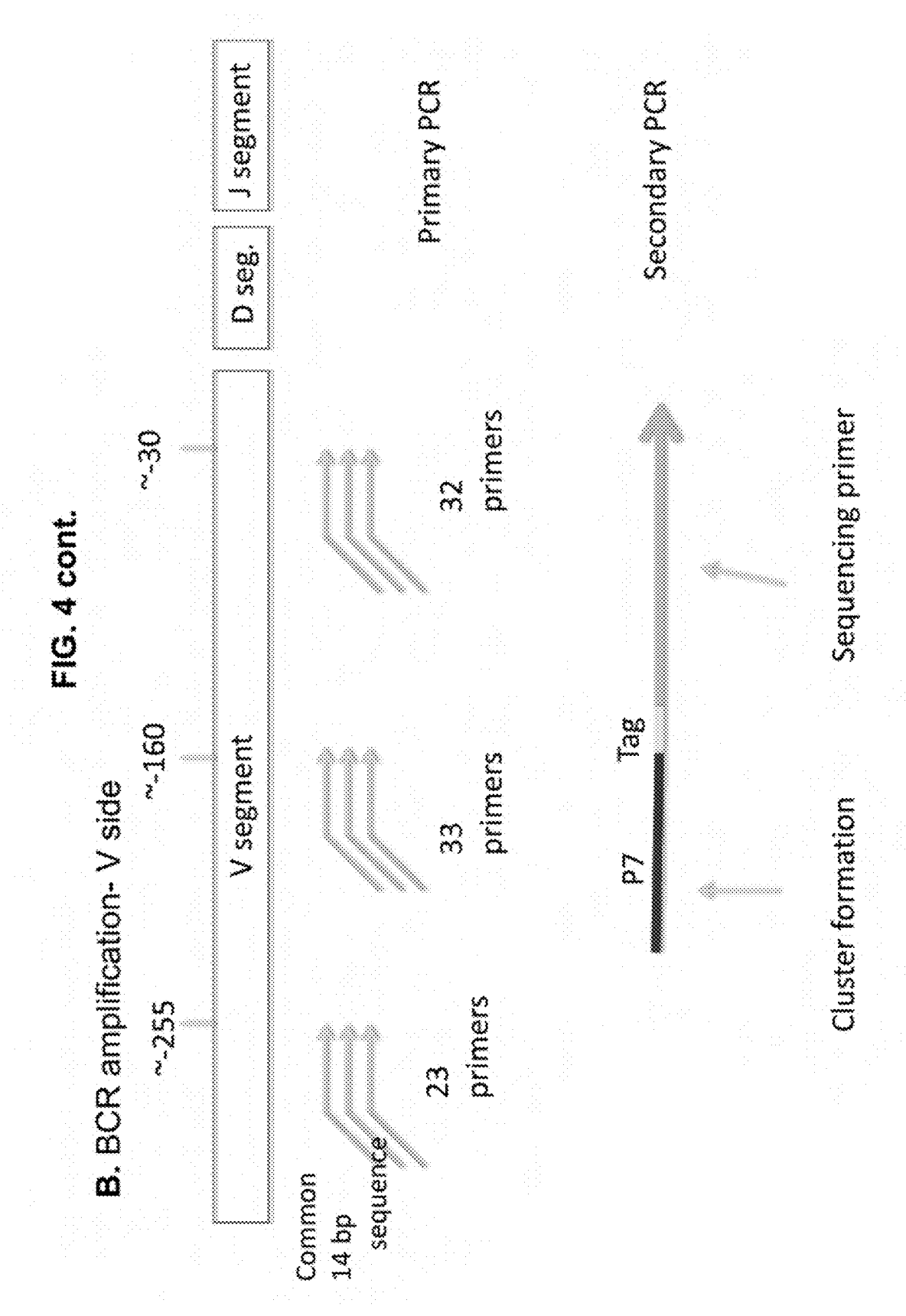

TCR$\beta$ or immunoglobulin sequences can be amplified from nucleic acid in a multiplex reaction using at least one primer that anneals to the C region and one or more primers that can anneal to one or more V segments (FIG. 2 and FIG. 4). The number of primers that anneal to V segments in a multiplex reaction can be, for example, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80. The number of primers that anneal to V segments in a multiplex reaction can be, for example, 10-60, 20-50, 30-50, 40-50, 20-40, 30-40, or 35-40. The primers can anneal to different V segments. For IgH genes, because of the possibility of somatic mutations in the V segments, multiple primers that anneal to each V segment can be used; for example, 1, 2, 3, 4, or 5 primers per V segment. The number of primers that anneal to C segments in a multiplex reaction can include, for example, at least 1, 2, 3, 4, 5, 6, 7, 8, 9, 10, 11, 12, 13, 14, or 15. The number of primers that anneal to C segments in a multiplex reaction can be 1-10, 2-9, 3-8, 4-7, 3-8, or 3-6. Amplification of TCR or immunoglobulin genes can occur as described in Example 3 and/or Example 4.

The region to be amplified can include the full clonal sequence or a subset of the clonal sequence, including the V-D junction, D-J junction of an immunoglobulin or T-cell receptor gene, the full variable region of an immunoglobulin or T-cell receptor gene, the antigen recognition region, or a CDR, e.g., complementarity determining region 3 (CDR3).

Figure 3:
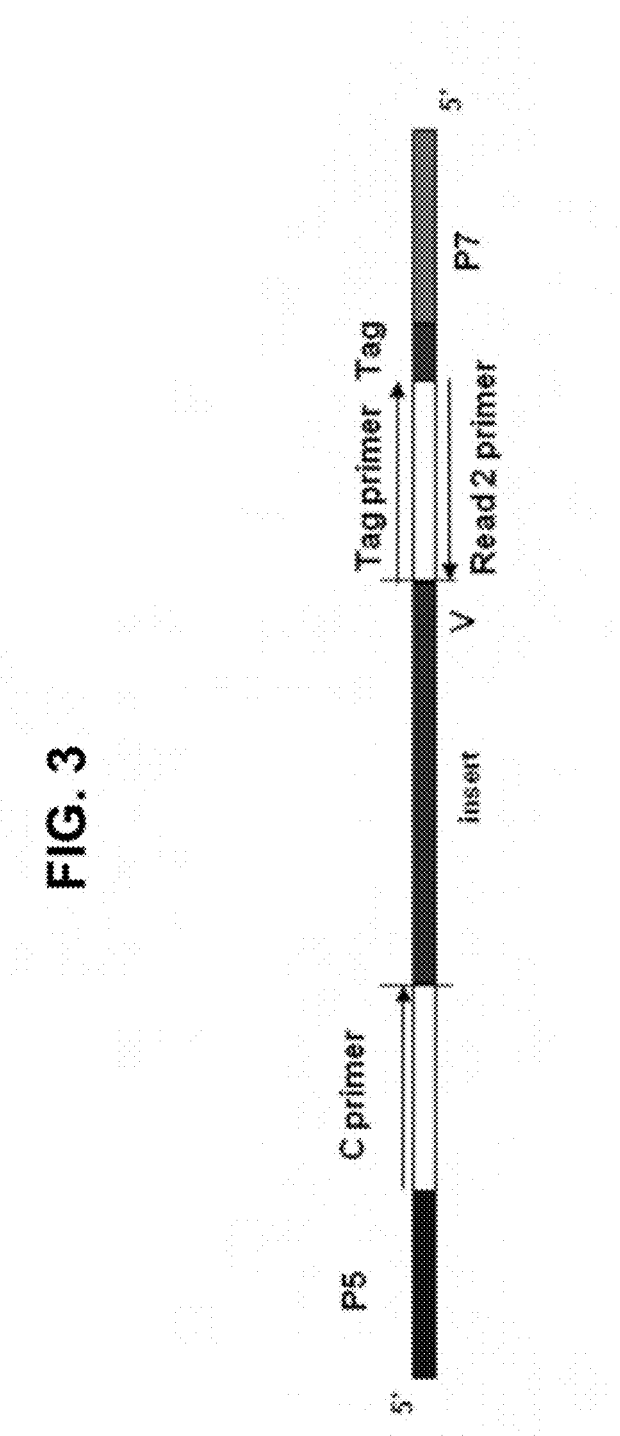
FIG. 3 illustrates a PCR product to be sequenced that was amplified using the scheme in FIG. 2.

The TCR or immunoglobulin sequence can amplified using a primary and a secondary amplification step. Each of the different amplification steps can comprise different primers. The different primers can introduce sequence not original present in the immune gene sequence. For example, the amplification procedure can add one or more tags to the 5' and/or 3' end of amplified TCR or immunoglobulin sequence (FIG. 3). The tag can be sequence that facilitates subsequent sequencing of the amplified DNA. The tag can be sequence that facilitates binding the amplified sequence to a solid support.

Other methods for amplification may not employ any primers in the V region. Instead, a specific primer can be used from the C segment and a generic primer can be put in the other side (5'). The generic primer can be appended in the cDNA synthesis through different methods including the well described methods of strand switching. Similarly, the generic primer can be appended after cDNA making through different methods including ligation.

Other means of amplifying nucleic acid that can be used in the methods of the provided invention include, for example, reverse transcription-PCR, real-time PCR, quantitative real-time PCR, digital PCR (dPCR), digital emulsion PCR (dePCR), clonal PCR, amplified fragment length polymorphism PCR (AFLP PCR), allele specific PCR, assembly PCR, asymmetric PCR (in which a great excess of primers for a chosen strand is used), colony PCR, helicase-dependent amplification (HDA), Hot Start PCR, inverse PCR (IPCR), in situ PCR, long PCR (extension of DNA greater than about 5 kilobases), multiplex PCR, nested PCR (uses more than one pair of primers), single-cell PCR, touchdown PCR, loop-mediated isothermal PCR (LAMP), and nucleic acid sequence based amplification (NASBA). Other amplification schemes include: Ligase Chain Reaction, Branch DNA Amplification, Rolling Circle Amplification, Circle to Circle Amplification, SPIA amplification, Target Amplification by Capture and Ligation (TACL) amplification, and RACE amplification.

The information in RNA in a sample can be converted to cDNA by using reverse transcription. PolyA primers, random primers, and/or gene specific primers can be used in reverse transcription reactions.

After amplification of DNA from the genome (or amplification of nucleic acid in the form of cDNA by reverse transcribing RNA), the individual nucleic acid molecules can be isolated, optionally re-amplified, and then sequenced individually.

Polymerases that can be used for amplification in the methods of the provided invention include, for example, Taq polymerase, AccuPrime polymerase, or Pfu. The choice of polymerase to use can be based on whether fidelity or efficiency is preferred.

In one embodiment, individual cells in a sample are isolated. Two or more sequences from each isolated cell can be linked together. For example, sequences from TCRα and TCRβ genes or IgH and IgK genes from an individual cell can be linked, for example by an amplification scheme (FIGS. 9-13) or a ligation scheme. The linked TCRα and TCRβ or IgH and IgK sequences for isolated cells can optionally be reamplified. The linked amplification products can be optionally repooled after amplification.

3. Means of Isolating Individual Nucleic Acids

Methods for isolation of nucleic acids from a pool include subcloning nucleic acid into DNA vectors and transforming bacteria (bacterial cloning), spatial separation of the molecules in two dimensions on a solid substrate (e.g., glass slide), spatial separation of the molecules in three dimensions in a solution within micelles (such as can be achieved using oil emulsions with or without immobilizing the molecules on a solid surface such as beads), or using microreaction chambers in, for example, microfluidic or nano-fluidic chips. Dilution can be used to ensure that on average a single molecule is present in a given volume, spatial region, bead, or reaction chamber.

Real time PCR, picogreen staining, nanofluidic electrophoresis (e.g. LabChip) or UV absorption measurements can be used in an initial step to judge the functional amount of amplifiable material.

Methods for re-amplification of nucleic acids include bacterial growth of isolated colonies transformed with nucleic acid, amplification on a slide (e.g., PCR colonies (polonies)), and amplification on a bead. The same method can be use to amplify and re-amplify the nucleic acid or a different method can be used to amplify and reamplify the nucleic acid.

In certain embodiments the subcloning steps include a step in which a common primer is attached to the DNA or RNA through an amplification or ligation step. This primer is then used to amplify the clones and as a recognition sequence for hybridization of a primer for sequencing (FIG. 2).

In other embodiments, nucleic acids are analyzed from a subset of cells. A method to separate cells, for example by using a cell surface marker, can be employed. For example, cells can be isolated by cell sorting flow-cytometry, flow-sorting, fluorescent activated cell sorting (FACS), bead based separation such as magnetic cell sorting (MACS; e.g., using antibody coated magnetic particles), size-based separation (e.g., a sieve, an array of obstacles, or a filter), sorting in a microfluidics device, antibody-based separation, sedimentation, affinity adsorption, affinity extraction, or density gradient centrifugation. Cells can be purified by laser capture microdissection. Sorting can be based on cell size, morphology, or intracellular or extracellular markers. Methods for isolating or sorting tumor cells are described, for example, in Nagrath S. et al. (2007) *Nature* 450:1235-1239; U.S. Pat. Nos. 6,008,002, 7,232,653, and 7332288; PCT Publication No. WO2008157220A1; and US Patent Application Nos. US20080138805A1 and US20090186065; and Rosenberg R. et al. (2002) *Cytometry* 49:150-158, each of which is herein incorporated by reference in their entireties.

The subset of cells can be a subset of T-cells and/or B-cells. The subset of T cells can be CD4+, CD8+, or $CD27^{high}$ cells.

Fluorescence-activated cell sorting (FACS) uses light scattering and fluorescent characteristics to sort cells. A fluorescent property can be imparted on a cell using, e.g., nucleic acid probes or antibodies conjugated to a fluorescent dye. A cell suspension can form a stream of flowing liquid. The stream of cells forms drops that contain approximately one cell per drop. Before the stream forms drops, a fluorescent characteristic of each cell is measured. A charge is placed on an electrical charging ring prior to fluorescence intensity measurement and the opposite charge is carried on the drop as it breaks from the stream. The charged drops pass through two high voltage deflection plates that divert drops into different containers based upon their charge. The charge can be directly applied to the stream and the drop breaking off retains the charge of the same sign as the stream. The stream is then returned to neutral after the drop breaks off.

Direct or indirect immunofluorescence can be used in FACS. In direct immunofluorescence, an antibody is directly conjugated to a fluorescent dye. In indirect immunofluorescence, the primary antibody is not labeled, and a secondary antibody is conjugated to a fluorescent dye.

In one embodiment, individual cells from a sample can be isolated. Sequence information from two more genes in a cell can be linked together. For example, a sample can be from a patient with an autoimmune disease, and sequence information from TCRα and TCRβ genes from spatially isolated cells from the sample can be physically linked by, for example, an amplification scheme or a ligation scheme. The linked TCRα and TCRβ sequences can optionally be amplified and/or pooled with linked sequences from other cells. The linked sequences can alternatively be for IgH and IgK or for IgH and IgL C. Sequencing Techniques Any technique for sequencing nucleic acid known to those skilled in the art can be used in the methods of the provided invention. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of the separated molecules has more recently been demonstrated by sequential or single extension reactions using polymerases or ligases as well as by single or sequential differential hybridizations with libraries of probes. These reactions have been performed on many clonal sequences in parallel including demonstrations in current commercial applications of over 100 million sequences in parallel. These sequencing approaches can thus be used to study the repertoire of T-cell receptor (TCR) and/or B-cell receptor (BCR).

The sequencing technique used in the methods of the provided invention can generate least 1000 reads per run, at least 10,000 reads per run, at least 100,000 reads per run, at least 500,000 reads per run, or at least 1,000,000 reads per run.

The sequencing technique used in the methods of the provided invention can generate about 30 bp, about 40 bp, about 50 bp, about 60 bp, about 70 bp, about 80 bp, about 90 bp, about 100 bp, about 110, about 120 bp per read, about 150 bp, about 200 bp, about 250 bp, about 300 bp, about 350 bp, about 400 bp, about 450 bp, about 500 bp, about 550 bp, or about 600 bp per read.

The sequencing technique used in the methods of the provided invention can generate at least 30, 40, 50, 60, 70, 80, 90, 100, 110, 120, 150, 200, 250, 300, 350, 400, 450, 500, 550, or 600 bp per read.

1. True Single Molecule Sequencing

A sequencing technique that can be used in the methods of the provided invention includes, for example, Helicos True Single Molecule Sequencing (tSMS) (Harris T. D. et al. (2008) *Science* 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step.

2. 454 Sequencing

Another example of a DNA sequencing technique that can be used in the methods of the provided invention is 454 sequencing (Roche) (Margulies, M et al. 2005, *Nature*, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated.

Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

3. SOLiD Sequencing

Another example of a DNA sequencing technique that can be used in the methods of the provided invention is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide.

The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

4. SOLEXA Sequencing

Another example of a sequencing technology that can be used in the methods of the provided invention is SOLEXA sequencing (Illumina). SOLEXA sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

5. SMRT Sequencing

Another example of a sequencing technology that can be used in the methods of the provided invention includes the single molecule, real-time (SMRT™) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

6. Nanopore Sequencing

Another example of a sequencing technique that can be used is the methods of the provided invention is nanopore sequencing (Soni G V and Meller A. (2007) *Clin Chem* 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

7. Chemical-Sensitive Field Effect Transistor Array Sequencing

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

8. Sequencing with an Electron Microscope

Another example of a sequencing technique that can be used in the methods of the provided invention involves using a electron microscope (Moudrianakis E. N. and Beer M. *Proc Natl Acad Sci USA*. 1965 March; 53:564-71). In one example of the technique, individual DNA molecules are labeled using metallic labels that are distinguishable using an electron microscope. These molecules are then stretched on a flat surface and imaged using an electron microscope to measure sequences.

Any one of the sequencing techniques described herein can be used in the methods of the provided invention.

D. Methods for Sequencing the TCR and BCR Repertoire

Sequences can be read that originate from a single molecule or that originate from amplifications from a single molecule. Millions of independent amplifications of single molecules can be performed in parallel either on a solid surface or in tiny compartments in water/oil emulsion. The DNA sample to be sequenced can be diluted and/or dispersed sufficiently to obtain one molecule in each compartment. This dilution can be followed by DNA amplification to generate copies of the original DNA sequences and creating "clusters" of molecules all having the same sequence. These clusters can then be sequenced. Many millions of reads can be generated in one run. Sequence can be generated starting at the 5' end of a given strand of an amplified sequence and/or sequence can be generated from starting from the 5' end of the complementary sequence. In a preferred embodiment, sequence from strands is generated, i.e. paired end reads.

The prevalence of a particular sequence in the original DNA sequence can then be measured by counting how many clusters carry that sequence. More prevalent sequences in the original sample lead to more compartments and more clusters containing the specific sequences.

Methods can be used in the amplification schemes to ensure that the frequency of the DNA sequences measured matches the frequency of the DNA sequence in the original sample. The methods can include ensuring that PCR primer concentration are high enough to drive each hybridization reaction to saturation in each cycle, adjusting individual primer concentrations to minimize the differential amplification of different sequences, etc.

Algorithms can be used to determine which sequences generated by the sequencer originate from the DNA sequence. Individually measured sequences (reads) may be offset relative to each other, contain errors introduced by amplification and/or by sequencing. An algorithm can be used to combine reads together to more accurately determine the frequency of a DNA sequence in the starting material.

A million sequencing reads or more for IgH and/or TCRβ originally amplified from a blood sample comprising DNA or RNA can be obtained. The number of reads for a specific IgH or TCRβ sequence relate to the frequency of the specific clonotype in the blood sample. Therefore, the quantity of each of the clonotypes can be determined. If the pathogenic clonotypes for a particular patient are known, their level can be determined accurately through this sequencing approach.

In certain embodiments of the provided invention, a collection of DNA molecules including a representation of the genomic DNA or reverse transcribed RNA from the TCR and BCR regions of immune cells from one or more subjects is extracted and optionally amplified in such a way that each molecule can be sequenced using one or more of the sequencing techniques described above in order to be able to detect the presence and frequency of sequences in a subject.

Different regions of immunoglobulin or T cell receptor genes can be sequenced. In some embodiments, the full sequence of the variable regions can be sequenced to identify and quantify a clonotype.

A unique subset of the full clonal sequences can be sequenced. In some embodiments, nucleotides comprising the VD and the DJ junctions are sequenced to uniquely identify and quantify a clonotype. In other embodiments, the fragment that can be sequenced is the full variable region. In yet another embodiment, the antigen recognition region or the complementarity determining region 3 (CDR3) is sequenced. A fragment containing the full CDR3 or the full variable region can be amplified to allow the sequencing of the CDR3 comprising parts of the V, D, and J segments.

One or more tags on amplified products can be used for sequencing immunoglobulin or T cell receptor genes. One or more primers that anneal to the tags can be used in the sequencing reactions. Different sections of an amplified molecule can be sequenced in separate reactions, and the sequencing results can be pieced together to generate a partial or a full sequence of the molecule.

In one embodiment, only the CDR3 is amplified and sequenced. Amplification and sequencing of the CDR3 can be accomplished by using primers specific to one or more V segment sequences (as well as one or more primer(s) on the other side of the amplicon in the C segment). Primers for each of the V segments can be utilized in one or more amplification reactions leading to the amplification of the full repertoire of sequences. This repertoire of sequences can then be mixed and subjected to separation, with or without amplification, and sequenced using any of the sequencing techniques described. When the amplification with the various V primers is done in separate tubes, the number of molecules carrying the different V segments can be "normalized" due to PCR saturation. For example, if one particular V segment had one or several clonal expansions leading to its representation more than other segments this information may be erased or decreased since the PCR reaction for each segment can be driven to saturation or close to it. Real time PCR can be used to quantify how much of each V segment is present. The full CDR3 can be sequenced, or a subset of the sequence CDR3 can be sequenced.

In one embodiment, only a subset of clonotypes is analyzed. This can be accomplished by amplifying with a primer specific to the subset of clonotypes, for example, a primer that is specific to the V segment. Unique clonotypes can be identified by sequencing with long contiguous reads that provide full connectivity. In some embodiments, when several sequences of interest are present, a short read length across only one of the junctions can generate degenerate tags that are not unique to a specific clonotype but are shared among multiple clonotypes. For example sequencing across the V/J junction can lump all the sequences with the same V/J irrespective of the D segment as one clonotype. Information on the full connectivity of all segments allows sequences to be distinguished that may share the same V and J segments but are connected to different D segments, for example.

The same analysis can be done when only the V and D are present (e.g., the light chain of an antibody or the a subunit in TCR). The full diversity of TCR and BCR incorporates both subunits. However, it is possible to do the analysis on the sequences of both subunits.

Errors generated by sequencing and/or by amplification can be taken into account when generating the clonotype profile. For example, see Example 5.

The initial amplification can be done from DNA or RNA (e.g., after conversion to cDNA).

II. Methods for Determining Correlating Clonotypes, Disease Activity Scores, and Algorithms for Determining Either or Both

A. Correlating Versus Non-Correlating Clonotypes

The vast repertoire of T and B cell receptor sequences creates a challenge in finding individual cells that are correlated with specific human health outcomes. In many cases the sequences of clonotypes that will be of interest will be unique to the individual being studied. The methods of the present invention provide means for distinguishing a) correlating clonotypes (which can be those clonotypes whose level correlate with disease) from b) non-correlating clonotypes (which can be those clonotypes whose levels do not correlate with disease). In one embodiment, a correlating clonotype can display either positive or negative correlation with disease. In another embodiment, a clonotype present at a peak state of a disease but not present at a non-peak state of a disease can be a correlating clonotype (positive correlation with disease). In another embodiment, a clonotype that is more abundant (i.e. is present at a higher level of molecules) in a peak state (or stage) of a disease than at a non-peak state of the disease can be a correlating clonotype (positive correlation with the disease). In another embodiment, a clonotype absent at a peak state of a disease but present during a non-peak state of the disease can be a correlating clonotype (negative correlation with disease). In another embodiment, a clonotype that is less abundant at a peak state of a disease than at a non-peak state of a disease can be a correlating clonotype (negative correlation with disease). In another embodiment, a correlating clonotype for an individual is determined by an algorithm.

B. Discovering Correlating and Non-Correlating Clonotypes Using a Calibration Test without a Population Study In this embodiment of the invention, correlating clonotypes are identified by looking at the clonotypes present in some sample that has relevance to a disease state (e.g., see FIG. 14). This state could be blood from a sample at a peak state of disease (e.g. a blood sample from an MS or lupus patient during an acute flare), or affected tissue that is presumed to be enriched for T and B cells involved in the disease for that individual. Examples of these tissues could be kidney biopsies of lupus patients with kidney inflammations, CSF in MS patients during a flare, synovial fluid for rheumatoid arthritis patients, or tumor samples from cancer patients. In all of these examples, it is likely that the tissues will contain relevant T and B cells that are related to the disease (though not necessarily the causative agents). It is notable that if this method is used to identify the clonotypes that are relevant to disease, they will only be relevant to the individual in whose sample they were detected. As a result, a specific calibration test will be needed in order to use this method to identify correlating clonotypes in any given individual with a disease.

In one embodiment, a method for determining one or more correlating clonotypes in a subject is provided. The method can include steps for a) generating one or more clonotype profiles by nucleic acid sequencing individual, spatially isolated molecules from at least one sample from the subject, wherein the at least one sample is related to a first state of the disease, and b) determining one or more correlating clonotypes in the subject based on the one or more clonotype profiles.

In one embodiment, at least one sample is from a tissue affected by the disease. In another embodiment, said determination of one or more correlating clonotypes comprises comparing clonotype profiles from at least two samples. In another embodiment, the first state of the disease is a peak state of the disease. In another embodiment, one or more correlating clonotypes are present in the peak state of the disease. In another embodiment, the one or more correlating clonotypes are absent in the peak state of the disease. In another embodiment, one or more correlating clonotypes are high in the peak state of the disease. In another embodiment, one or more correlating clonotypes are low in the peak state of the disease. In another embodiment, the sample comprises T-cells and/or B-cells. In another embodiment, the T-cells and/or B-cells comprise a subset of T-cells and/or B-cells. In another embodiment, the subset of T-cells and/or B-cells are enriched by interaction with a marker. In another embodiment, the marker is a cell surface marker on the subset of T-cells and/or B-cells. In another embodiment, the subset of T-cells and/or B-cells interacts with an antigen specifically present in the disease.

In one embodiment, the disease is an autoimmune disease. In another embodiment, the autoimmune disease is systemic lupus erythematosus, multiple sclerosis, rheumatoid arthritis, or Ankylosing Spondylitis.

C. Discovering Correlating and Non-Correlating Clonotypes Using a Population Study In one embodiment, a method is provided for identifying correlating clonotypes using a population study (e.g., see FIG. 15). The utility of the population study is that it allows the specific information about correlating clonotypes that have been ascertained in individuals with known disease state outcomes to be generalized to allow such correlating clonotypes to be identified in all future subjects without the need for a calibration test. Knowledge of a specific set of correlating clonotypes can be used to extract rules about the likely attributes (parameters) of clonotypes that will correlate in future subjects.

In one embodiment, the provided invention encompasses methods that include identifying correlating and non correlating clonotypes by sequencing the immune cell repertoire in a study of samples from patients with disease(s) and optionally healthy controls at different times and, in the case of the patients with a disease, at different (and known) states of the disease course characterized by clinical data. The disease can be, for example, an autoimmune disease. The clonotypes whose level is correlated with measures of disease in these different states can be used to develop an algorithm that predicts the identity of a larger set of sequences that will correlate with disease as distinct from those that will not correlate with disease in all individuals. Unlike the case of the calibration test, correlating sequences need not have been present in the discovery study but can be predicted based on these sequences. For example, a correlating sequence can be TCR gene DNA sequence that encodes the same amino acid sequence as the DNA sequence of a clonotype identified in the discovery study. Furthermore, the algorithm that can predict one or more correlating clonotypes can be used to identify clonotypes in a sample from any individual and is in no way unique to a given individual, thus allowing the correlating clonotypes to be predicted in a novel sample without prior knowledge of the clonotypes present in that individual.

In one aspect, a method for developing an algorithm that predicts one or more correlating clonotypes in any sample from a subject with a disease is provided comprising: a) generating a plurality of clonotype profiles from a set of samples, wherein the samples are relevant to the disease, b) identifying one or more correlating clonotypes from the set of samples, c) using sequence parameters and/or functional data from one or more correlating clonotypes identified in b) to develop an algorithm that can predict correlating clonotypes in any sample from a subject with the disease.

In one embodiment, the set of samples are taken from one or more tissues affected by the disease.

In another embodiment, the identifying one or more correlating clonotypes comprises comparing clonotype profiles from at least two samples. In another embodiment, the functional data include binding ability of markers in T-cell and/or B-cells or interaction with antigen by a T-cell or B cell. In another embodiment, said sequence parameters comprise nucleic acid sequence and predicted amino acid sequence. In another embodiment, the samples are from one or more individuals at a peak stage of the disease. In another embodiment, said one or more correlating clonotypes are present in the peak state of the disease. In another embodiment, said one or more correlating clonotypes are at a high level in the peak state of the disease. In another embodiment, one or more correlating clonotypes are at a low level in the peak state of the disease. In another embodiment, one or more correlating clonotypes are absent at the peak state of the disease.

In one embodiment, the disease is an autoimmune disease. In another embodiment, the autoimmune disease is systemic lupus erythematosus, multiple sclerosis, rheumatoid arthritis, or Ankylosing Spondylitis.

In another aspect, a method for discovering one or more correlating clonotypes for an individual is provided, comprising a) inputting a clonotype profile from a sample from the individual into an algorithm, and b) using the algorithm to determine one or more correlating clonotypes for the individual. The algorithm can be an algorithm developed by: a) generating a plurality of clonotype profiles from a set of samples, wherein the samples are relevant to the disease, b) identifying one or more correlating clonotypes from the set of samples, and c) using sequence parameters and/or functional data from one or more correlating clonotypes identified in b) to develop the algorithm that can predict correlating clonotypes in any sample from a subject with the disease.

D. Discovering Correlating and Non Correlating Clonotypes Using a Calibration Test Combined with a Population Study In one embodiment of the invention the correlating clonotypes are identified by using a calibration test combined with a population study (e.g., see FIG. 17). In this embodiment the population study does not result in an algorithm that allows clonotypes to be predicted in any sample but rather it allows an algorithm to be developed to predict correlating clonotypes in any sample from a subject for whom a particular calibration clonotype profile has been generated (e.g., see FIG. 16). An example of this could be the development of an algorithm that would predict the correlating clonotypes in a lupus patient based on the clonotype profile measured from a blood sample at any stage of disease after having first having had a blood test taken during a clinical flare state that was used to calibrate the algorithm.

In this embodiment the provided invention encompasses methods for identifying correlating and non-correlating clonotypes by sequencing the immune cell repertoire in a study of samples from patients of disease(s) and optionally healthy controls at different times and, in the case of the patients with a disease, at different (and known) states of the disease course characterized by clinical data. The clonotypes that are found at different frequency (or level) in the first state than in the second state are then used to develop an algorithm that predicts which of the sequences found in the repertoires of each individual at the first disease state will correlate with disease at the later state in each individual as distinct from those that will not correlate with disease in that individual. Unlike the case of the calibration test alone, correlating sequences may be a subset of all the sequences found to be different between disease states. It is also possible that correlating clonotypes are not found in the calibration sample but are predicted based on the algorithm to be correlating if they appear in a future sample. As an example, a clonotype that codes for the same amino acid sequence as a clonotype found in a calibration sample may be predicted to be a correlating clonotype based on the algorithm that results from the population study. Unlike the previous embodiments, the algorithm is developed to predict the correlating clonotypes based on a calibration clonotype profile which is a clonotype profile generated in the individual for whom the correlating clonotypes are to be predicted which at a specific state of disease. In this embodiment the algorithm cannot be used to generate correlating clonotypes in a particular individual until a specific calibration clonotype profile has been measured. After this calibration profile has been measured in a particular subject, all subsequent correlating clonotypes can be predicted based on the measurement of the clonotype profiles in that individual.

In another aspect, a method for discovering one or more correlating clonotypes for an individual is provided, comprising a) inputting a clonotype profile from a sample from the individual into an algorithm, and b) using the algorithm to determine one or more correlating clonotypes for the individual. The algorithm can be an algorithm developed by: a) generating a plurality of clonotype profiles from a set of samples, wherein the samples are relevant to the disease, b) identifying one or more correlating clonotypes from the set of samples, and c) using sequence parameters and/or functional data from one or more correlating clonotypes identified in b)

to develop an algorithm that can predict correlating clonotypes in any sample from a subject with the disease. In one embodiment, the sample is at taken at a peak state of disease. In another embodiment, the sample is taken from disease affected tissue.

E. Sequence Related Parameters that can be Used to Predict Correlating Clonotypes In order to conduct a population study a training set can be used to understand the characteristics of correlating clonotypes by testing various parameters that can distinguish those correlating clonotypes from those that do not. These parameters include the sequence or the specific V, D, and J segments used. In one embodiment it is shown that specific V segments are more likely to correlate with some diseases as is the case if the clonotypes for a specific disease are likely to recognize related epitopes and hence may have sequence similarity. Other parameters included in further embodiments include the extent of hypersomatic mutation identified and the level of a clonotype at the peak of an episode and its level when the disease is relatively inactive. Other parameters that may predict correlating clonotypes include without limitation: 1) sequence motifs including V or J region, a combination VJ, short sequences in DJ region; 2) Sequence length of the clonotype; 3) Level of the clonotype including absolute level (number of clones per million molecules) or rank level; 4) Amino acid and nucleic acid sequence similarity to other clonotypes: the frequency of other highly related clonotypes, including those with silent changes (nucleotide differences that code for same amino acids) or those with conservative amino acid changes; 5) For the BCRs the level of somatic mutations in the clonotype and/or the number of distinct clonotypes that differ by somatic mutations from some germline clonotypes; 6) clonotypes whose associated proteins have similar 3 dimensional structures.

F. Functional Data to Refine the Determination of Correlating Clonotypes

Further embodiments will make use of functional data to aid in identifying correlating clonotypes. For example, T-cells and/or B-cells containing certain markers that are enriched in cells containing correlating clonotypes can be captured through standard methods like FACS or MACS. In another embodiment the marker is a cell-surface marker. In another embodiment T-cells and/or B-cells reactivity to an antigen relevant to the pathology or to affected tissue would be good evidence of the pathological relevance of a clonotype.

In another embodiment the sequence of the candidate clonotypes can be synthesized and put in the context of the full TCR or BCR and assessed for the relevant reactivity. Alternatively, the amplified fragments of the different sequences can be used as an input to phage, ribosome, or RNA display techniques. These techniques can select for the sequences with the relevant reactivity. The comparison of the sequencing results for those before and after the selection can identify those clones that have the reactivity and hence are likely to be pathological. In another embodiment, the specific display techniques (for example phage, ribosome, or RNA display) can be used in an array format. The individual molecules (or amplifications of these individual molecules) carrying individual sequences from the TCR or BCR (for example CDR3 sequences) can be arrayed either as phages, ribosomes, or RNA. Specific antigens can then be studied to identify the sequence(s) that code for peptides that bind them. Peptides binding antigens relevant to the disease are likely to be pathological.

G. Generating an Immune Load Algorithm

An algorithm can be used to compute an Immune Load (e.g., see FIG. 18). The Immune Load can be used to make a clinical decision. Using data from an experiment, (e.g., an experiment comprising samples from subjects in a first state of a disease and samples from subjects in a second state of the disease), an algorithm can be developed that combines the information about the levels of the correlating and non-correlating clonotypes into a single score (Immune Load). The parameters of this algorithm can then be adjusted to maximize the correlation between Immune Load and the clinical data. For example, the clinical data can be a clinical measure of disease severity (e.g., the extent of lesions on an MRI for a multiple sclerosis patient).

The correlating clonotypes used in generating a Immune Load algorithm can be generated using a calibration test, a population study, or a calibration test and a population study as described above.

Some of the factors that can be considered in combining the correlating clonotypes are the number of correlating clonotypes, their level, their rate of change (velocity), and the rate of change in the velocity (acceleration). Other factors to be assessed include the level of the clonotypes at the episode peak and at the inactive disease state In one embodiment, the Immune Load generated relates to an autoimmune disease. Such a Load can be referred to as an AutoImm Load.

In one aspect, a method for generating an algorithm that calculates a disease activity score is provided, comprising: a) developing an algorithm that uses a set of factors to combine levels of correlating clonotypes into a disease activity score, b) comparing the disease activity score to clinical data regarding the disease state, and c) optimizing the factors in order to maximize the correlation between clinical data and the disease activity score.

H. Monitoring Disease Using the Load Algorithm

1. Monitoring Disease without a Calibration Test

In one embodiment of the invention the clonotypes and the Immune Load algorithm are determined using a population study (e.g., see FIG. 19) Immune Load can be used directly without having to first calibrate the individual patient. This test can be done when the patient is in any disease state. This test can be used to generate specific correlating and non-correlating clonotypes based on the algorithm developed above. Immune Load can then be calculated using the second algorithm generated in a population study. This score can then be used clinically.

In another aspect, a method for monitoring the disease state of a individual is provided comprising: a) determining a clonotype profile from a sample from a subject, b) inputting the clonotype profile information from a) into an algorithm, and c) using the algorithm to generate a score predictive of the disease state of the individual. The algorithm can be an algorithm generated by a) developing an algorithm that uses a set of factors to combine levels of correlating clonotypes into a disease activity score, b) comparing the disease activity score to clinical data regarding the disease state, and c) optimizing the factors in order to maximize the correlation between clinical data and the disease activity score.

2. Monitoring Disease Using a Calibration Test

In one embodiment of the provided invention the correlating clonotypes and the Immune Load algorithm are determined using a calibration test or calibration test and a population study (e.g., see FIG. 20). Immune Load can be used in the clinic by first conducting a calibration test. This test can be done when the patient is in a state which is similar to the first state used in the study that generated the correlating and non-correlating clonotypes that are used in the Immune Load algorithm. For example, this state can be a flare state of an autoimmune disease if this is how the Immune Load algorithm was derived. This calibration test can then be used to generate the specific correlating and non-correlating clonotypes to be used in the subsequent disease monitoring tests. At a later point in the treatment of this patient, another test is done on the patient and Immune Load can be calculated using the algorithm generated in the discovery study, and the list of clonotype levels generated in this patient's specific calibration test. This Immune Load score can then be used clinically.

In another aspect, a method for monitoring the disease state of a individual is provided comprising: a) determining a clonotype profile from a sample from a subject, b) inputting the clonotype profile information from a) into an algorithm, and c) using the algorithm to generate a score predictive of the disease state of the individual. The algorithm can be an algorithm generated a) developing an algorithm that uses a set of factors to combine levels of correlating clonotypes into a disease activity score, b) comparing the disease activity score to clinical data regarding the disease state, and c) optimizing the factors in order to maximize the correlation between clinical data and the disease activity score. In another embodiment, the method can further comprise determining one or more correlating clonotypes in the individual by any of the methods of the provided invention, and inputting information the one or more correlating clonotypes into the algorithm.

In one embodiment, the disease is an autoimmune disease. In another embodiment, the autoimmune disease is systemic lupus erythematosus, multiple sclerosis, rheumatoid arthritis, or Ankylosing Spondylitis.

3. Other Factors Related to the Use of Immune Load

The same Immune Load may mean different things for different patients. For one, the full clinical picture of a patient needs to be considered. From a testing perspective, one may consider the velocity (rate of change of Immune Load over time) and acceleration (rate of change of velocity over time) in addition to the level of Immune Load in making clinical decisions. For example if the AutoImm Load score is increasing (high velocity) it may be predictive of an incipient flare in an autoimmune disease.

Additional tests that can be integrated in the Load score, for example, an AutoImm Load score, include, for example, erythrocyte sedimentation rate (ESR), C-reactive protein (CRP) levels, Anti-ds DNA, other autoantibody titers, complement levels, urine protein levels, Urine protein/creatinine ratio, creatinine levels, blood urea nitrogen (BUN) levels, platelet levels, WBC counts, hematorcrit (Hct), Hb, urinalysis results. Other tests that are related to SLE that can be integrated include, for example, CD27 level, CD27++ cell level, INF-responsive genes (Baechler, E C et al. (2003) *Proc. Natl. Acad. Sci.* 100: 2610-2615), and chemokine score (Bauer J W et al. (2009) *Arthritis Rheum.* 60:3098-3107). Other tests not related to lupus include, for example, thyroid-stimulating hormone (TSH) test, triiodothyronine (T3) test, thyroxine (T4) test, liver function tests (LFTs), other autoantibodies, calprotectin test, lactoferrin test, and synovial fluid analysis. The additional tests can include imaging test, including, for example, MRI, CT-scan, X-ray, and ultrasound.

III. Determining Disease States

Because the immune system is so central to human health, the ability to measure immune responses has wide applications in medicine. This invention teaches the ability to use the immune system to understand underlying disease state when it is mediated by the immune system. This allows a very powerful set of diagnostic and prognostic applications that use the immune profiles to inform the risks of wide variety of clinical outcomes and allow physicians to intervene more effectively.

A. Utility of Immune Profiling in Autoimmune Disease Treatment

The methods of the provided invention can be used to diagnose and treat autoimmune disease in a subject. Autoimmune disease involves adaptive immune cells escaping the usual process conferring autoimmunity and attacking some target(s) on bodily tissue. Autoimmune diseases include, for example, acute disseminated encephalomyelitis, Addison's disease, ankylosing spondylitis, antiphospholipid antibody syndrome, autoimmune hemolytic anemia, autoimmune hepatitis, autoimmune inner ear disease, Behçet's disease, bullous pemphigoid, Celiac disease, Chagas disease, Chronic obstructive pulmonary disease, dermatomyositis, diabetes mellitus type 1, Goodpasture's syndrome, Graves' disease, Guillain-Barré syndrome, Hashimoto's thyroditis, Hidradenitis suppurativa, Idiopathic thrombocytopenic purpura, Interstitial cystitis, multiple sclerosis, myasthenia gravis, neuromyotonia, pemphigus vulgaris, pernicious anemia, polymyositis, primary biliary cirrhosis, rheumatoid arthritis, scleroderma, systemic lupus erythematosus, Sjögren's syndrome, and vasculitis syndromes. The stages of these autoimmune diseases can be diagnosed using the methods of the provided invention. Treatments can be suggested to a subject based on the stage of the autoimmune disease.

Clinical information regarding a subject with an autoimmune disease, or suspected of having an autoimmune disease, can be used to determine the disease state (or AutoImm load). Clinical information can be used to identify patterns of a clonotype profile that correlate with a disease state. Clinical information can include, for example, height, weight, eye color, age, gender, ethnic group, blood pressure, LDL cholesterol levels, HDL cholesterol levels, family medical history, and molecular marker information.

Clinical information can include symptoms of one or more autoimmune diseases. For autoimmune hepatitis symptoms can include fatigue, hepatomegaly, jaundice, pruritus, skin rash, arthralgia, abdominal discomfort, spider angiomas, nausea, vomiting, anorexia, dark urine, pale or gray stools. For dermatoymyositis (DM), symptoms can include rash (patchy, bluish-purple discolorations on the face, neck, shoulders, upper chest, elbows, knees, knuckles and back) accompanying or preceding muscle weakness, dysphagia, myalgia, fatigue, weight loss and low-grade fever. For Graves' disease, symptoms can include weight loss due to increased energy expenditure, increased appetite, heart rate and blood pressure, and tremors, nervousness and sweating. For Hashimoto's thyroiditis, symptoms can include mental and physical slowing, greater sensitivity to cold, weight gain, coarsening of the skin, goiter. For mixed connective tissue disease (MCTD)), symptoms can include features of systemic lupus erythematosus (SLE), scleroderma and polymyositis. For Pemphigoid, bullous (BP) symptoms can include mildly pruritic welts to severe blisters and infection, oral or esophageal bullae. For pemphigus, symptoms can include blistering of skin and mucous membranes. For pernicious anemia, symptoms can include shortness of breath, fatigue, pallor, tachycardia, inappetence, diarrhea, tingling and numbness of hands and feet, sore mouth and unsteady gait. For polymyositis (PM), symptoms can include muscle weakness, dysphagia and myalgia. For primary biliary cirrhosis (PBC), symptoms can include fatigue and pruritus. For scleroderma (systemic sclerosis), symptoms can include swelling and puffiness of the fingers or hands, skin thickening, skin ulcers on the fingers, joint stiffness in the hands, pain, sore throat and diarrhea. For Sjögren's syndrome, symptoms can include dryness of the eyes and mouth, swollen neck glands, difficulty swallowing or talking, unusual tastes or smells, thirst and tongue ulcers. For systemic lupus erythematosus (SLE)), symptoms can include fever, weight loss, hair loss, mouth and nose sores, malaise, fatigue, seizures and symptoms of mental illness, joint inflammation similar to RA, butterfly rash on nose and cheeks, extreme sensitivity to cold in the hands and feet. For vasculitis syndromes, e.g., Wegener's granulomatosis, idiopathic crescentic glomerulonephritis (ICGN), microscopic polyarteritis (MPA), pulmonary renal syndrome (PRS), symptoms can include fatigue, weakness, fever, arthralgia, abdominal pain, renal problems and neurological problems. The clinical information can be from one or more subjects at one or more points of time.

The clinical information can include information regarding responses of a subject with an autoimmune disease to one or more treatments the subject has received.

The clinical utility of AutoImm Load is discussed for specific autoimmune diseases below. Another embodiment of this invention contemplates the combination of the immune profiling tests with other markers that are already in use for the detection of disease activity in these diseases to allow tests with greater sensitivity and specificity. Other molecular identifiers or markers can be used in computing the AutoImm Load or for determining the disease state. Molecular identifiers can include nucleic acids, proteins, carbohydrates, and lipids, and expression profiles of nucleic acids or proteins. The molecular identifiers can be of human or non-human origin (e.g., bacterial). The identifiers or markers can be determined by techniques that include, for example, comparative genomic hybridization (CGH), chromosomal microarray analysis (CMA), expression profiling, DNA microarray, high-density oligonucleotide microarray, whole-genome RNA expression array, peptide microarray, enzyme-linked immunosorbent assay (ELISA), genome sequencing, copy number (CNV) analysis, small nucleotide polymorphism (SNP) analysis, immunohistochemistry, in-situ hybridization, fluorescent in-situ hybridization (FISH), PCR, Western blotting, Southern blotting, SDS-PAGE, gel electrophoresis, and Northern blotting.

For systemic lupus erythematosus, markers can include levels of erythrocyte sedimentation rate (ESR), C-reactive protein (CRP) levels, Anti-ds DNA, other autoantibody titers, complement levels, urine protein levels, Urine protein/creatinine ratio, creatinine levels, blood urea nitrogen (BUN) levels, platelet levels, WBC counts, hematocrit (Hct), Hb, and urinalysis results. Other tests that are related for instance to SLE that can be integrated include, for example, CD27 level, CD27++ cell level, INF-responsive genes, and chemokine score.

1. Systemic Lupus Erythematosus (SLE)

The methods of the provided invention can be used to determine states or stages of systemic lupus erythematosus (SLE or lupus). SLE is a serious autoimmune condition that often afflicts young adults (mostly females). It is characterized by inflammatory processes that can affect many organs including the skin, joints, kidneys, lungs, heart, and central nervous system leading to frequent disabilities and sometimes death. The disease follows a very unpredictable course marked by flare periods followed by quiescent periods of remission. Nevertheless, patients diagnosed with SLE are seen regularly by a rheumatologist and treated with a variety of serious medications. These medications include steroids such as Prednisone and other immunosuppressants such as Cellcept (mycophenolate mofetil). While these drugs can reduce organ damage they contain significant side effects including risk of infection and infertility. The unreliability for some of the symptoms (e.g., pain and fatigue) and the unpredictable disease course makes tailoring medication doses difficult, resulting in an overtreatment of some patients and under-treatment of others. As a result, the treatment of SLE poses significant therapeutic challenges to the clinician.

There are a number of standard methods a clinician can use to assess the activity of SLE. The status of the disease can be measured by observing the clinical symptoms of the disease. These methods include assessment of signs (e.g., skin rash) and symptoms (e.g., joint pain and fatigue) as well as lab results (e.g., urine protein/creatinine ratio, anti-ds DNA antibody, and blood counts). These clinical markers, however, can be lagging indicators of disease status and as such patients may respond only after weeks or months of therapy. Furthermore, in some cases symptoms can be difficult to assess with precision (e.g., pain and fatigue). Other markers of inflammation, for example anti-ds DNA antibody, complement level (e.g., C3), C reactive protein (CRP), and erythrocyte sedimentation rate (ESR) usually lack specificity and/or sensitivity. Invasive methods such as kidney biopsy are impractical for routine use. As a result clinicians perform quite a frequent testing of their patients without a perfect measure of the disease status. The clinical symptoms and laboratory assessment are integrated in measures such as Systemic Lupus Erythematosus Disease Activity Index (SLEDAI) and Physician Global Assessment (PGA). These measures are not done routinely in clinical practice and often fall short in several clinical situations.

Specific examples of the utility of AutoImm Load in making therapeutic interventions in SLE are discussed in greater detail in the examples section along with specific enabling studies that determine AutoImm Load.

2. Multiple Sclerosis (MS)

The methods of the provided invention can also be used to determine states or stages of Multiple Sclerosis (MS). MS is an autoimmune disease that affects the brain and spinal cord (central nervous system). Symptoms vary, because the location and severity of each attack can be different. Episodes can last for days, weeks, or months. These episodes alternate with periods of reduced or no symptoms (remissions). It is common for the disease to return (relapse). However, the disease may continue to get worse without periods of remission.

Because nerves in any part of the brain or spinal cord may be damaged, patients with multiple sclerosis can have symptoms in many parts of the body. Muscle symptoms include, for example, loss of balance, numbness or abnormal sensation in any area, pain because of muscle spasms, pain in the arms or legs, problems moving arms or legs, problems walking, problems with coordination and making small movements, slurred or difficult-to-understand speech, tremor in one or more arms or legs, uncontrollable spasm of muscle groups (muscle spasticity), and weakness in one or more arms or legs.

Eye symptoms include, for example, double vision, eye discomfort, uncontrollable rapid eye movements, and vision loss (usually affects one eye at a time).

Other brain and nerve symptoms include, for example, decreased attention span, decreased judgment, decreased memory, depression or feelings of sadness, dizziness and balance problems, facial pain, hearing loss, and fatigue.

Bowel and bladder symptoms include, for example, constipation, difficulty beginning urinating, frequent need to urinate, stool leakage, strong urge to urinate, and urine leakage (incontinence).

There is no known cure for multiple sclerosis at this time. However, there are therapies that may slow the disease. The goal of treatment is to control symptoms and help the patient maintain a normal quality of life.

Medications used to slow the progression of multiple sclerosis can include, for example, immune modulators to help control the immune system, including interferons (Avonex, Betaseron, or Rebif), monoclonal antibodies (Tysabri), glatiramer acetate (Copaxone), mitoxantrone (Novantrone), methotrexate, azathioprine (Imuran), cyclophosphamide (Cytoxan), and natalizumab (Tysabri). Steroids can be used to decrease the severity of attacks.

Medications to control symptoms can include, for example, medicines to reduce muscle spasms such as Lioresal (Baclofen), tizanidine (Zanaflex), or a benzodiazepine, cholinergic medications to reduce urinary problems, antidepressants for mood or behavior symptoms, and amantadine for fatigue.

MS affects women more than men. The disorder most commonly begins between ages 20 and 40, but can be seen at any age. MS is caused by damage to the myelin sheath, the protective covering that surrounds nerve cells. When this nerve covering is damaged, nerve impulses are slowed down or stopped. MS is a progressive disease, meaning the nerve damage (neurodegeneration) gets worse over time. How quickly MS gets worse varies from person to person. The nerve damage is caused by inflammation. Inflammation occurs when the body's own immune cells attack the nervous system. Repeated episodes of inflammation can occur along any area of the brain and spinal cord. Researchers are not sure what triggers the inflammation. The most common theories point to a virus or genetic defect, or a combination of both. MS is more likely to occur in northern Europe, the northern United States, southern Australia, and New Zealand than in other areas. Geographic studies indicate there may be an environmental factor involved. People with a family history of MS and those who live in a geographical area with a higher incidence rate for MS have a higher risk of the disease.

Symptoms of MS may mimic those of many other nervous system disorders. The disease is diagnosed by ruling out other conditions. People who have a form of MS called relapsing-remitting may have a history of at least two attacks, separated by a period of reduced or no symptoms. The health care provider may suspect MS if there are decreases in the function of two different parts of the central nervous system (such as abnormal reflexes) at two different times. A neurological exam may show reduced nerve function in one area of the body, or spread over many parts of the body.

Tests to diagnose multiple sclerosis include, for example, cerebrospinal fluid tests, including CSF oligoclonal banding, head MRI scan, lumbar puncture (spinal tap), nerve function study (evoked potential test), and spine MRI.

Like other autoimmune diseases, MS follows an unpredictable course with acute flares and periods of remission. There are increasing numbers of therapies, each with side effects that range from serious (weight gain and depression) to life threatening (pancytopenia and PML infections), variable effectiveness in different patients, and high costs. At the same time, the lack of highly accurate and specific routine tests of MS disease activity make the challenge of effectively administering therapy complicated. Clinical episodes can be separated by long time periods (up to years in early stage disease) even without treatment. In addition, available medications reduce the likelihood of relapse but do not completely prevent them. Therefore disease activity is difficult to assess and thus, there is an inadequate short term measure of disease activity that could be used to measure whether a specific therapy is showing efficacy in a given patient by measuring the reduction in number or severity of relapses. The only other test available for monitoring disease activity is brain MRI to track the state of lesions as revealed with the aid of contrast enhancing agents such as gadolinium. However, such imaging offers only an integrated view of brain damage and lacks specificity and time resolution. Attempting to use MRI imaging to follow disease course on time scales shorter than a year is impractical given the costs, the lack of specificity and the dangers of excessive contrast exposure. As a result, patients are often treated at great expense for prolonged periods of time without any effective feedback that would allow the physician to modify dosing and/or switch of add therapies.

3. Rheumatoid Arthritis (RA)

The methods can be used to measure disease status for Rheumatoid arthritis patients. Rheumatoid arthritis (RA) is a chronic, systemic inflammatory disorder that can affect many tissues and organs but principally attacks the joints, producing an inflammatory synovitis that often progresses to destruction of the articular cartilage and ankylosis of the joints. Rheumatoid arthritis can also produce diffuse inflammation in the lungs, pericardium, pleura, and sclera, and also nodular lesions, most common in subcutaneous tissue under the skin. Although the cause of rheumatoid arthritis is unknown, autoimmunity plays a pivotal role in its chronicity and progression.

About 1% of the world's population is afflicted by rheumatoid arthritis, women three times more often than men. Onset is most frequent between the ages of 40 and 50, but people of any age can be affected. It can be a disabling and painful condition, which can lead to substantial loss of functioning and mobility. RA is diagnosed chiefly on symptoms and signs, but can also be diagnosed with blood tests (especially a test called rheumatoid factor) and X-rays. Diagnosis and long-term management are typically performed by a rheumatologist, an expert in the diseases of joints and connective tissues.

Various treatments are available. Non-pharmacological treatment includes physical therapy, orthoses, and occupational therapy. Analgesia (painkillers) and anti-inflammatory drugs, including steroids, can be used to suppress the symptoms, while disease-modifying antirheumatic drugs (DMARDs) can be used to inhibit or halt the underlying immune process and prevent long-term damage. In recent times, the newer group of biologics has increased treatment options When RA is clinically suspected, immunological studies can be performed, such as testing for the presence of rheumatoid factor (RF, a specific antibody). A negative RF does not rule out RA; rather, the arthritis is called seronegative. This is the case in about 15% of patients. During the first year of illness, rheumatoid factor is more likely to be negative with some individuals converting to seropositive status over time. RF is also seen in other illnesses, for example Sjögren's syndrome, and in approximately 10% of the healthy population, therefore the test is not very specific.

Because of this low specificity, new serological tests have been developed, which test for the presence of so called anti-citrullinated protein antibodies (ACPAs). Like RF, these tests are positive in only a proportion (67%) of all RA cases, but are rarely positive if RA is not present, giving it a specificity of around 95%. As with RF, there is evidence for ACPAs being present in many cases even before onset of clinical disease.

The most common tests for ACPAs are the anti-CCP (cyclic citrullinated peptide) test and the Anti-MCV assay (antibodies against mutated citrullinated Vimentin). Recently, a serological point-of-care test (POCT) for the early detection of RA has been developed. This assay combines the detection of rheumatoid factor and anti-MCV for diagnosis of rheumatoid arthritis and shows a sensitivity of 72% and specificity of 99.7%.

Also, several other blood tests can be done to allow for other causes of arthritis, such as lupus erythematosus. The erythrocyte sedimentation rate (ESR), C-reactive protein, full blood count, renal function, liver enzymes and other immunological tests (e.g., antinuclear antibody/ANA) are all performed at this stage. Elevated ferritin levels can reveal hemochromatosis, a mimic RA, or be a sign of Still's disease, a seronegative, usually juvenile, variant of rheumatoid.

The term Disease modifying anti-rheumatic drug (DMARD) originally meant a drug that affects biological measures such as ESR and hemoglobin and autoantibody levels, but is now usually used to mean a drug that reduces the rate of damage to bone and cartilage. DMARDs have been found both to produce durable symptomatic remissions and to delay or halt progression. This is significant, as such damage is usually irreversible. Anti-inflammatories and analgesics improve pain and stiffness but do not prevent joint damage or slow the disease progression.

There is an increasing recognition among rheumatologists that permanent damage to the joints occurs at a very early stage in the disease. In the past it was common to start therapy with just an anti-inflammatory drug, and assess progression clinically and using X-rays. If there was evidence that joint damage was starting to occur, then a more potent DMARD would be prescribed. Ultrasound and MRI are more sensitive methods of imaging the joints and have demonstrated that joint damage occurs much earlier and in more sufferers than was previously thought. People with normal X-rays will often have erosions detectable by ultrasound that X-ray could not demonstrate. The aim now is to treat before damage occurs.

There may be other reasons why starting DMARDs early is beneficial to preventing structural joint damage. From the earliest stages of the disease, the joints are infiltrated by cells of the immune system that signal to one another in ways that may involve a variety of positive feedback loops (it has long been observed that a single corticosteroid injection may abort synovitis in a particular joint for long periods). Interrupting this process as early as possible with an effective DMARD (such as methotrexate) appears to improve the outcome from the RA for years afterwards. Delaying therapy for as little as a few months after the onset of symptoms can result in worse outcomes in the long term. There is therefore considerable interest in establishing the most effective therapy with early arthritis, when the patient is most responsive to therapy and have the most to gain.

Traditional small molecular mass drugs used to treat arthritis include, for example, chemically synthesized DMARDs: azathioprine, ciclosporin (cyclosporine A), D-penicillamine, gold salts, hydroxychloroquine, leflunomide, methotrexate (MTX), minocycline, and sulfasalazine (SSZ). Cytotoxic drugs include Cyclophosphamide.

The most common adverse events relate to liver and bone marrow toxicity (MTX, SSZ, leflunomide, azathioprine, gold compounds, D-penicillamine), renal toxicity (cyclosporine A, parenteral gold salts, D-penicillamine), pneumonitis (MTX), allergic skin reactions (gold compounds, SSZ), autoimmunity (D-penicillamine, SSZ, minocycline) and infections (azathioprine, cyclosporine A). Hydroxychloroquine may cause ocular toxicity, although this is rare, and because hydroxychloroquine does not affect the bone marrow or liver it is often considered to be the DMARD with the least toxicity. Unfortunately hydroxychloroquine is not very potent, and is usually insufficient to control symptoms on its own.

Biological agents (biologics) can be produced through genetic engineering, and include, for example, tumor necrosis factor alpha (TNFα) blockers-etanercept (Enbrel), infliximab (Remicade), adalimumab (Humira), Interleukin 1 (IL-1) blockers-anakinra (Kineret), monoclonal antibodies against B cells-rituximab (Rituxan), T cell costimulation blocker-abatacept (Orencia), Interleukin 6 (IL-6) blockers-tocilizumab (an anti-IL-6 receptor antibody) (RoActemra, Actemra)

Anti-inflammatory agents include, for example, glucocorticoids, Non-steroidal anti-inflammatory drugs (NSAIDs, most also act as analgesics). Analgesics include, for example, paracetamol (acetaminophen in US and Canada), opiates, diproqualone, and lidocaine topical.

The challenge of treating RA lies in the fact that the disease is a long term chronic illness with that can result in challenging disability for which a large range of treatments exist each of which has significant drawbacks. Many of the DMARDs subject the patients to significant side effects including increased risk for serious infections, cancer, or even autoimmune disease. Furthermore, the biologically derived drugs are very expensive, and the patient be subjected to frequent injections.

A doctor initiating therapy for a patient faces many possible options. It would be desirable to get rapid feedback once a patient starts therapy to understand whether the patient is responding to the therapy that is chosen before the clinical manifestation presents itself. Imaging is not sensitive and is expensive and many blood markers such as CRP lack sufficient sensitivity. A test that would allow the physician to rapidly determine the state of the disease would allow him or her to adjust the therapy quickly to a more effective therapy, saving the patient from additional joint damage and more effectively using the expensive therapies available.

A patient that has not experienced any acute flares since beginning treatment may in fact still be experiencing ongoing inflammatory damage to the joints that has not manifested itself clinically. A test that would allow the doctor to differentiate this state from the background would allow the therapy to be adjusted to try to bring the patient closer to a state in which no ongoing joint damage is being experienced. Specific examples of how AutoImm Load can be used in managing MS patients are described in further detail in the examples section of this document.

4. Ankylosing Spondylitis

The methods can be used to detect disease activity for Ankylosing spondylitis. Ankylosing spondylitis (AS, from Greek ankylos, bent; spondylos, vertebrae), previously known as Bechterew's disease, Bechterew syndrome, and Marie Strümpell disease, a form of Spondyloarthritis, is a chronic, inflammatory arthritis and autoimmune disease. It mainly affects joints in the spine and the sacroilium in the pelvis, causing eventual fusion of the spine. It is a member of the group of the spondyloarthropathies with a strong genetic predisposition. Complete fusion results in a complete rigidity of the spine, a condition known as bamboo spine.

The typical patient is a young male, aged 18-30, when symptoms of the disease first appear, with chronic pain and stiffness in the lower part of the spine or sometimes the entire spine, often with pain referred to one or other buttock or the back of thigh from the sacroiliac joint. Men are affected more than women by a ratio about of 3:1, with the disease usually taking a more painful course in men than women. In 40% of cases, ankylosing spondylitis is associated with an inflammation of the eye (iridocyclitis and uveitis), causing redness, eye pain, vision loss, floaters and photophobia. Another common symptom is generalised fatigue and sometimes nausea. Less commonly aortitis, apical lung fibrosis and ectasia of the sacral nerve root sheaths may occur. As with all the seronegative spondyloarthropathies, lifting of the nails (onycholysis) may occur There is no direct test to diagnose AS. A clinical examination and X-ray studies of the spine, which show characteristic spinal changes and sacroiliitis, are the major diagnostic tools. A drawback of X-ray diagnosis is that signs and symptoms of AS have usually been established as long as 8-10 years prior to X-ray-evident changes occurring on a plain film X-ray, which means a delay of as long as 10 years before adequate therapies can be introduced. Options for earlier diagnosis are tomography and magnetic resonance imaging of the sacroiliac joints, but the reliability of these tests is still unclear. The Schober's test is a useful clinical measure of flexion of the lumbar spine performed during examination.

During acute inflammatory periods, AS patients will sometimes show an increase in the blood concentration of C-reactive protein (CRP) and an increase in the erythrocyte sedimentation rate (ESR), but there are many with AS whose CRP and ESR rates do not increase so normal CRP and ESR results do not always correspond with the amount of inflammation a person actually has. Sometimes people with AS have normal level results, yet are experiencing a significant amount of inflammation in their bodies.

Ankylosing spondylitis (AS, from Greek ankylos, bent; spondylos, vertebrae), previously known as Bechterew's disease, Bechterew syndrome, and Marie Stümpell disease, a form of Spondyloarthritis, is a chronic, inflammatory arthritis and autoimmune disease. It mainly affects joints in the spine and the sacroilium in the pelvis, causing eventual fusion of the spine.

It is a member of the group of the spondyloarthropathies with a strong genetic predisposition. Complete fusion results in a complete rigidity of the spine, a condition known as bamboo spine.

There are three major types of medications used to treat ankylosing spondylitis: 1) Anti-inflammatory drugs, which include NSAIDs such as ibuprofen, phenylbutazone, indomethacin, naproxen and COX-2 inhibitors, which reduce inflammation and pain Opioid analgesics have also been proven by clinical evidence to be very effective in alleviating the type of chronic pain commonly experienced by those suffering from AS, especially in time-release formulations. 2) DMARDs such as ciclosporin, methotrexate, sulfasalazine, and corticosteroids, used to reduce the immune system response through immunosuppression; 3) TNFα blockers (antagonists) such as etanercept, infliximab and adalimumab (also known as biologics), are indicated for the treatment of and are effective immunosuppressants in AS as in other autoimmune diseases;

TNFα blockers have been shown to be the most promising treatment, slowing the progress of AS in the majority of clinical cases, helping many patients receive a significant reduction, though not elimination, of their inflammation and pain. They have also been shown to be highly effective in treating not only the arthritis of the joints but also the spinal arthritis associated with AS. A drawback, besides the often high cost, is the fact that these drugs increase the risk of infections. For this reason, the protocol for any of the TNF-α blockers include a test for tuberculosis (like Mantoux or Heat) before starting treatment. In case of recurrent infections, even recurrent sore throats, the therapy may be suspended because of the involved immunosuppression. Patients taking the TNF medications are advised to limit their exposure to others who are or may be carrying a virus (such as a cold or influenza) or who may have a bacterial or fungal infection.

AS affects produces symptoms that are very common in the healthy populations. For example, a patient presenting complaining of severe back pain need not be experiencing an AS flare but rather might just have routine back pain. The physician is forced to make a decision about whether to treat these symptoms with expensive drugs with potentially severe side effects without a very precise view into the state of the disease. CRP and ESR do not provide a very precise view of the disease status. At the same time the course of the untreated disease can result in debilitating long term spinal damage. This state of affairs leads to a difficult clinical challenge and significant overtreatment is used. The availability of an objective measure that reflects disease activity can be of great help in the management of AS patients.

B. Utility of Immune Profiling in Cancer Detection

These methods can be used to measure cancer risk. Cancer has become the leading cause of death in the industrialized world. Therefore methods of treatment of cancer are in great need. Many approaches for cancer treatment are being attempted including the development of new small molecule drugs as well as antibodies targeting the tumor.

One set of methods that has been proposed is immunotherapy. Tumor surveillance is one of the functions of cells of the immune system. There are several categories of tumor antigens that are recognized by the immune system. The first category is comprised of antigens that are novel generated by somatic mutation (point mutation or a translocation) in the tumor. Another category consists of antigens from proteins that are only expressed in male germ cells that do not express MHC molecules. The dysregulation of gene expression in many tumors may allow some of these antigens to be expressed. A third category includes antigens from proteins only expressed in particular tissues. The fourth category comprises antigens that are significantly overexpressed in the tumor tissue. Finally the fifth category includes antigens that result from abnormal posttranslational modification.

One of the properties of tumors is their ability to escape effective elimination by the immune system. It is thought that new mutations acquired in the tumor allow it to go from the equilibrium phase (where the tumor is not completely eliminated but its growth is held in check) to the escape phase where the tumor grows without effective control by the immune system. There are many mechanisms that tumors employ to escape the immune system. These mechanisms include the lack of specific antigenic peptides, or the co-stimulatory molecules that can activate T cells. Other mechanisms include the tumor secretion of factor that inhibit T cells and the creation of a tumor-induced privileged site by creating a physical barrier separating the tumor from lymphocytes. Inducing the immune system to better fight the tumor as a strategy for treating cancer is being studied and tested in multiple ways. One approach is the adoptive T cell therapy. This approach focuses on identifying T cells that are targeting tumor antigens through isolation of cells that are infiltrating the tumor and/or reacting to a specific tumor antigen. These T cells can be grown in vitro in conditions that enhance their effectiveness, like the use of IL-2 and/or antigen-presenting cells. The expanded cells are then infused back to the patient blood. Another approach is to use of retrovirus containing tumor-specific TCR. These retrovirus can be infused in the patient in special cells that later secrete the retrovirus allowing it to infect T cells that then start expressing the tumor-specific TCR. Finally a common approach is the use of vaccination. The premise of this approach of therapy is that immunization of the patient with one or more of the tumor antigens will stimulate the immune system ability to fight the tumor. Immunization is often done with the use of an adjuvant like Bacille Calmette-Guerin (BCG). This approach has been successful in preventing viral-induced cancer as evident by the ability to prevent cervical cancers induced by HPV-16 and HPV-18. However this has been less successful in the treatment of other tumors.

Much of the improvement in mortality because of cancer has come about due to the availability of better early detection methods leading for instance to reduced rates of mortality in breast cancer and cervical cancers. The mutability of tumors makes their early treatment much more effective than when they are detected late. Traditionally. looking for cancer detection biomarkers usually involved looking for markers that are highly expressed in the cancer and are at low level or absent in the normal tissue. This has led to the identification of several tumor markers, like PSA. One problem with early detection of in cancer is that the greatest value in for cancer detection occurs when detection of biomarker is most difficult, i.e., the tumor is very small. Therefore in order to have an effective cancer detection biomarker that can distinguish patients with small tumors from those that do not, there needs to be a tremendous difference in expression between the tumor and the normal tissue due to the large difference in size between the tumor and the normal tissue. Additionally the marker needs to "spill" efficiently to the blood or other body fluid to allow detection using a non-invasive technique.

This invention teaches a novel mechanism for cancer detection using the immune cell response. In this view cancer detection is not achieved by the detection of a marker produced by the tumor itself but by the immune system response to the tumor. Specifically the profile of TCR and/or BCR can provide an insight on whether the body is mounting a response to a tumor or not. This can ameliorate some of the issues with current biomarkers. First the immune response is an amplification signal that can be easier to detect. Second lymphocytes pass through the blood regularly and hence the relevant biomarker may readily present and detectable in peripheral blood than traditional tumor biomarker. Finally the problem of "background" biomarker material generated by the normal tissue is greatly reduced. The great diversity of T and/or B cells provide a way to detect the relevant biomarker with high sensitivity and specificity, particularly with the recent availability of high throughput methods for DNA sequencing. The approach of using the immune system response to cancer to detect it leverages the foundations laid to this field by the promise of immunotherapy. However the risk for the two applications is probably quite different. To use the immune response to cancer for its detection does not require that the specific clonotype be effective in treating the tumor but rather that it is associated with the immune response to the tumor.

Another embodiment of this invention contemplates the combination of the immune profiling tests with other markers that are already in use for the detection of cancer to allow tests with greater sensitivity and specificity. Other molecular identifiers or markers can be used in computing the Load algorithm or for determining the disease state. Molecular identifiers can include nucleic acids, proteins, carbohydrates, and lipids, and expression profiles of nucleic acids or proteins. The molecular identifiers can be of human or non-human origin (e.g., bacterial). The identifiers or markers can be determined by techniques that include, for example, comparative genomic hybridization (CGH), chromosomal microarray analysis (CMA), expression profiling, DNA microarray, high-density oligonucleotide microarray, whole-genome RNA expression array, peptide microarray, enzyme-linked immunosorbent assay (ELISA), genome sequencing, copy number (CNV) analysis, small nucleotide polymorphism (SNP) analysis, immunohistochemistry, in-situ hybridization, fluorescent in-situ hybridization (FISH), PCR, Western blotting, Southern blotting, SDS-PAGE, gel electrophoresis, and Northern blotting.

C. Utility of Immune Profiling in Transplant Medicine

These methods can be used to detect immune rejection of transplanted organs. Transplantation of organs have become an integral part of medicine with over 25,000 solid organ (kidney, liver, heart, pancreas, and lung) transplants and more than 15,000 bone marrow transplants occurring in the US per year. These are generally complicated procedures done at tertiary care centers. To minimize the risk of transplant rejection, patients are often placed on immunosuppression for extended periods of time subjecting them to the risk of cancer and infections. Furthermore many transplants are rejected either acutely or years after the transplantation. In spite of these issues organ transplant remains an essential treatment modality as patients with organ failures have few other alternatives.

Solid organ transplant rejection primarily occurs due to response of the adaptive immune system to the transplanted organ. This is due to the presence of alloantigens in the graft that are recognized by the host's immune system, The rejection can occur in three different phases. The first is the hyper-acute phase within minutes of the transplant where preformed antibodies mount a response to the graft. The second is the acute rejection that occurs in first weeks or months after the transplant. The last is chronic rejection that can occur years after the transplantation. Given these risks care has been taken to minimize the immunogenic differences between the donor and recipient. For example the risk of the hyperacute reaction is greatly reduced when the donor and recipient are matched for their ABO subtypes as well as tested for cross matching (determining whether the recipient has antibodies that react with the leukocytes of the donor). Similarly careful matching for the Major HistoCompatability (MHC) is done to reduce acute rejection. However given that MHC molecules are very polymorphic it is very hard to find to identify a perfect match. Monozygotic twins have a perfect MHC matching. Similarly ¼ siblings are expected to have a perfect MHC match. Unrelated individuals that have the same detected alleles per the clinical test often have differences due to other polymorphic sites that are not tested in routine clinical practice. However even with perfect MHC matching from siblings, there is still a significant risk of rejection due to the existence of minor histocompatibility antigens, and indeed acute rejection is very common occurring to more than half of the grafts.

One might imagine that more aggressive testing of the MHC locus as well as identification and matching the minor histocompatibility antigens would significantly improve the graft rejection and possibly survival rates. While that might be true the limited numbers of available donor organs available makes this task impractical as more aggressive testing may significantly delay the identification of an appropriate graft to be used for each patient. Therefore, much of the progress that has occurred in the transplantation field was in the use of immunosuppressive agents to prevent and treat rejection. Currently many drugs are utilized for this purpose including: Azathioprine, corticosteroids, Cyclosporine, Tacrolimus, Mycophenolate Acid, Sirolimus, Muromonab-CD3, Monoclonal Anti-CD25 Antibody, Monoclonal Anti-CD25 Antibody, and Calcineurin inhibitors.

Bone marrow transplant is most frequently used for leukemia and lymphoma treatment. Typically the recipient undergoes an aggressive regimen of radiation and/or chemotherapy to decrease the load of the tumor before the transplantation. Mature T cells from the donor can attack some of the host tissues in the inverse rejection that is called Graft Vs Host Disease (GVHD). This is often manifested by rash, diarrhea, and liver disease. Careful matching of MHC can ameliorate but not eliminate this problem. One solution is the depletion of the donor bone marrow in vitro of mature T cells that are ultimately responsible for GVHD. One problem with this is that the same phenomenon that causes GVHD may be responsible for some of the therapeutic effect of bone marrow transplant through the graft vs. leukemia effect where donor T cells attack the remaining cancer cells. In addition depletion of donor T cells can expose to patient to the risk of being immunodeficient. Therefore the risk and benefits have to be balanced when considering these approaches. Patients are therefore often treated with immunosuppressants to prevent as well as treat GVHD.

Current management of bone marrow but even more so for solid organ transplantation rely heavily on the treatment with strong immunosuppressive agents. However given that these drugs have significant risks they are used in a manner to balance risk and benefit. However given that the risk for a specific patient at a particular time is not well understood patients are treated with the dose where risk and benefits are balanced for the average patient. Tests that can predict future rejection events may potentially be very helpful in tailoring treatment to the patients at the appropriate times they need them. This may result in reduction in the immunosuppressive doses or some of the patients while improving the rate of rejection and hopefully graft survival.

Another embodiment of this invention contemplates the combination of the immune profiling tests with other markers that are already in use for the detection of transplant rejection to allow tests with greater sensitivity and specificity. Other molecular identifiers or markers can be used in computing the Load algorithm or for determining the disease state. Molecular identifiers can include nucleic acids, proteins, carbohydrates, and lipids, and expression profiles of nucleic acids or proteins. The molecular identifiers can be of human or non-human origin (e.g., bacterial). The identifiers or markers can be determined by techniques that include, for example, comparative genomic hybridization (CGH), chromosomal microarray analysis (CMA), expression profiling, DNA microarray, high-density oligonucleotide microarray, whole-genome RNA expression array, peptide microarray, enzyme-linked immunosorbent assay (ELISA), genome sequencing, copy number (CNV) analysis, small nucleotide polymorphism (SNP) analysis, immunohistochemistry, in-situ hybridization, fluorescent in-situ hybridization (FISH), PCR, Western blotting, Southern blotting, SDS-PAGE, gel electrophoresis, and Northern blotting.

D. Utility of Immune Profiling in the Treatment of Infection

These methods have utility in guiding the treatment of infections particularly when these infections can exist in active and latent states. The advent of antibiotics for the treatment of infectious disease over the past century has made a great impact on life expectancy. Over the past decade molecular diagnostics techniques have taken a rapidly increasing role in the diagnosis and management of infectious disease. The excellent sensitivity and specificity provided by nucleic acid amplification has enabled the application of these techniques to an increasing number of applications. Many of the applications are used for the diagnostic evaluation of the presence or absence of infectious agents. For example the testing of sexually transmitted diseases is often done by a molecular testing employing nucleic acid amplification technique. Another set of application involve the assessment of the "load" of the infection in a patient with an already diagnosed infectious agent. An example of that is the assessment of HIV viral load in patients already diagnosed with AIDS. This test helps the physician in determining whether the state of the patient's disease and hence can provide guidance on the effectiveness of the treatment regimen being used.

It is sometimes helpful not only to consider the level of the infectious agent but also the immune response to the infectious agent. One example where the immune response to the infection is used routinely in clinical practice is in hepatitis B. One aspect of hepatitis B testing relies on detecting the infectious agent through detection of hepatitis B antigens of by a nucleic acid amplification assay. In addition it is common in routine clinical practice to test for the presence of different antibodies that target the hepatitis B virus. The presence of anti-HBc IgM usually occurs in an acute infection setting, the appearance of anti-HBc IgG indicates the infection is chronic. Similarly the emergence of anti-HBs antibody signals clearing of the infection.

In one embodiment of this invention the value of the assessing the immune response to an infection is harnessed along with the sensitivity and specificity of the molecular testing. This can be particularly useful for infectious diseases that are chronic where the infectious agent remains latent in the body. The profile of the TCR and/or BCR can be used to assess the immune response to an infection. Sequencing can be used to obtain a profile of the TCR and/or BCR allowing the detection of particular clonotypes with high sensitivity and specificity. To determine the specific clonotypes that correlate with disease several approaches are conceived.

Another embodiment of this invention contemplates the combination of the immune profiling tests with other markers that are already in use for the detection of infectious agents to allow tests with greater sensitivity and specificity. Other molecular identifiers or markers can be used in computing the Load algorithm or for determining the disease state. Molecular identifiers can include nucleic acids, proteins, carbohydrates, and lipids, and expression profiles of nucleic acids or proteins. The molecular identifiers can be of human or non-human origin (e.g., bacterial). The identifiers or markers can be determined by techniques that include, for example, comparative genomic hybridization (CGH), chromosomal microarray analysis (CMA), expression profiling, DNA microarray, high-density oligonucleotide microarray, whole-genome RNA expression array, peptide microarray, enzyme-linked immunosorbent assay (ELISA), genome sequencing, copy number (CNV) analysis, small nucleotide polymorphism (SNP) analysis, immunohistochemistry, in-situ hybridization, fluorescent in-situ hybridization (FISH), PCR, Western blotting, Southern blotting, SDS-PAGE, gel electrophoresis, and Northern blotting.

E. Utility of Immune Profiling in the Treatment of Aging Patients

These methods have utility in monitoring the state of the immune system in the aged. Older people suffer from a decline in the immune system called immunosenescence that affects their ability to respond to infections and to raise effective responses to vaccines (Weinberger et al., 2008). This is apparent from the high mortality rates due to pneumonia in the elderly (Office for National Statistics, 2005), and their susceptibility to hospital-acquired infections, such as Clostridium difficile and methicillin-resistant Staphylococcus aureus (Health Protection Agency, 2008). Furthermore the decline in the immune system ability is thought to explain the increased rate of cancers in the elderly. In addition immunosenescence may contribute to other major diseases of the elderly with significant component of inflammatory processes, like Alzheimer and heart disease. An ability to predict which individuals are most at risk for these deadly outcomes would be useful to geriatrics physicians as they make clinical decisions about vaccination, aggressive treatment of infections and hospitalization.

Many aspects of the innate and adaptive immune system are altered in immunosenescence. T cells lose responsiveness, macrophages have a decreased antigen-presenting capacity and altered cytokine secretion, natural killer cells have reduced toxicity, follicular dendritic cells cannot present antigen as efficiently, and neutrophils lose phagocytic ability. There is smaller pool of naïve T and B cells and an increase in the memory and effector pool leading to a reduced diversity of T and B cell repertoires leading to the reduction of the ability of the adaptive immune system to respond to new antigens. In particular T cell repertoires that are associated with cytomegalovirus (CMV) are greatly increased and as much as 45% of the total T cell repertoire may be devoted to it. It has been noted that these expansions are less pronounced in centenarians.

Studies have suggested that immune markers can predict survival in the elderly. The degree of diversity of the B cell repertoire has been shown to predict survival in the elderly at least in one population. Even though these global differences in TCR and BCR diversity were shown to predict clinical outcomes but these markers lack specificity. Deeper analysis of the repertoire data may provide significantly more prediction accuracy. For example, expansions responsive to CMV may have a different significance than other expansions.

In one embodiment of this invention, RNA from the T and B cells found in peripheral blood can be collected from a longitudinal cohort of aging patients whose clinical histories are followed for several years. The TCRα and TCRβ genes and the IgH, IgK and IgL genes can be amplified in each of these cohorts at several time points in their clinical histories. Profiles of patients with long survival will be compared to patients with short survival. First, global measure of diversity can be obtained. This will include not only the number of different clonotypes identified but also their diversity. For example, is the V, D, J segment usage the same in the two groups or is one group more restricted in its usage? For example two samples may have the same number of independent clonotype but the clonotypes for one of the two samples do not cover many of the V segments. It is logical to expect that this sample would be less versatile in responding to a new antigen compared with the other sample whose clonotypes are distributed among all the V segments.

In addition to global diversity it will be determined whether expanded clonotypes in patients who had a long survival can be distinguished on the basis of some sequence parameter compared to clonotypes in patients who had a short survival. This approach can be supplemented by looking at clonotypes that respond to specific antigens. For example given the available evidence identification of CMV responsive clonotypes can have predictive power. Capturing T cells clonotypes that are CMV reactive in a discovery study can be done from a set of elderly as well as healthy patients. Sequences of these clonotypes can be studied to identify parameters that distinguish them from other clonotypes. Using this predictive algorithm of CMV clonotypes with the longitudinal cohort described above it can be assessed whether adding this information can add to the ability to predict the patient who survive for a long time from that who does not.

Another embodiment of this invention contemplates the combination of the immune profiling tests with other markers that are already in use for the detection of health in the aging population to allow tests with greater sensitivity and specificity. Other molecular identifiers or markers can be used in computing the Load algorithm or for determining the disease state. Molecular identifiers can include nucleic acids, proteins, carbohydrates, and lipids, and expression profiles of nucleic acids or proteins. The molecular identifiers can be of human or non-human origin (e.g., bacterial). The identifiers or markers can be determined by techniques that include, for example, comparative genomic hybridization (CGH), chromosomal microarray analysis (CMA), expression profiling, DNA microarray, high-density oligonucleotide microarray, whole-genome RNA expression array, peptide microarray, enzyme-linked immunosorbent assay (ELISA), genome sequencing, copy number (CNV) analysis, small nucleotide polymorphism (SNP) analysis, immunohistochemistry, in-situ hybridization, fluorescent in-situ hybridization (FISH), PCR, Western blotting, Southern blotting, SDS-PAGE, gel electrophoresis, and Northern blotting.

F. Utility of Immune Profiling in the Administration of Vaccines

These methods have utility in the administration of vaccines. The use of vaccination has led to a great reduction in the rate of infections of multiple organisms. One infectious disease that continues to have a significant health impact with over 30,000 deaths a year in the US is Influenza. Influenza vaccination has to be done yearly as the strain mutates rapidly. Most of the severe sequelae of the disease occur in the elderly. Unfortunately the elderly often experience immunosenescence rendering them inadequately responsive to the vaccination.

In order to distinguish patients who are responsive to vaccination from those that are not, a discovery study needs to be performed. In this population pre and (at one or more set time) post vaccination blood samples are available for a cohort of Influenza vaccinated patients with known Influenza outcome (i.e., were they later protected from the infection or not). TCR and/or BCR sequence can be obtained from these samples. Clonotypes that are enriched after vaccination in each patient are determined. Enriched clonotypes in patients who responded to the vaccination are then compared to a control set of clonotypes (e.g., the rest of the clonotypes in the same set of patients) to distinguish the correlating clonotypes from other clonotypes. The algorithm to predict these clonotypes is then used to predict correlating clonotypes among patients who did not respond to the vaccination. Patients who did not respond may generate the same type of clonotypes as those that responded but at lower levels. Alternatively it might be that non-responders generate a distinct class of clonotypes. The number of correlating clonotypes identified in the non-responder may distinguish these two possibilities.

With the correlating clonotypes identified, an algorithm is then built to generate a score for predicting likelihood of immunization. Data from the profiles of the vaccine-responders and those that do not respond are utilized to generate this algorithm. This algorithm can then be used to predict the likelihood of immunization in the next patient using the predicted correlating clonotypes from a sample obtained after immunization. The prediction is done through the application of another algorithm that has also been generated in the discovery study. It can optionally be aided (or substituted) by data from the pre-calibration to limit the search for correlating clonotypes to those that were enriched after immunization.

Another embodiment of this invention contemplates the combination of the immune profiling tests with other markers that are already in use for the detection of response to vaccination to allow tests with greater sensitivity and specificity. Other molecular identifiers or markers can be used in computing the Load algorithm or for determining the disease state. Molecular identifiers can include nucleic acids, proteins, carbohydrates, and lipids, and expression profiles of nucleic acids or proteins. The molecular identifiers can be of human or non-human origin (e.g., bacterial). The identifiers or markers can be determined by techniques that include, for example, comparative genomic hybridization (CGH), chromosomal microarray analysis (CMA), expression profiling, DNA microarray, high-density oligonucleotide microarray, whole-genome RNA expression array, peptide microarray, enzyme-linked immunosorbent assay (ELISA), genome sequencing, copy number (CNV) analysis, small nucleotide polymorphism (SNP) analysis, immunohistochemistry, in-situ hybridization, fluorescent in-situ hybridization (FISH), PCR, Western blotting, Southern blotting, SDS-PAGE, gel electrophoresis, and Northern blotting.

G. Utility of Immune Profiling in the Monitoring of Immune Hypersensitivity (Allergy)

The adaptive immune system has evolved to respond to antigens that are associated with pathogens. As is in the case of autoimmune diseases, the immune system can sometimes have the wrong target. Whereas in autoimmune diseases the immune system targets self antigen, in hypersensitivity reactions it mounts a response to harmless stimuli like medications, dust, and food. Hypersensitivity is very common with as many as 50% of the US population having allergy to an environmental stimulus, and it is caused by mechanisms. Hypersensitivity is divided into 4 types. Type I hypersensitivity is the immediate type hypersensitivity and is mediated by IgE. Type II is often due to IgG antibody binding to cell surface-associated antigen. For example a harmless drug that binds to the surface of the cell can make the cell a target for anti-drug IgG in patients who happened to have these antibodies. Type III is caused by deposition of antigen-antibody complexes on tissues. This occurs for example when the amount of antigen is large resulting in small immune complexes that can't be cleared efficiently and are instead deposited on blood vessel walls. Type IV sensitivity is a delayed type hypersensitivity mediated by T cells. Type I and type IV have the highest impact on human health.

In Type I hypersensitivity reaction the patient becomes sensitized to a harmless antigen (allergen) by producing IgE antibody against it. Later exposure to the allergen induces the activation of IgE-binding cells, such as mast cells and basophils. Once activated these cells cause the allergic reaction through inducing an inflammatory process by secreting stored chemicals and synthesizing cytokines, leukotrienes, and prostaglandins. The dose and the route of entry of the allergen determines the magnitude of the allergic reaction that can range from symptoms of allergic rhinitis to the life-threatening circulatory collapse in anaphylaxis. Often the acute Type I reaction is later followed by another late phase that is plays a role in many of the resulting pathological processes. The late phase of recruitment of T helper cells and other inflammatory cells is essentially a Type IV hypersensitivity reaction. Some Type I allergic reactions include seasonal rhinoconjunctivitis (hayfever), food allergy, drug-induced anaphylaxis, atopic dermatitis (eczema), and asthma. These are very common conditions with rising prevalence causing significant costs as well as morbidity and mortality. For example, Asthma is a chronic disease that inflicts ~7% of the US population causing ~4,000 deaths a year. Some of these diseases have some related aspects. For example, patients with atopic dermatitis are at significantly increased risk to have asthma. Food allergy can cause vomiting and diarrhea but can also result in anaphylaxis in a significant number of patients—30,000 cases resulting in ~200 deaths per year in the US. Some of the same allergen that activates submucosal mast cells in the nose causing symptoms of allergic rhinitis can also activate mast cells in the lower airways causing bronchial constriction, a typical symptom of asthma. Some Type IV hypersensitivity reactions are contact dermatitis (e.g., poison ivy), chronic rhinitis, chronic asthma, and celiac disease. Celiac disease is a chronic disease caused by a non-IgE mediated food allergy. It is a disease of the small intestine caused by the allergic response against gluten, a component present in wheat and other foods. Over 95% of patients celiac patients have a specific MHC class II allele, the HLA-DQ2.

Treatment of hypersensitivity reactions differs, but they often had two aspects: the acute treatment and chronic management or prevention. Some of these conditions can be life threatening (anaphylaxis, and acute asthma) and involve immediate medical attention. The chronic management in general it involves trying to avoid the specific allergen. This may be effective when the allergen can be clearly identified (e.g., allergy to nuts), but this can be difficult when the allergen is present widely in the environment, like pollen or dust. Therefore chronic treatment with medications is often utilized for some of these diseases (e.g., asthma and allergic rhinitis). The level of effectiveness of the treatment management is ultimately tested when the patient is re-exposed to the allergen(s). Therefore some patients may be subject to over- or under-treatment. Ideally a test that assesses the disease activity and the degree to which the patient is prone to mount a hypersensitivity response would be available. Such a test would allow the tailoring of treatment to the individual patient needs.

EXAMPLES

Example 1

Figure 1:
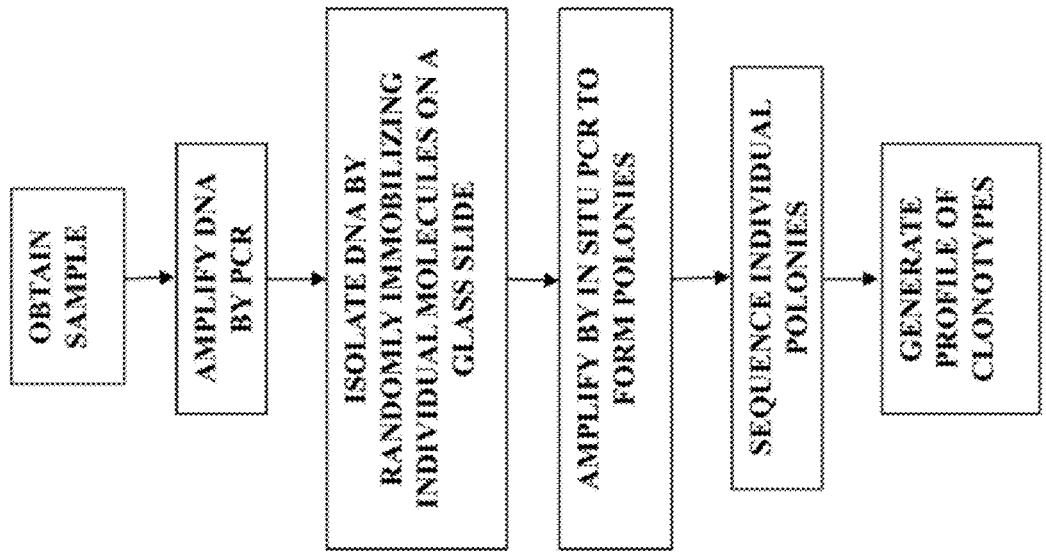
FIG. 1 is a flow diagram of an embodiment of a method of the provided invention for determining clonotype profiles.

Determining the Sequence of Recombined DNA in a Subject with an Autoimmune Disease A blood sample is taken from a patient with an autoimmune disease. CD4+ and CD8+ cells are isolated from the blood sample using antibody-coated magnetic beads. PCR is used to amplify the full variable region of the T cell receptor β gene. The amplified fragments are subcloned into vectors and transformed in bacteria to isolate the DNA fragments. The bacteria are grown to amplify the DNA, and dideoxy sequencing is used to sequence the variable regions of the T cell receptor gene to identify the clonotypes. The sequencing information is used to generate a clonotype profile for the patient. A similar method is shown in FIG. 1.

Example 2

Determining the State of an Autoimmune Disease

A sample of cerebral spinal fluid (CSF) and blood is taken from a patient with an episode peak of multiple sclerosis. CD4+ cells are isolated from the CSF and blood, and the CDR3 of the T cell receptor β gene is amplified by PCR. The amplified fragments are subcloned into vectors and transformed in bacteria to isolate the DNA fragments. The bacteria are grown to amplify the DNA, and dideoxy sequencing is used to sequence the variable regions of the T cell receptor β gene to identify the clonotypes. The sequencing information is used to generate a clonotype profile for the patient.

Another blood sample is taken when the patient is at a relatively inactive state of multiple sclerosis. The same procedure as above is repeated to generate a clonotype profile. Pathological clonotypes are identified as those that are high at the peak episode and went down significantly at the inactive state. Another blood sample is taken from the patient at a later state. At this time only a fraction of the T cell receptor β gene CDR3 regions are amplified and then sequenced. This subset contains the pathological clonotypes. The level of the various clonotypes is determined to assess the disease state of the patient.

Example 3

TCRβ Repertoire Analysis

Amplification and Sequencing Strategy

To study amplification of the TCR repertoire, TCRβ chains will be analyzed. The analysis will include amplification, sequencing, and analyzing the TCRβ sequences. One primer AGCGACCTCGGGTGGGAACA (SEQ ID NO: 135) is complementary to a common sequence in Cβ1 and Cβ2, and there are 34 V primers (Table 1) capable of amplifying all 48 V segments. Cβ1 or Cβ2 differ from each other at position 10 and 14 from the J/C junction. The primer for Cβ1 and Cβ2 will end at position 16 bp and should have no preference for Cβ1 or Cβ2.

The 34 V primers are modified from an original set of primers published by the BIOMED-2 group in order to amplify all 48 V segments and all their published alleles as defined by the international ImMunoGeneTics information system (http://imgt.cines.fr/).

The BIOMED-2 primers have been used in multiplex in order to identify clonality in lymphoproliferative diseases.

TABLE 1

Primer sequences complementary to the different V families.

| V segment family | Primer sequence | SEQ ID NO: |
|---|---|---|
| V20-1 | AACTATGTTTTGGTATCGTCAGT | 1 |
| V29-1 | TTCTGGTACCGTCAGCAAC | 2 |
| V9, 5-1, 5-6, 5-5, 5-8, 5-4A | AGTGTATCCTGGTACCAACAG | 3 |
| V9, 5-1, 5-6, 5-5, 5-8, 5-4B | AGTGTGTACTGGTACCAACAG | 4 |
| V9, 5-1, 5-6, 5-5, 5-8, 5-4C | ACTGTGTCCTGGTACCAACAG | 5 |
| V9, 5-1, 5-6, 5-5, 5-8, 5-4D | AGTGTGTCCTGGTACCAACAG | 6 |
| V9, 5-1, 5-6, 5-5, 5-8, 5-4E | TCTGTGTACTGGTACCAACAG | 7 |
| V7-3, 7-6, 7-9, 7-2, 7-4A | CCCTTTACTGGTACCGACAG | 8 |
| V7-3, 7-6, 7-9, 7-2, 7-4B | GCCTTTACTGGTACCGACAG | 9 |
| V7-3, 7-6, 7-9, 7-2, 7-4C | CCCTTTACTGGTACCGACAAA | 10 |
| V7-8, 16A | TTTTGGTACCAACAGGTCC | 11 |
| V7-8, 16B | TTTTGGTACCAACAGGCCC | 12 |
| V 7-7 | AACCCTTTATTGGTATCAACAG | 13 |
| V4-1, 4-3, 4-2A | CGCTATGTATTGGTACAAGCA | 14 |
| V4-1, 4-3, 4-2B | GGCAATGTATTGGTACAAGCA | 15 |
| V12-3, 12-4, 12-5 | TTTCTGGTACAGACAGACCATGA | 16 |
| V3-1 | TACTATGTATTGGTATAAACAGGACTC | 17 |
| V25-1 | CAAAATGTACTGGTATCAACAA | 18 |
| V28, 10-3, 6-2, 6-3, 6-1, 6-6, 24-1A | ATGTTCTGGTATCGACAAGACC | 19 |
| V28, 10-3, 6-2, 6-3, 6-1, 6-6, 24-1B | ATGTACTGGTATCGACAAGACC | 20 |
| V6-4, 6-9A | TGCCATGTACTGGTATAGACAAG | 21 |
| V6-4, 6-9B | ATACTTGTCCTGGTATCGACAAG | 22 |
| V10-1, 10-2, 6-5, 6-9, 6-8, 27A | ATATGTTCTGGTATCGACAAGA | 23 |
| V10-1, 10-2, 6-5, 6-9, 6-8, 27B | ATATGTCCTGGTATCGACAAGA | 24 |
| V10-1, 10-2, 6-5, 6-9, 6-8, 27C | ACATGTCCTGGTATCGACAAGA | 25 |
| V14 | TAATCTTTATTGGTATCGACGTGT | 26 |
| V19 | GCCATGTACTGGTACCGACA | 27 |
| V18 | TCATGTTTACTGGTATCGGCAG | 28 |
| V30 | CAACCTATACTGGTACCGACA | 29 |
| V11-1, 11-3, 11-2A | CATGCTACCCTTTACTGGTACC | 30 |
| V11-1, 11-3, 11-2B | CACAATACCCTTTACTGGTACC | 31 |
| V2 | ATACTTCTATTGGTACAGACAAATCT | 32 |
| V13 | CACTGTCTACTGGTACCAGCA | 33 |
| V15 | CGTCATGTACTGGTACCAGCA | 34 |

The use of the primers for amplification was tested with 34 synthetic sequences. The synthetic sequences contained on one side the sequence of one of the oligonucleotides and on the other side the complement of the C primer. In between the two primers was 6 bp corresponding to the restriction enzyme site Cla I. All the synthetic sequences were amplified with the appropriate primers, and it was demonstrated through Cla I digestion that the amplification products were the result of amplifying the synthetic sequences and not through formation of primer dimers.

The Illumina Genome Analyzer is the sequencing platform of choice. In each lane, ~15 million reads can be done. Twelve human and 96 mouse samples per lane will be run, and sequence tags will be used to distinguish reads of one sample from those of another. A two-stage amplification screen can be performed, as illustrated in FIG. 2. As shown in FIG. 2A, the primary PCR will use on one side a 20 bp primer whose 3' end is 16 bases from the J/C junction and is perfectly complementary to Cβ1 and the two alleles of Cβ2. In the secondary PCR, on the same side of the template, a primer is used that has at its 3' end the sequence of the 10 bases closest to the J/C junction, followed by 17 bp with the sequence of positions 15-31 from the J/C junction, followed by the P5 sequence. This primer is referred to as C10-17-P5. P5 plays a role in cluster formation. When the C10-17-P5 primer anneals to the template generated from the first PCR, a 4 bp loop (position 11-14) is created in the template, as the primer hybridizes to the sequence of the 10 bases closest to the J/C junction and bases at positions 15-31 from the J/C junction. The looping of positions 11-14 eliminates differential amplification of templates carrying Cβ1 or Cβ2. Ultimately, sequencing is done with a primer complementary to the sequence of the 10 bases closest to the J/C junction and bases at positions 15-31 from the J/C junction (this primer will be called C'). C10-17-P5 primer can be HPLC purified in order to ensure that all the amplified material has intact ends that can be efficiently utilized in the cluster formation.

In FIG. 2B, the length of the overhang on the V primers is shown to be 14 bp. The first PCR may be helped with shorter overhang. On the other hand for the sake of the second PCR, it can be advantageous to have the overhang in the V primer used in the first PCR as long as possible because the second PCR will be priming from this sequence. A very inefficient priming in the second PCR may cause limitation in the representation in the final data.

A minimum size of the overhang that supports an efficient second PCR was investigated. Two series of V primers (for two different V segments) with overhang sizes from 10 to 30 with 2 bp steps were made. Using the appropriate synthetic sequences, the first PCR was performed with each of the primers in the series and gel electrophoresis was performed to show that all amplified. In order to measure the efficiency of the second PCR amplification SYBR green real time PCR was performed using as a template the PCR products from the different first PCR reactions and as primers Read2-tag1-P7 and Read2-tag2-P7. A consistent picture emerged using all 4 series of real time data (2 primary PCRs with two different V segments and two secondary PCR with different primers containing two different tags). There was an improvement in efficiency between overhang sizes 10 and 14 bp. However there was little or no improvement in efficiency with an overhang over 14 bp. The efficiency remained high as the overhang became as small as 14 bp because of the high concentration of primers allowing the 14 bp to be sufficient priming template at a temperature much higher than their melting temperature. At the same time the specificity was maintained because the template was not all the cDNA but rather a low complexity PCR product where all the molecules had the 14 bp overhang.

As illustrated in FIG. 2B, the primary PCR will use 34 different V primers that anneal to the other side of the template and contain a common 14 bp overhang on the 5' tail. The 14 bp is the partial sequence of one of the Illumina sequencing primers (termed the Read 2 primer). The second amplification primer on the same side includes P7 sequence, a tag, and Read 2 primer sequence (this primer is called Read2_tagX_P7). The P7 sequence is used for cluster formation. Read 2 and its complement are used for sequencing the V segment and the tag respectively. A set of 96 of these primers with tags numbered 1 through 96 were created (see below). These primers can be HPLC purified in order to ensure that all the amplified material has intact ends that can be efficiently utilized in the cluster formation.

As mentioned above, the second stage primer, C-10-17-P5 (FIG. 2A) has interrupted homology to the template generated in the first stage PCR. The efficiency of amplification using this primer has been validated. An alternative primer to C-10-17-P5, termed CsegP5, has perfect homology to the first stage C primer and a 5' tail carrying P5. The efficiency of using C-10-17-P5 and CsegP5 in amplifying first stage PCR templates was compared by performing real time PCR. In several replicates, it was found that PCR using the C-10-17-P5 primer had little or no difference in efficiency compared with PCR using the CsegP5 primer.

The molecule resulting from the 2-stage amplification illustrated in FIG. 2 will have the structure typically used with the Illumina sequencer as shown in FIG. 3. Two primers that anneal to the outmost part of the molecule, Illumina primers P5 (AATGATACGGCGACCACCGAG (SEQ ID NO: 35)) and P7 (CAAGCAGAAGACGGCATACGAGAT (SEQ ID NO: 36)) will be used for solid phase amplification of the molecule (cluster formation). Three sequence reads are done per molecule. The first read of 100 bp is done with the C' primer, which has a melting temperature that is appropriate for the Illumina sequencing process. The second read is 6 bp long only and will be solely for the purpose of identifying the sample tag. It is generated using the Illumina Tag primer (AGATCGGAAGAGCACACGTCTGAACTCCAGTCAC (SEQ ID NO: 37)). The final read is the Read 2 primer, an Illumina primer with the sequence GTGACTGGAGTTCAGACGTGTGCTCTTCCGATCT (SEQ ID NO: 38). Using this primer, a 100 bp read in the V segment will be generated starting with the 1st PCR V primer sequence.

A set of 6 bp sequence tags to distinguish different samples run in the same sequencing lane was designed, where each tag is different from all the other tags in the set by at least 2 differences. The 2 differences prevent misassignment of a read to the wrong sample if there is a sequencing error. The alignment done to compare the tags allowed gaps and hence one deletion or insertion error by sequencing will also not assign the read to the wrong sample. Additional features in selecting the tags was to limit single base runs (4 A or T and 3 G or C) as well as no similarity to the Illumina primers. In total 143 tags were generated with the premise that 96 of them will be used.

Real time PCR has been performed with all 34 different primers using cDNA obtained from a blood sample. Different Ct values were obtained for the different primers. Each of the PCR products were run by gel electrophoresis and demonstrated a single band. In addition all 34 primers were pooled and a PCR was performed and again a single PCR band was obtained.

Amplification Optimization

The multiplex amplification can use all the V segments. One issue in amplification of different sequences is the relative amplification efficiency of the different sequences and the preservation of the initial relative quantity of the different sequences in the final amplified material. The relative amplification efficiency can be subdivided into different efficiencies of the distinct primer sequences as well as the different efficiencies of amplification of different sequences using the same primer. Efficiency difference can be due to distinct primer sequences. The reaction will be optimized to attempt to get amplification that maintains the relative abundance of the sequences amplified by different V segment primers. Some of the primers are related, and hence many of the primers may "cross talk," amplifying templates that are not perfectly matched with it. The conditions can be optimized so that each template can be amplified in a similar fashion irrespective of which primer amplified it. In other words if there are two templates, then after 1,000 fold amplification both templates can be amplified approximately 1,000 fold, and it does not matter that for one of the templates half of the amplified products carried a different primer because of the cross talk. In subsequent analysis of the sequencing data the primer sequence will be eliminated from the analysis, and hence it does not matter what primer is used in the amplification as long as the templates are amplified equally.

Since the amount of each template is not known in cDNA, set of standards have been generated using the 34 singleplex PCR reaction from cDNA. The product in each of these reactions comprised a plurality of sequences with one V primer. The different products were carefully quantitated to create a set of standards at the same concentration. A pool of all 34 primers was used and 34 real time PCR were performed using the pool of primers and each of the standard sequences as a template. Ideally all the 34 standards will show equal efficiency of amplification by real time PCR. That suggests that each sequence is amplified equally even though the presence of cross talk makes it unclear what primers are carrying out the amplification. This optimization is consistent with the goal of having equal amplification irrespective of the actual primers that is incorporated in the amplification product. Increasing the total primer pool concentration significantly reduced the dynamic range as expected from increasing the efficiency of the amplification. Furthermore for templates that seemed to amplify more efficiently than the average, the concentration of their perfectly matched primer in the pool was decreased. Conversely for templates that were inefficiently amplified the concentration of their perfectly matched primer was increased. This optimization demonstrated that all the templates are amplified within 2 fold of the average amplification.

Ideally the primary PCR will have a small number of cycles to minimize the differential amplification by the different primers. The secondary amplification is done with one pair of primers and hence the issue of differential amplification is minimal. One percent of the primary PCR is taken directly to the secondary PCR. Thirty-five cycles (equivalent to ~28 cycles without the 100 fold dilution step) used between the two amplifications were sufficient to show a robust amplification irrespective of whether the breakdown of cycles were: one cycle primary and 34 secondary or 25 primary and 10 secondary. Even though ideally doing only 1 cycle in the primary PCR may decrease the amplification bias, there are other considerations. One aspect of this is representation. This plays a role when the starting input amount is not in excess to the number of reads ultimately obtained. For example, if 1,000,000 reads are obtained and starting with 1,000,000 input molecules then taking only representation from 100,000 molecules to the secondary amplification would degrade the precision of estimating the relative abundance of the different species in the original sample. The 100 fold dilution between the 2 steps means that the representation will be reduced unless the primary PCR amplification generated significantly more than 100 molecules. This translate to a minimum 8 cycles (256 fold), but more comfortably 10 cycle (~1,000 fold). The alternative to that is to take more than 1% of the primary PCR into the secondary but because of the high concentration of primer used in the primary PCR, a big dilution factor is can be used to ensure these primers do not interfere in the amplification and worsen the amplification bias between sequences. Another alternative is to add a purification or enzymatic step to eliminate the primers from the primary PCR to allow a smaller dilution of it. In this example, the primary PCR was 10 cycles and the second 25 cycles.

Testing High Fidelity Enzymes

Enzymes with higher fidelity can be used to minimize errors. The assay has been optimized using Taq polymerase. In order to validate the use of Accuprime as well as Taq high fidelity a cDNA with the pool of primers was amplified using Taq polymerase, Accuprime, or Taq high fidelity. Each of the amplified material was then used as a template for 34 real time PCR for with each of the 34 V primers and the 1 C primer. The relative amount of the templates was quantitated. A high correlation ($r^2 > 0.95$) between the concentration of each template in the Accuprime, Taq high fidelity and Taq was found, validating the use of these high fidelity enzymes.

Validation of Amplification Conditions

Figure 5:
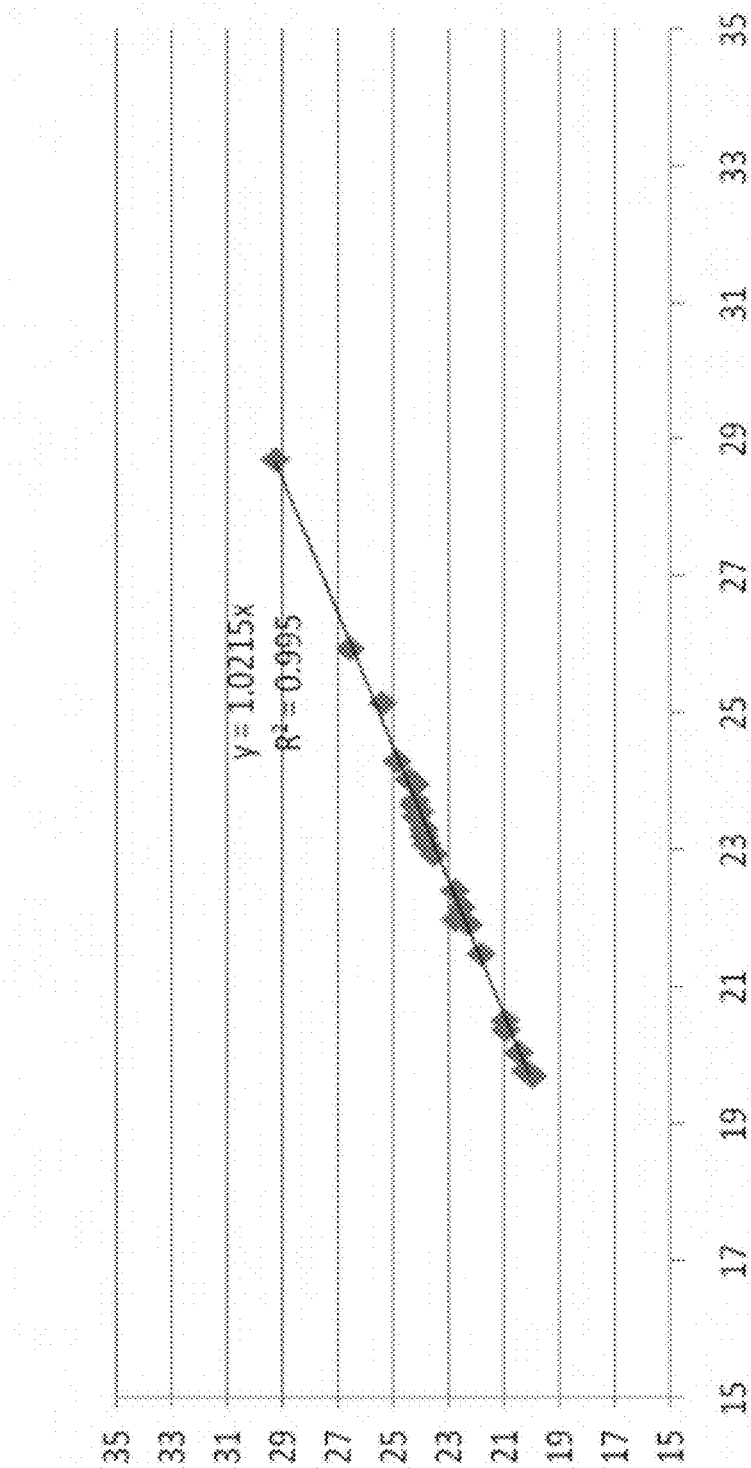
FIG. 5 illustrates the reproducibility of multiplexed amplifications.

The optimization was done using a pool of primers on the standard template not with the cDNA background. The goal was to obtain validation for these results in cDNA mixture. In order to show reproducibility, pool of oligos to amplify cDNA in duplicates were used. Each of the 34 products were quantitated in each of the two amplifications. As shown in FIG. 5, the reproducibility was excellent.

For FIG. 5, two primary PCR reactions were performed using the pooled TCRβ primers and the C primer and one cDNA sample as a template. The relative abundance in each of the amplified material of template that is amplifiable with each of the 34 V primers (and the one C primer) was assessed using real time PCR. Using each of the two amplified products as a template, thirty four different real time PCR reactions were performed using the C primer and one of the V primers in each reaction. The relative abundance determined by real time PCR was highly reproducible using all the V primers between for the two samples, indicating that the multiplexed amplification is highly reproducible. The cycle number (Ct value) for each of the real time PCR amplifications using the one multiplexed amplification product as a template is shown on the X axis and using the second multiplexed amplification product as a template is depicted on the Y axis.

In order to assess the amplification bias a similar technique can be employed. The pool of oligos can be used to amplify using cDNA as a template. Then the amount of template amplified by each of the 34 different primers (along with C segment primer) a can be quantitated using real time PCR and that amount can be compared with the amount amplified using the same primer from the cDNA. However, since there is cross talk even if the relative abundance among the internal sequences in the amplified product and the cDNA were the same, big differences using this readout may be detected. To alleviate this issue 12 oligos were designed that can when used with C segment primer amplify sequences internal to the V segment primers. If optimization was done appropriately, then the concentration of these internal sequences should change little between the cDNA and the amplified products. This is shown is FIG. 6.

Figure 6:
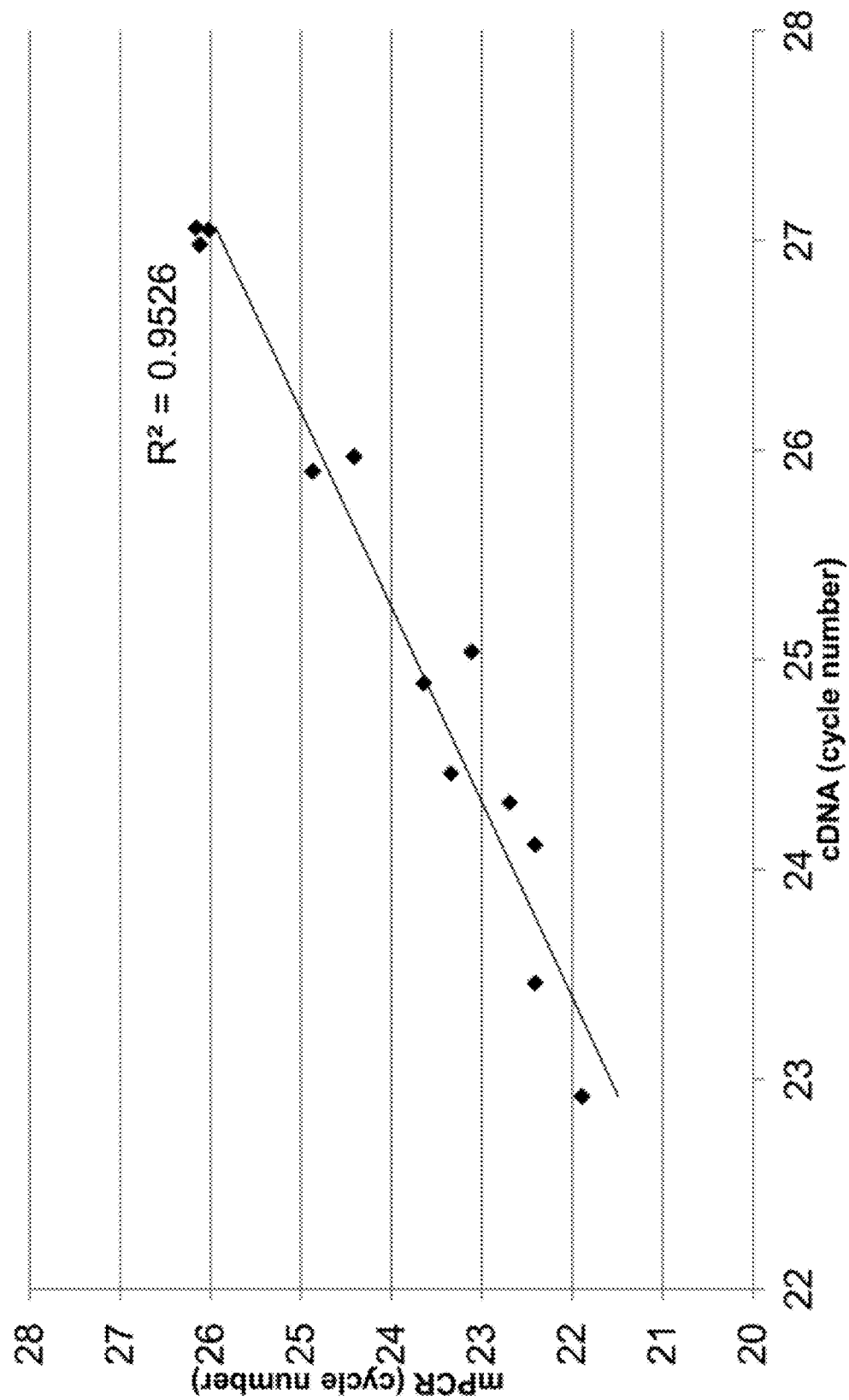
FIG. 6 illustrates that multiplexed amplifications have minimal amplification bias.

For FIG. 6, a cDNA sample was used as a template for a multiplexed amplification using the pooled TCRβ primers and the C primer. The C primer and primers were used that are downstream (to be named internal primers) of the V primers used for the initial amplification and the material from the multiplex amplification material as a template to assess the relative abundance of the different sequences. Similarly real time PCR was used to assess the relative abundance of these same sequences in the cDNA. If the multiplexed amplification had great bias, the relative abundance in the amplified material can be very different from that in the cDNA. As can be seen in FIG. 6, high correlation was seen demonstrating minimal amplification bias in the multiplexed amplification. The cycle number (Ct value) for each of the real time PCR amplification using internal primers, and cDNA and the multiplexed amplification product as template is shown on X and Y axis, respectively.

Sequencing TCRβ

Six multiplexed amplifications with the pooled oligos and one cDNA sample as a template were used. Three of each of the amplifications were done with Accuprime and another 3 with high fidelity Taq. Two amplifications with each enzyme used cDNA that correspond to 500 ng initial RNA, and one amplification with each enzyme used 10 times less cDNA. For each of the six reactions a primary and secondary PCR was performed and the amplified material was sequenced using the Illumina platform and the scheme described above. 100 bp sequence from each side was obtained. The primary analysis of the data was done using the same concepts described below.

Figure 8A:
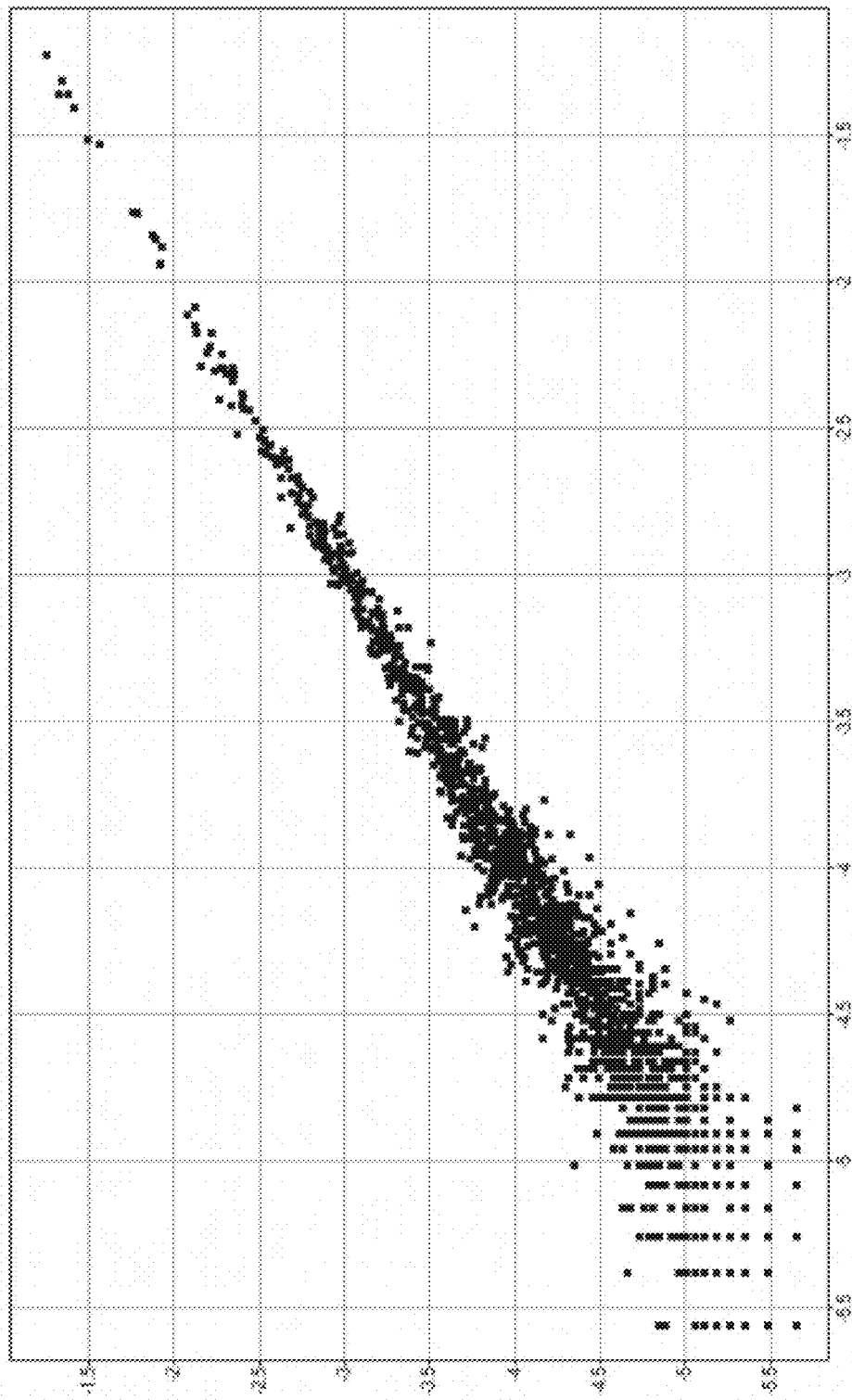
FIG. 8A shows the $\log_{10}$ of the frequency of each clonotype in the two duplicate samples using Accuprime and cDNA corresponding to 500 ng of RNA as input template.
Figure 8B:
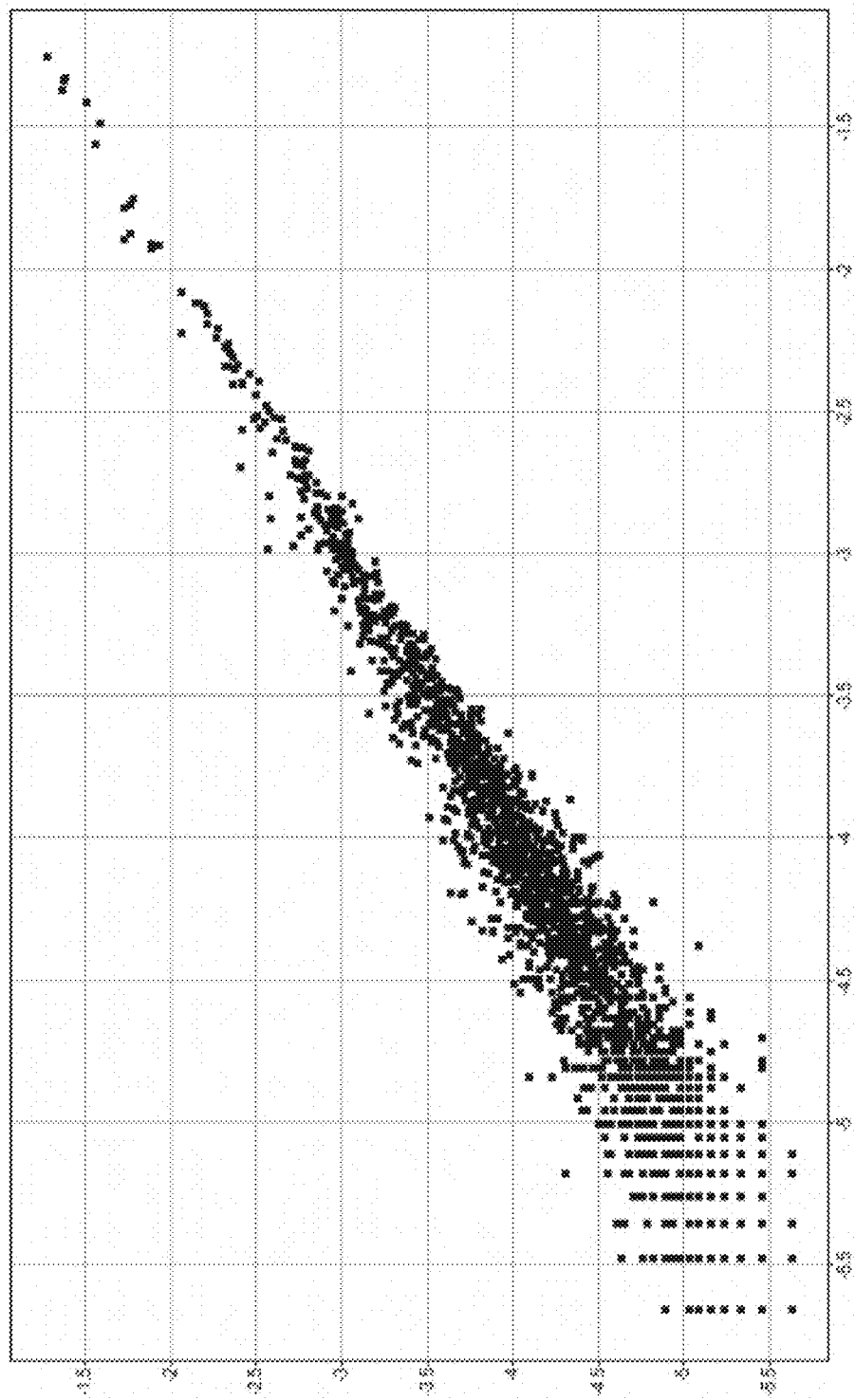
FIG. 8B depicts the $\log_{10}$ of the frequency of each clonotype using cDNA corresponding to 500 ng of RNA as input template and Accuprime (X axis) or High fidelity Taq (Y axis).
Figure 8C:
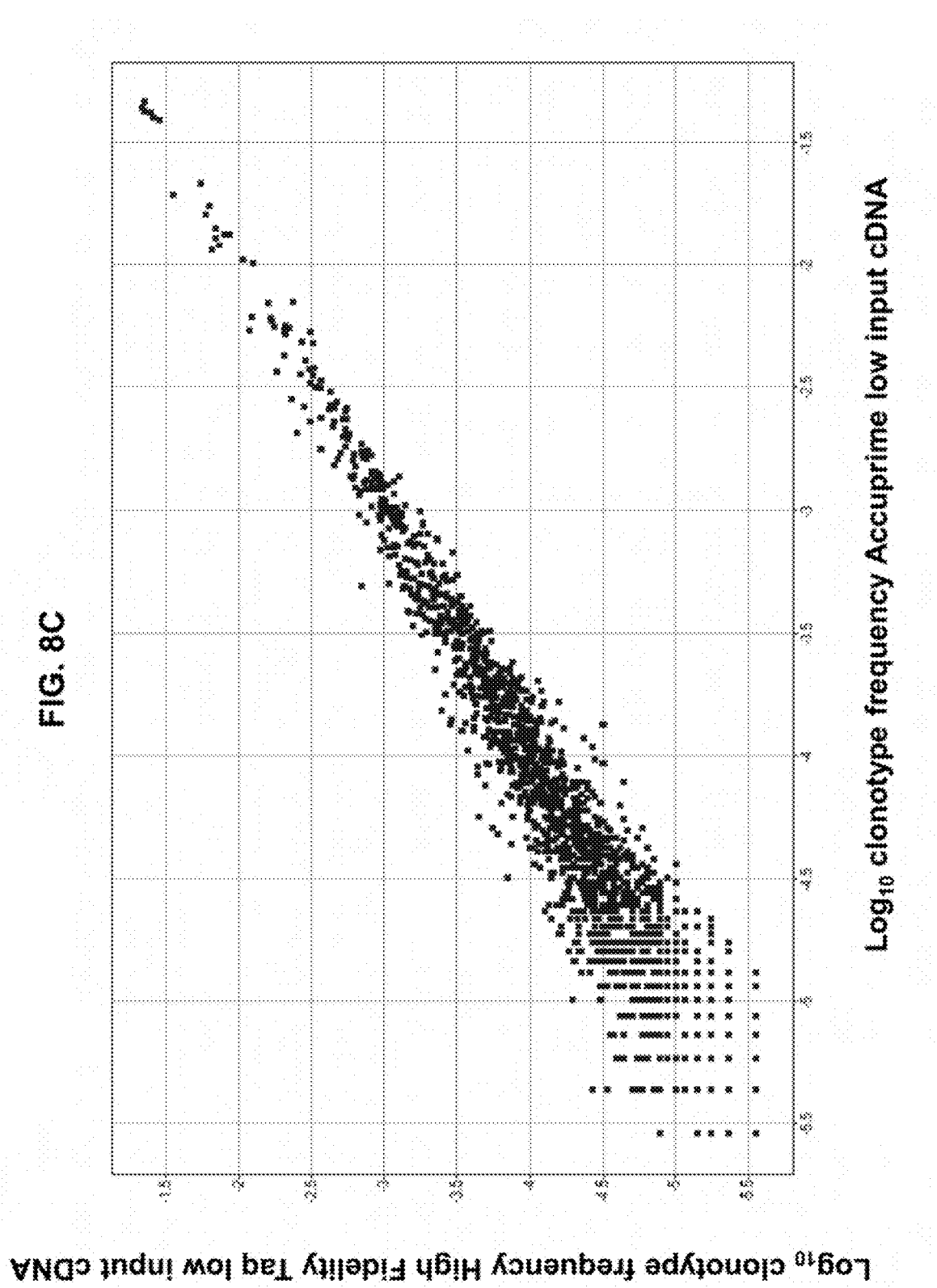
FIG. 8C shows the $\log_{10}$ of the frequency of each clonotype using cDNA corresponding to 50 ng of RNA as input template and Accuprime (X axis) or High fidelity Taq (Y axis).

To assess reproducibility of the assay it was determined whether clonotype levels are consistent in the duplicate experiments. As shown in FIGS. 8A-C, high correlation is obtained when the same enzyme and starting input cDNA amount was used (each of the 2 comparisons had $r^2$=0.944). When different enzymes were used the correlation gets worse (median correlation for the 4 possible combinations $r^2$=0.931), and it is only modestly reduced ($r^2$=0.924) when the 2 enzymes were used to amplify smaller input cDNA (corresponding to only 50 ng RNA).

For FIG. 8, identical sequences in each sample were identified. Then to deal with sequencing errors some clonotypes were coalesced to form larger clonotypes using the general approaches described in the section of primary analysis of sequence. The counts of clonotypes were then computed in each sample. A fraction of the clonotypes (not shown in the figure) were present in one sample but not another, likely due to the algorithm coalescing them with another clonotype in one sample but not the other. The frequency of clonotypes in a sample is then computed as its number of counts divided by the total number of reads obtained for that sample. For example if 1,000 counts are observed for a clonotype in a sample with 1,000,000 reads, its frequency is computed as 0.1%. FIG. 8A shows the $\log_{10}$ of the frequency of each clonotype in the two duplicate samples using Accuprime and cDNA corresponding to 500 ng of RNA as input template. The correlation ($r^2$) between these duplicates is 0.944. FIG. 8B depicts the $\log_{10}$ of the frequency of each clonotype using cDNA corresponding to 500 ng of RNA as input template and Accuprime (X axis) or High fidelity Taq (Y axis). There are 4 comparisons with this combination with a median correlation $r^2$=0.931. The one shown in the figure has $r^2$=0.929. FIG. 8C shows the $\log_{10}$ of the frequency of each clonotype using cDNA corresponding to 50 ng of RNA as input template and Accuprime (X axis) or High fidelity Taq (Y axis). The observed correlation $r^2$=0.924.

These results validate the reproducibility of the assay, and conform to the expectation that reproducibility gets worse when different enzymes are compared. Further reduction is seen when lower amount of input cDNA is used reflecting that lower representation in the input material leads to poorer precision in reflecting the relative abundance of the different clonotypes in the blood. Additionally it is possible some of the reduction in the correlation is due to the additional amplification (10 fold) needed for the lower input, but this is likely to be the minor effect given the evidence for the high reproducibility of the amplification.

Example 4

IgH Repertoire Analysis

Amplification and Sequencing Strategy

One difference between amplification of CDR3 in TCRβ and IgH is that multiple primers for each V sequence will be used in investigation of IgH due to the possibility of somatic mutations in IgH. Three different primers for each V segment will be used. The primers are in regions avoiding the CDRs, which have the highest somatic mutations. Three different amplification reactions will be performed. In each reaction, each of the V segments will be amplified by one of the three primers and all will use the same C segment primers. The primers in each reaction will be approximately the same distance from the V-D joint. Assuming the last position of the V segment as 0, then the first set of primers (A) have the 3' end at approximately −255, the second (B) have the 3' end at approximately −160, and the third (C) have the 3' end at approximately −30. Given the homology between several V segments, to amplify all the 48V segments and the many known alleles (as defined by the international ImMunoGeneTics information system http://imgt.cines.fr/) 23, 33, and 32 primers in the A, B, and C frames respectively, will be needed. The list of primers are shown in Tables 2, 3, and 4.

TABLE 2

Frame A primers

| | Sequence frame A | SEQ ID NO: |
|---|---|---|
| IGHV1_1 | CCTCAGTGAAGGTCTCCTGCAAGG | 39 |
| IGHV1_2 | CCTCGGTGAAGGTCTCCTGCAAGG | 40 |
| IGHV1_3 | CCTCAGTGAAGGTTTCCTGCAAGG | 41 |
| IGHV1_4 | GGGCTACAGTGAAAATCTCCTGCAAGG | 42 |
| IGHV2_1 | AAACCCACACAGACCCTCACGCTGAC | 43 |
| IGHV2_2 | AAACCCACAGAGACCCTCACGCTGAC | 44 |
| IGHV2_3 | AAACCCACACAGACCCTCACACTGAC | 45 |
| IGHV3_1 | CTGGGGGGTCCCTGAGACTCTCCTG | 46 |
| IGHV3_2 | CTGGGGGGTCCCTTAGACTCTCCTG | 47 |
| IGHV3_3 | CAGGGCGGTCCCTGAGACTCTCCTG | 48 |

TABLE 2-continued

Frame A primers

| | Sequence frame A | SEQ ID NO: |
|---|---|---|
| IGHV3_4 | CAGGGCCGTCCCTGAGACTCTCCTG | 49 |
| IGHV3_5 | CTGGGGGGTCCCTGAAACTCTCCTG | 50 |
| IGHV3_6 | CTGGCAGGTCCCTGAGACTCTCCTG | 51 |
| IGHV3_7 | CTGGAGGGTCCCTGAGACTCTCCTG | 52 |
| IGHV3_8 | CTGGGAGGTCCCTGAGACTCTCCTG | 53 |
| IGHV3_9 | TGGGGGGGCCCTGAGACTCTCCT | 54 |
| IGHV4_1 | CTTCGGAGACCCTGTCCCTCACCTG | 55 |
| IGHV4_2 | CTTCGGACACCCTGTCCCTCACCTG | 56 |
| IGHV4_3 | CTTCACAGACCCTGTCCCTCACCTG | 57 |
| IGHV4_4 | CTTCGGAGACCCCGTCCCTCACCTG | 58 |
| IGHV4_5 | CGGGGACCCTGTCCCTCACCTG | 59 |
| IGHV5_1 | GATCTCCTGTAAGGGTTCTGGATACAGCT | 60 |
| IGHV6 | TCGCAGACCCTCTCACTCACCTGTG | 61 |

TABLE 3

Primers for frame B

| | Sequence frame B | SEQ ID NO: |
|---|---|---|
| IGHV6 | TGGATCAGGCAGTCCCCATCGAGAG | 62 |
| IGHV5_1 | GCTGGGTGCGCCAGATGCCC | 63 |
| IGHV2_1 | TGGATCCGTCAGCCCCCAGG | 64 |
| IGHV2_2 | TGGATCCGTCAGCCCCCGGG | 65 |
| IGHV1_1 | GTGCGACAGGCCCCTGGACAA | 66 |
| IGHV1_2 | GGGTGCGACAGGCCACTGGACAA | 67 |
| IGHV1_3 | GTGCGCCAGGCCCCCGGACAA | 68 |
| IGHV1_4 | GGGTGCGACAGGCTCGTGGACAA | 69 |
| IGHV1_5 | GGGTGCAACAGGCCCCTGGAAAA | 70 |
| IGHV1_6 | GGGTGCGACAGGCTCCTGAAAA | 71 |
| IGHV1_7 | GTGCGACAGGCCCCCGGACAA | 72 |
| IGHV1_8 | GTGCGACAGGCCCCCAGACAA | 73 |
| IGHV4_1 | TCCGCCAGCCCCCAGGGAAGG | 74 |
| IGHV4_2 | TCCGGCAGCCCCCAGGGAAGG | 75 |
| IGHV4_3 | TCCGGCAGCCACCAGGGAAGG | 76 |
| IGHV4_4 | TCCGCCAGCACCCAGGGAAGG | 77 |
| IGHV4_5 | TCCGGCAGCCCGCCGGGAA | 78 |
| IGHV4_6 | TCCGGCAGCCGCCGGGAA | 79 |
| IGHV4_7 | TCCGGCAGCCCGCTGGGAAGG | 80 |

TABLE 3-continued

Primers for frame B

| | Sequence frame B | SEQ ID NO: |
|---|---|---|
| IGHV4_8 | TCCGCCAGCCCCTAGGGAAGG | 81 |
| IGHV3_1 | GGTCCGCCAGGCTCCAGGGAA | 82 |
| IGHV3_2 | GTTCCGCCAGGCTCCAGGGAA | 83 |
| IGHV3_3 | GGTCCGCCAGGCTTCCGGGAA | 84 |
| IGHV3_4 | GGTCCGTCAAGCTCCGGGGAA | 85 |
| IGHV3_5 | GATCCGCCAGGCTCCAGGGAA | 86 |
| IGHV3_6 | GGTCCGCCAAGCTCCAGGGAA | 87 |
| IGHV3_7 | GGTCCGCCAGGCTCCAGGCAA | 88 |
| IGHV3_8 | GGTCCGCCAGGCCCCAGGCAA | 89 |
| IGHV3_9 | GGTCCGCCAGGCTCCGGGCAA | 90 |
| IGHV3_10 | GGGTCCGTCAAGCTCCAGGGAAGG | 91 |
| IGHV3_11 | CTGGGTCCGCCAAGCTACAGGAAA | 92 |
| IGHV3_12 | GGTCCGCCAGCCTCCAGGGAA | 93 |
| IGHV3_13 | GGTCCGGCAAGCTCCAGGGAA | 94 |

TABLE 4

Primes for frame C

| | Sequence frame C | SEQ ID NO: |
|---|---|---|
| IGHV7 | CTAAAGGCTGAGGACACTGCCGTGT | 95 |
| IGHV6 | CTCTGTGACTCCCGAGGACACGGCT | 96 |
| IGHV5_1 | AGTGGAGCAGCCTGAAGGCCTC | 97 |
| IGHV2_1 | TGACCAACATGGACCCTGTGGACAC | 98 |
| IGHV1_1 | ACATGGAGCTGAGCAGCCTGAGATC | 99 |
| IGHV1_2 | ACATGGAGCTGAGCAGGCTGAGATC | 100 |
| IGHV1_3 | ACATGGAGCTGAGGAGCCTGAGATC | 101 |
| IGHV1_4 | ACATGGAGCTGAGGAGCCTAAGATCTGA | 102 |
| IGHV4_1 | GAGCTCTGTGACCGCCGCGGAC | 103 |
| IGHV4_2 | GAGCTCTGTGACCGCCGTGGACA | 104 |
| IGHV4_3 | GAGCTCTGTGACCGCTGCAGACACG | 105 |
| IGHV4_4 | GAGCTCTGTGACCGCTGCGGACA | 106 |
| IGHV4_5 | GAGCTCTGTGACTGCCGCAGACACG | 107 |
| IGHV4_6 | GAGCTCTGTGACTGCAGCAGACACG | 108 |
| IGHV4_7 | GAGCTCTGTGACTGCCGCGGACA | 109 |
| IGHV4_8 | GAGCTCTGTGACCGCGGACGCG | 110 |
| IGHV4_9 | GGCTCTGTGACCGCCGCGGAC | 111 |
| IGHV4_10 | GAGCTCTGTGACCGCCGCAGACA | 112 |
| IGHV4_11 | GAGCTCTGTGACCGCTGACACGG | 113 |

TABLE 4-continued

Primes for frame C

| Sequence frame C | | SEQ ID NO: |
|---|---|---|
| IGHV3_1 | CAAATGAACAGCCTGAGAGCCGAGGACA | 114 |
| IGHV3_2 | CAAATGAACAGCCTGAAAACCGAGGACA | 115 |
| IGHV3_3 | CAAATGAACAGTCTGAAAACCGAGGACA | 116 |
| IGHV3_4 | CAAATGATCAGCCTGAAAACCGAGGACA | 117 |
| IGHV3_5 | CAAATGAACAGTCTGAGAACTGAGGACACC | 118 |
| IGHV3_6 | CAAATGAACAGTCTGAGAGCCGAGGACA | 119 |
| IGHV3_7 | CAAATGAACAGCCTGAGAGCTGAGGACA | 120 |
| IGHV3_8 | CAAATGAGCAGCCTGAGAGCTGAGGACA | 121 |
| IGHV3_9 | CAAATGAACAGCCTGAGAGACGAGGACA | 122 |
| IGHV3_10 | CAAATGGGCAGCCTGAGAGCTGAGGACA | 123 |
| IGHV3_11 | CAAATGAACAGCCTGAGAGCCGGGGA | 124 |
| IGHV3_12 | CAAATGAACAGTCTGAGAGCTGAGGACA | 125 |
| IGHV3_13 | CAAATGAGCAGTCTGAGAGCTGAGGACA | 126 |

On the C segment side, two sequences with one base difference between them (GCCAGGGGGAAGACCGATGG (SEQ ID NO: 127), and GCCAGGGGGAAGACGGATGG (SEQ ID NO: 128)) cover the four segments and the multiple known alleles of IgG. A scheme similar to the two stages of PCR for TCRβ genes will be used. On the V side, the same 5' 14 bp overhang on each of the V primers will be used. In the secondary PCR, the same Read2-tagX-P7 primer on the V side is employed. On the C side a strategy similar to that used with TCRβ amplification will be used to avoid variants among the different IgG segments and their known alleles. The primer sequence (AATGATACGGCGACCAC-CGAGATCTGGG AAG ACGAT GG GCC CTT GGT GGA (SEQ ID NO: 129)) comprises the sequence of the C segment from positions 3-19 and 21-28 and it skips position 20 that has a different base in at least one of the different IgG alleles and the sequence for P5 that is can be used for formation of the clusters as shown in FIG. 4.

All the primers in the 3 frames were successful in amplifying a single band from cDNA. Similarly the primary and secondary PCR strategy using the three pools of primers in the primary PCR showed a single band as shown in FIG. 7.

Figure 7:
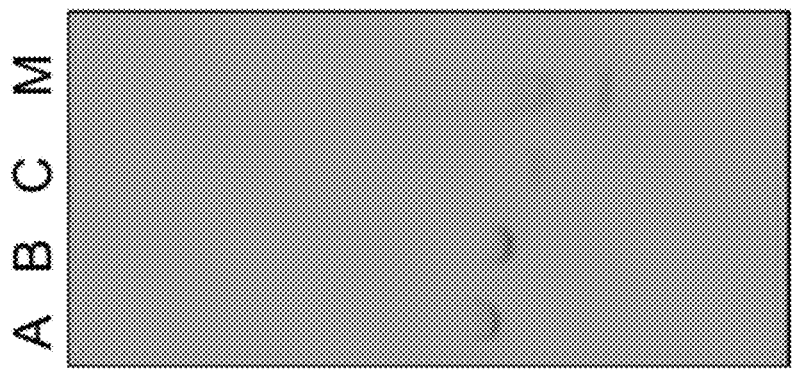
FIG. 7 illustrates agarose gel electrophoresis of multiplexed amplification of IgH sequences.

For FIG. 7, multiplexed PCR using 3 pools of primers corresponding to the 3 frames was done using cDNA as a template. After the primary and secondary PCR the products were run on an agarose gel. A denotes the PCR product from the pool of oligos of frame A. Similarly B and C denote the products of pools B and C. M is a marker lane. Single bands with the appropriate sizes were obtained using all 3 pools.

Ultimately, the 3 different reactions from a single sample will then be mixed at equimolar ratio and subjected to sequencing. Sequencing will be done from both directions using the two Illumina primers. 100 bp will be sequenced from each side. The maximal germline sequences encompassing the D+J segments are ~30 bp longer for BCR than TCR. Therefore if the net result of nucleotide removal and addition at the joints (N and P nucleotides) generate a similar distribution for IgH and TCRβ, it is expected that on average 90 bp and maximally 120 bp of sequence after the C segment will be sufficient to reach the 3' of the V segment. Therefore, in most cases, the sequence from the C primer will be sufficient to reach the V segment. Sequencing from one of the Illumina adapters should identify the V segment used as well as identify somatic hypermutations in the V segments. Different pieces of the V segments will be sequenced depending on which of the three amplification reactions the sequence originated from. The full sequence of the BCR can be aligned from different reads that originated from different amplification reactions. The sequencing reaction from the one end showing the full CDR3 sequence will greatly facilitate the accurate alignment of different reads.

Example 5

Primary Analysis of Human Sequence Data

For each patient sample, approximately 1 million high quality reads of 100 bp paired-end reads each will be obtained. It is assumed these 1 million reads are independent, originating from 1 million or more RNA molecules obtained from 1 million cells or more. Reads with low quality will be eliminated.

An error rate of ~1% will be anticipated. Error can arise either from the reverse transcriptase, amplification during PCR or during sequencing. Error proofing enzymes for the PCR steps will be used; hence sequencing errors (~1%) will be the main source of error as the PCR error rate is less than 0.1%. The relevance of PCR and reverse transcriptase error will be greatly magnified in situations where there is a bottle neck. A bottleneck can occur, for example, if over 100,000 RNA molecules is started with or one of the different molecular manipulation steps is inefficient so as to make the effective population of molecules 100,000. In these situations the same error that occurred due to PCR or reverse transcriptase can appear in many clusters.

Data will be obtained for TCRβ and IgH. Given the somatic hypermutation in IgH and the difference in the amplification strategy, the primary analysis of TCRβ and IgH will be somewhat different.

TCRβ

On one end, the C' segment primer for sequencing will be used. The length of the V segment that will be sequenced will depend on the length of N+P nucleotides added. Given the average number of added nucleotides, about 40 nucleotides of the V segment will be sequenced. On the other end the Illumina sequencing primer P7 will be used. The sequence of 20 bp of V primer sequence followed by 80 bp of V segment sequence will be obtained.

Reads will be aligned to the germline V segments (including the different known alleles) to assign a V segment to each read. Reads that don't substantially match any V segments will be discarded from further analysis reads. A substantial match will be defined as one where there is no more than 5 errors. Given a random error rate of 1% it is expected that this scheme would discard <1% of reads due to error. The rest of the sequences will be assigned to the V segment that has the highest match. Primers amplifying V segments of the same family will often be highly related with one or a few bases difference between them. These primers can "cross talk", amplifying other family members. Therefore the beginning of the sequencing read (the primer) can be for a V segment that is different from the V segment the rest of the read belongs to. Such cases will be allowed and do not count as errors.

The sequences from the end of the V segment to the beginning of the C segment is evaluated. This sequence will be called the DJ region. This sequence is on average 60 bases with a very small fraction as large as 90 bases. It is likely to be able to assign the J segment in most cases as the end close to the C segment is likely to be preserved. On the other hand, the D segment may be difficult to assign given its small size (15-16 bp) and the trimming and addition that occurs on both of its ends. Of note is that when a J segment is assigned, it is possible to predict the D and C segment. After assigning the segment, the sequence of the DJ region will be defined. Error complicates this analysis more than it does for the C and V segment alignment for two reasons. First error in the DJ alignment can occur in either of the two reads being aligned effectively doubling the error rate of alignment of a single read to the database sequence.

Additionally, one base difference in the C or V alignment can be readily attributed to error (except for the rare case of a previously undescribed V germline allele), and sequences having one base difference to a V segment can be assigned to have the sequence of the V segment. On the other hand it will not be clear whether a one base difference between two DJ region reads is due to an error or a genuine sequence difference between two clonotypes. There are two possibilities: the reads belong to the same clonotype but have errors, or there are two or more distinct clonotypes. Clonotypes will be designated as distinct when the chance of their emergence by sequencing error is low either because of their frequent observations or because they diverge in too many bases.

It is expected that PCR error will be concentrated in some bases that were mutated in the early cycles of PCR. Sequencing error is expected to be distributed in many bases even though it will be totally random as the error is likely to have some systematic biases. It will be assumed that some bases will have sequencing error at a higher rate, say 5% (5 fold the average). Given these assumptions, sequencing error becomes the dominant type of error. Distinguish PCR errors from the occurrence of highly related clonotypes will play a role in analysis. Given the biological significance to determining that there are two or more highly related clonotypes, a conservative approach to making such calls will be taken. The detection of enough of the minor clonotypes so as to be sure with high confidence (say 99.9%) that there are more than one clonotype will be considered. For examples of clonotypes that are present at 100 copies/1,000,000, the minor variant will be detected 14 or more times for it to be designated as an independent clonotype. Similarly, for clonotypes present at 1,000 copies/1,000,000 the minor variant can be detected 74 or more times to be designated as an independent clonotype. This algorithm can be enhanced by using the base quality score that will be obtained with each sequenced base. If the relationship between quality score and error rate is validated above, then instead of employing the conservative 5% error rate for all bases, the quality score can be used to decide the number of reads that need to be present to call an independent clonotype. The median quality score of the specific base in all the reads can be used, or more rigorously, the likelihood of being an error can be computed given the quality score of the specific base in each read, and then the probabilities can be combined (assuming independence) to estimate the likely number of sequencing error for that base. As a result, there will be different thresholds of rejecting the sequencing error hypothesis for different bases with different quality scores. For example for a clonotype present at 1,000 copies/1,000,000 the minor variant is designated independent when it is detected 22 and 74 times if the probability of error were 0.01 and 0.05, respectively.

After designating clonotypes that occur too frequently to be due to error as distinct or independent, criteria will be considered that allow designation of clonotypes as independent due to their differences in too many bases. It is expected that less than 0.1% of time, two reads will have more than 4 errors in 60 bp between them. Therefore this will be used as a cut off to consider two clones as independent or distinct. The algorithm that will be employed will be as follows. The clonotype with the largest number of counts (clonotype 1) will be noted, and it will be determined whether there are any other clonotypes that have the same V segment and have 4 or less base differences from it in the DJ region. If more than one such clonotype is identified, the largest of these clonotypes will be assessed first. The rule described above will be applied to decide whether to designate the clonotype as an independent clonotype or the same as the major clonotype. If it is not designated as an independent clonotype it will then be counted as if it has the sequence of clonotype 1. At the end of this exercise the sequence and counts for all clonotypes will be obtained. This approach ensures that clonotypes will not be designated as independent when they are not. However, some truly independent clonotypes may be misclassified (not frequent with low number of differences from the major clonotype) as being the same. This type of error will be much less damaging than considering two clonotypes as independent when they are not.

IgH

For sequencing of the C segment end, the Illumina primer will be used. The first bases to be sequenced will be the C segment primer followed by 0-2 bases of C segment and then the DJ region. The primer sequence will identify which isotype the specific read belongs to. All or most of the DJ sequence can be obtained through the read from the C segment side. It is expected that the DJ region will be on average 80 bp. Therefore, 100 bp read will encompass the C segment primer and the average DJ region. Some DJ regions may be as large as 120 bp, and their full reading can include sequencing data from the V region (not counting those cases where 2 D segments are found in the same IgH).

The sequence of the DJ region obtained from the C segment will initially be considered. The number of each unique sequence will be counted. As discussed for TCRβ, some of the related sequences originate probably from the same clonotype but have some sequencing and PCR error. To designate two clonotypes as distinct, it will be determined whether the difference is very unlikely to have arisen through PCR error. The same scheme as above of demanding a minimum number of independent observations of the minor clonotypes or a minimum number of differences between the two clonotypes will be used. The same rules described for TCRβ to ensure that <0.1% of clonotypes are misclassified as distinct will be employed.

Sequencing from the V region will be done using an Illumina primer. There will be 3 different primers for each V segment. The primers will be placed at approximately −200, approximately −100, and approximately −30. The first sequenced bases will be the V primer sequence followed by more of V segment bases. The specific read to one of the three priming frames of a specific V segment will be assigned. The assignment will be first done through investigating the primer sequence since the primers have a known sequence that can't change. Primers of the same family can sometimes have some "cross talk" amplifying highly related sequence in the same family. The primers will be used to assign the family. The specific V segment among the segments in the family will be determined by identifying the V sequence of the family that is most similar to that of the sequencing read. V segments in IgH can have somatic mutations in the course of the antibody affinity maturation process and therefore a higher proportion of differences from the germline sequences will be allowed than for TCRβ. Antibodies with more than 25 mutations (~10%) in the VDJ region have been observed. A read will be assigned to the framework of the V segment with the closest sequence as long as it has >85% homology to it. Related clonotypes will be assessed for being independent using the same scheme as described above. Specifically for clonotypes to be considered distinct and due to somatic mutations not error, they need to be either sufficiently frequent or have ample variation between them to ensure that less than 0.1% of clonotypes misclassified as distinct when they are not.

For reads that are determined to have the third framework (closest to the VD junction), the overlap sequence between the paired end reads will be determined. Bases not aligned with the V segment will be aligned to the complement of the first read to determine the overlap. The primers for the third framework will be ~30 bp away from the junction. Therefore, if the V is intact approximately 50 bp of sequence can be used to reach the VD junction (20 bp primer+30 bp), and 100 bp reads will allow 50 bp to be read after the junction. This is the minimum expected number of bases that would be read after the VD junction as the deletion of some bases in V will allow for a longer read after the junction. Even for the longest DJ region, it is expected that there will be 10 bp overlap between the sequences from the paired reads. The longest DJ region is expected to be 120 bp, and 80 bp of it are expected to be read from the C segment and 50 bp read from the other direction of the V region leading 10 bp overlap between the paired reads.

Clonotypes that read the same sequence from the C primer but has different frameworks of the same V segment become candidates for consolidation in the same clonotypes. If there is overlap between the sequences obtained from the different frameworks of the V segment then the determination of whether the clonotypes are independent or not is done with the same rules as described above.

As a result of the above analysis, the number of reads for each clonotype can be counted. Clonotypes that are from the same family differing from each other only by somatic mutations are identified. These somatic mutations can be restricted to sequences in the V segment read from only 1 framework, more than 1 framework, or in the DJ region.

Example 6

TCR and IgH Repertoire Analysis in SLE Patient Samples

It will first be tested whether there are clonotypes that correlate with disease activity in patients. Second, a set of sequence characteristics and/or cell surface markers that distinguish clonotypes that correlate with disease from those that do not will be defined. Third, the degree to which clonotype analysis provides clinically useful information will be measured, such as the correlation with short term (e.g., 3 month) outcome.

1. Presence of Clonotypes Correlating with Disease

There will be two main tasks: identifying correlating clonotypes and measuring disease activity from their level. These tasks can be done in a clinical setting in two steps for each patient:

1) A Calibration test can be done to determine the identity of the correlating clonotypes for the specific patient. This can be done by sequencing IgH and TCRβ RNA (or linked TCRα- TCRβ sequence from a single cell) for each patient at a time of a peak of an episode, at which time the correlating clonotype level can reach their highest levels.

2) A Monitoring test can be done to determine the level of the correlating clonotypes at a time point subsequent to the calibration test. This can be done by sequencing IgH and TCRβ RNA and determining the level of the specific correlating clonotypes that had been identified in the calibration sample of the same patient. The level of the correlating clonotypes is used to compute the disease activity at these points.

Amplification, sequencing, and primary analysis development as described above will be used to assess patient samples. Specifically, a set of systemic lupus erythematosus (SLE) patients will be assessed that have a one year follow up period and serial blood samples during this period. These patients were seen By Dr. Michele Petri at Johns Hopkins Medical School every three months for one year, and clinical measures of disease activity including Systemic Lupus Erythematosus Disease Activity Index (SLEDAI), Physician Global Assessment (PGA), as well as multiple lab tests including C3 (Complement 3) and anti-ds DNA levels are available for all visits of all patients. Drugs being administered to the patients, include prednisone, plaquenil, NSAID, NSAIDType, acetylsalicylic acid (ASA) dose, plavix, diuretic, ACE-Inhibitors or angiotensin receptor blockers (ARBs), Ca channel blocker, Triam and, solumedrol, Patients who had at least at one time during the follow up a significant change in disease activity as defined by a 3 points change on the SLEDAI or a 1 point change in PGA will be studied. Overall there are 181 patients (with a total of 815 blood samples) who fit these criteria. RNA from all these blood samples will be subjected to multiplex PCR using primers described above to amplify the sequences that encompass CDR3 in IgH and TCRβ. All the amplified materials will be sequenced (to a million reads) and the abundance of different clonotypes will be determined Using the clinical data, sequencing, characteristics that distinguish clonotypes whose level correlate with disease activity from those that do not will be identified. Second, an algorithm to determine disease activity using the blood IgH and TCRβ profile will be developed.

2. Identification of Characteristics of Correlating Clonotypes

It is anticipated that clonotypes that are relevant to the disease will be increased at the time of high disease activity. However, not all enriched clonotypes at a point of high disease activity necessarily correlate with disease. For example, in a particular patient there might be 10 enriched clonotypes at the point of high disease activity, but only 5 correlate with the disease. In order to identify these relevant clonotypes, a subset of clonotypes that are clearly correlating with disease and another set that clearly do not correlate with disease will be studied. Characteristics that distinguish those two classes of clonotypes will be investigated.

All patients will have at least one significant change in disease activity during the one year follow up in this experimental design. The IgH and TCR clonotypes obtained at the peak of disease activity in each patient will be analyzed. Sets of correlating and not correlating clonotypes among those with the highest level clonotypes will be selected. Hence the first step is to define clonotypes that are at a high level. The specific criteria to choose the clonotypes that will enter the analysis will include a combination of frequency rank of the clonotype and the level of clonotype (number of clonotype reads per million), as well as evidence the clonotype does not belong to the distribution of low frequency clonotypes.

This set of clonotypes from each patient sample, termed High Prevalent Clonotypes (HPC) will be further analyzed.

The correlation of the level of each of these clonotypes with clinical measures will be evaluated. The correlation of SLE-DAI score with the clonotype level will be computed. For each patient there will be 4-5 study points that can be used to assess the correlation of SLEDAI with the level of each HPC. The distribution of these obtained correlations will be investigated. It is anticipated that most of the HPCs will have low correlation with SLEDAI. It will be investigated whether at the high correlation end there is an excess to what is expected to be generated randomly. For example with 4 and 5 data points it is expected that ~2.5% and ~0.6% of the correlation levels ($r^2$) will be >0.9 bp chance. A higher proportions of HPCs with $r^2$>0.9 indicates the presence of a clonotypes that correlate with disease. In addition to comparing the number of correlating clonotypes with random expectation, a permutation analysis will be performed where the correlation of SLEDAI scores from one patient and the level of individual HPCs from another will be calculated. The distribution of correlations generated from this permutation can be used as the "background" correlation. (To ensure its validity, it will be confirmed that there is little correlation between SLEDAI between different patients). Excess correlation at the high correlation end, e.g., $r^2$>0.9 will indicate the presence of clonotypes that correlate with disease. The highest correlating clonotypes as the set of correlating clonotypes will be picked. Because the number of HPCs that has a by chance correlation higher than a set threshold is known (from calculation using random assumption or through the permutation analysis described above), the threshold to define the correlating clonotype can be set in such a way as to have 10% false discovery rate, i.e. 10% of the correlating clonotypes set will be correlating by chance. A set of HPCs that have very little correlation with SLEDAI score will be picked. Those will serve as the set of non-correlating clonotypes. These 2 sets of clonotypes can be further analyzed to identify characteristics that may distinguish them. These characteristics can then be looked for in new samples to identify the clonotypes likely to be correlating with disease activity in these samples. The blood levels of these clonotypes can then be followed to determine disease activity.

One complication arises from the premise that clonotype level may change before disease activity does. Hence it is possible that by attempting to study only HPCs that highly correlate with SLEDAI, clinically useful clonotypes that change earlier than SLEDAI may be eliminated. Another set of clonotypes will be picked that correlate with a Modified SLEDAI (MSLEDAI) score. MSLEDAI is the same as SLE-DAI in all the study points except those just before a significant change. For those data points the MSLEDAI score will be the average between the SLEDAI score at that point and the next study point. Clonotypes that change before SLEDAI are likely to show better correlation to MSLEDAI than SLE-DAI. It will be informative to compute the excess number of HPCs that have high correlation with MSLEDAI than expected by random or permutation generated expectations.

Characteristics that distinguish correlating clonotypes from those that do not correlate will then be identified. The analysis will be done in the exact manner for those clonotypes that correlate with SLEDAI or MSLEDAI. In either case the goal would be for these set of characteristics to correctly recapitulate this classification enabling the identification of correlating clonotypes in the next set of samples. It is expected that each patient will have a unique set of correlating clonotypes, but the training study will be designed to generate the rules that predict the correlating clonotypes from a calibration sample (at high disease activity). Two general types of parameters can be tested: those that are obtained from the sequencing data itself, and those that can use extra experimentation. Extra experimentation can include the assessment of different cells with different cell surface or other markers. Here are a few types of parameters that will be investigated:

1) Sequence motif: The motif can be a specific V or J region, a combination VJ, or short sequences in DJ region that is associated with a clonotype being correlating.

2) Size of the clonotype.

3) Level: Absolute level (number of reads per million) or rank level.

4) Similarity to other clonotypes: The presence of other highly related clonotypes, like those with silent changes (nucleotide differences that code for same amino acids) or those with conservative amino acid changes.

5) For the BCRs the level of somatic mutations in the clonotype and/or the number of distinct clonotypes that differ by somatic mutations from some germline clonotypes.

Each of these parameters will be individually studied for association with correlating clonotypes. A threshold of 0.05 (uncorrected for multiple testing) will be set to eliminate factors that are not likely to contribute to prediction of correlating clonotypes. Given the multiple parameters, many tests will be performed to generate multiple positive results by chance. However the main goal of this step is to filter the parameters to a smaller set. The set of positive parameters will then be used to create an algorithm to classify the two sets of clonotypes. A machine learning algorithm will be employed that uses the different parameters to classify the two sets of clonotypes. In order to minimize the risk of overfitting, the cross validation technique will be used. Using this algorithm each clonotype will get a score that corresponds to the likelihood it is a correlating clonotype. A threshold will then be placed to classify clonotypes above it as correlating and those below it as non-correlating. The accuracy of the classification can be estimated by the cross validation technique; for example, the clonotypes are put in equal groups and the algorithm using all clonotypes except one group. Clonotypes in the last group (test group) are then classified using the algorithm that was obtained using the rest of the clonotypes. This is iterated as many times as the number of groups, and in each iteration all the groups except one are used for training and one group is classified. The accuracy of the algorithm can be estimated from the average accuracy of the different classifications in the different iterations. It is of note that in all these iterations the exact algorithm would be slightly different. The accuracy of classification is then an estimate as it is not on the final algorithm but rather on a set of related algorithms generated with training data from all clonotypes except one.

Ultimately, two algorithms will be generated trained on two different correlating clonotypes sets: one correlating with SLEDAI and the other correlating with MSLEDAI. Even if the clonotypes in the training set are different the resulting algorithm may or may not be very different, depending on whether these clonotypes indeed come from two distinct populations. The algorithms will be compared. Additionally these algorithms will be used to identify correlating clonotypes that were not initially in the training set. The clonotypes identified in the two algorithms will be compared, and if the initial clonotypes in the two training sets were from the same population, the identified clonotypes are likely to be very similar. Unless the results of the algorithm were quite similar, both algorithms will be carried to identify correlating clonotypes in order to measure lupus disease activity.

Other experimental approaches can add to the power of sequencing in identifying clonotypes that correlate with diseases. Correlating clonotypes may be enriched in cells with some surface or other markers. For example B cells with high levels of CD27 are known in active lupus patients, and hence it might be that correlating clonotypes might be enriched in the CD27 population of cells. If that is borne out to be true, prediction of correlating clonotypes can be improved by doing an enrichment for cells with high levels of CD27. Specifically, a sequencing reaction can be performed on the IgH sequences from all B cells in the blood sample as well as from those B cells with high CD27. Correlating clonotypes are expected to be present at higher frequency in the high CD27 population than in the all blood sample.

3. Using IgH and TCRβ Profiles to Determine Lupus Disease Activity

The section above described clonotype-based analysis to identify features of correlating clonotypes. In addition, for that analysis only a fraction of all the HPCs were used to clearly designate clonotypes as correlating or non-correlating. This section describes analysis that is at the patient level aiming to compute a measure of disease activity, to be called AutoImm (AI) score. The algorithm developed per the above section will be applied to identify correlating clonotypes among all the HPCs. The level of these correlating HPCs will be determined. The level of the correlating clonotypes can be normalized to the total number of TCR clonotypes as well as to HPCs predicted not to correlate with disease. The level of these correlating clonotypes at different time points will be used to compute AI score at these different points.

In patients with more than one correlating clonotypes, the information regarding the level of these different clonotypes will be combined. In addition data from IgH and TCRβ clonotypes will be integrated. Different algorithms for making the combination will be attempted. For example, the average, median, sum, and highest correlating clonotype level will be studied. The clonotype level can be its simple linear read counts, the logarithm of that or some other conversion. It can potentially be the difference between correlating and non-correlating clonotypes. Furthermore methods for weighted average can be utilized. The weighting can be based on the likelihood of a clonotype to be correlating.

In order to evaluate which of the models is optimal, all the models will be assessed to identify the one that generates the highest correlation between the AI score and the SLEDAI score. For this analysis the correlation of SLEDAI and AI scores is done across all the data obtained from all the study points from all patients. In order to estimate and ameliorate the degree of overfitting, the cross validation technique will be used. The level of correlation measured reflects the "cross sectional" relationship between the AI and SLEDAI scores. In addition to SLEDAI, the correlation with other clinical measures like C3 and anti-ds DNA antibody levels as well as urine protein/serum creatinine for patients with kidney manifestation and blood counts for patients with hematological involvement will be studied. The correlation may be due to the classification of patients into high and low disease activity, and is not necessarily a reflection of AI correlating with SLEDAI score within a patient. To demonstrate that, "longitudinal" assessment will be done.

4. Longitudinal Analysis

In the longitudinal analysis, two general questions will be assessed: does AI score at one study point predict disease activity at the same point, and does AI score at one study point predict disease activity at a later point, e.g., the next study point 3 months later.

The relationship between AI and SLEDAI scores at the same study point will be assessed in two ways. First the correlation of the AI and SLEDAI in each patient will be calculated, and then the average and median patient correlation level will be computed. If the correlation seen in cross sectional analysis above is due to classification of high and low disease activity patients and not changing disease activity within individual patients, then the longitudinal correlation in individual patients is likely to be low. A high median patient correlation level suggests that AI does reflect the SLEDAI score at an individual patient level. In addition to the correlation of AI and SLEDAI scores, the correlation of AI with other relevant measures like C3 and anti-ds DNA antibody will be assessed as well as urine protein/serum creatinine for patients with kidney manifestation and blood counts for patients with hematological involvement.

Another way to demonstrate the ability of AI score to measure disease activity changes in individual patients is by determining its accuracy in distinguishing states of high from low disease activity in the same patients. For each of the 181 patients, the two study points when the SLEDAI where at the highest (to be called HDAP for high disease activity point) and lowest levels (to be called LDAP for low disease activity point) will be selected. The distribution of the AI of all the HDAPs with that of the AI of all the LDAPs will be compared, and the p-value that they are different will be computed. In addition, the frequency that the AI at HDAP is higher than LDAP in each patient will be assessed. If AI does not change with disease activity in an individual patient then it is expected that AI at HDAP is higher than that at LDAP only 50% of times. Another analysis will be done where the fraction of times that AI at HDAP is higher than that at LDAP by a meaningful difference (i.e., above the likely AI variation) is determined. To measure the fluctuation of AI, all the study points from all the patients will be used, and the standard deviation (and relative standard deviation) of AI in the different bins of SLEDAI values can be computed. This will generate relative standard deviation across all patients (AI-RSDall) and this value may or may not be dependent on SLEDAI (i.e. the AI-RSDall may be different at different SLEDAI values). The proportion of patients where AI at HDAP is higher than AI at LDAP by a specific number (e.g., 2) of AI-RSDall can be computed. There can be some systematic bias where the computed AI in some patients is consistently higher (or lower) than what is expected from the SLEDA score. Therefore AI-RSDall is a combination of the intrinsic fluctuation of AI within a patient as well as the systematic difference of AI for patients with similar SLEDAI. The intrinsic fluctuation of AI can be computed within a patient by calculating the standard deviation (and relative standard deviation) of AI scores among study points with similar SLEDAI values (<2 points difference) within a patient. The median among all the patients of the relative standard deviation can be computed (AI-RSDpt-med). The proportion of patients where AI at HDAP is higher than AI at LDAP by a specific number (e.g., 2) of AI-RSDpt-med can then be evaluated.

After demonstration that AI does indeed fluctuate with SLEDAI within individual patients it will be evaluated whether AI can predict SLEDAI at the next study point, 3 months later. To assess that correlation level between the AI score at time 0 and the SLEDAI score at time+3 months can be quantitated. The correlation can be computed on a patient level and then the median patient correlation can be obtained. Another way to demonstrate the ability of AI to predict near future disease activity is to evaluate the sensitivity and specificity of AI in predicting disease activity 3 months in the future. Clinically, those patients who are doing well on their current management can be distinguished from those that do not. A patient state at a particular time will be classified into one of two classes: Poor Control (PC) and include patients who in 3 months will have high disease activity (SLEDAI>6 points) and/or a flare (SLEDAI increase by 3 points), and Good Control (GC) and include patients who in 3 months will have low or moderate with disease activity (SLEDAI<6) and/or a significant reduction in disease activity (SLEDAI decrease by 3 points). The classification sensitivity can then be evaluated and specificity obtained using different thresholds of AI. A ROC curve that describes the performance of AI in predicting the state of the patient (PC or GC) can be generated 3 months ahead of time. The performance obtained by this test will be compared with that of standard clinical measures including SLEDAI, anti-ds DNA and C3 levels.

An analysis to evaluate the ability of AI to predict changes in SLEDAI scores 3 months later will also conducted. Using data from all study points of all patients, the relationship between AI and SLEDAI scores can be plotted to identify the "cross sectional" correlation level as discussed above. This determines the relationship between SLEDAI and AI at the same study point. This relationship will be fit with an equation allowing the prediction of the SLEDAI score given an AI score (or vice versa). If AI predicts flares then changes in SLEDAI at some study point 1 will be preceded by changes in AI at point 0. Therefore, if a flare occurs between point 0 and 1, the AI score at point 0 (to be called AImeas) will be higher than what is expected (to be called AIexp) given the SLEDAI at study point 0. On the other hand with no change in disease activity between the study point 0 and study point 1, the AI score at point 0 will be very similar to what is expected given the SLEDAI at study point 0. The relative AI change (Rel-AI-diff) can be computed by dividing the difference of AImeas and AIexp by AImeas. The sensitivity and specificity of AI in predicting a significant change in SLEDAI 3 months later can be evaluated by using different thresholds of Rel-AI-diff. The thresholds can be bidirectional so if the Rel-AI-diff at a specific study point is higher than a specific threshold a flare is predicted, and similarly if it is lower than the negative of the specific threshold a significant reduction in SLEDAI is expected. On the other hand when the Rel-AI-diff at a study point is between the threshold and its negative, no significant changes in disease activity is expected. A ROC curve showing the trade of sensitivity and false positives can be generated using many different thresholds of Rel-AI-diff. Similar ROC curves can be generated using standard clinical measures including SLEDAI, anti-ds DNA and C3 levels.

If the fluctuation of AI varies at different SLEDAI values, the above analysis will be refined. A section above described the computation of AI-RSDall and AI-RSDpt-med and mentioned evaluating whether they change at different SLEDAI values. If they do then the ROC analysis can be done as described above but instead of using different thresholds of Rel-AI-diff, different thresholds of AI-RSDall and AI-RSDpt-med will be used. The performance obtained by the test with that of standard clinical measures including SLEDAI, anti-ds DNA and C3 levels will be compared.

In the above analysis, attempts are made to predict the SLEDAI at point 1 from the AI score at point 0. It is likely that in addition to the absolute level at point 0, the change of AI from point −1 to 0 will be informative in predicting SLEDAI at point 1. For example consider a patient who has at study point −1 an AI score of X−1, and at point 0 the AI score is increased to a new value X0 that is appreciably higher than X−1. This patient may have higher likelihood of a flare at point 1 than a patient whose AI has been stable at X0 at study points −1 and 0. This concept of AI change or velocity will be incorporated to generate a Modified AI (MAI) score. To generate a MAI at point 0 the AI score at point −1 and at point 0 will be needed, and hence one data point per patient will not have an MAI associated with it. The specific formula to incorporate the velocity into AI calculation to obtain MAI will be optimized. This optimization may be done through maximization of the correlation of MM and SLEDAI three months later. The cross validation design will be used to evaluate and control the degree of overfitting. Correlation can be done for data points of all samples, but also can be done at a patient level and the median correlation among all patients can be assessed. The latter approach ameliorates the issue of some patients having a systematic bias of too low or too high AI score. Using MM, the same type of ROC analysis that was mentioned for AI can be performed to assess its ability to predict SLEDAI 3 months later. First, analogously to what is described for AI, an analysis can be done to show the ability of MM at point 0 to distinguish PC and GC states at point 1. Additionally, an analysis similar to what was described for AI to assess the ability of MM at point 0 can be performed to predict significant disease activity change (3 points change on SLEDAI) between points 0 and 1. For this latter analysis different thresholds of Rel-AI-diff, AI-RSDall or AI-RSDpt-med can be used. The performance of MAI will be compared with that of AI to determine whether the addition of the velocity factor is useful.

One complication of the described study is that treatment changes are done for different patient during the follow up period of the study. This is likely to complicate the prediction of disease activity. For example, consider two patients with the same AI score at point 0 and one of those patients had a reduction in medication at the same time. The likelihood of this patient to have a rise in disease activity at point 1 is then likely to be higher than for the patient who did not change medications at point 0. This is likely to lead to underestimation of the performance of AI. One way to alleviate that is to eliminate all the points with significant medication changes from the study. Another is to modify the AI score to include whether a patient has a medication change and create a medication-modified AI. So in the example above with the two patients, the one with the medication change will have a higher medication-modified AI.

5. Integration with Other Predictive Markers

The predictive ability of the disease activity marker can be maximized. Therefore the predictive ability of the TCR/BCR repertoire information integrated with other markers will be tested. These markers include standard markers used in the clinic like anti-ds DNA and C3 levels. It will also include other markers that are published. For example a panel of chemokines has already been shown to have some predictive ability using the same set of patients as will be used. Whether this panel will increase the predictive ability of the TCR and BCR repertoire will be evaluated. The first step is to integrate the AI score with the additional measure to generate an Expanded AI (EAI) score. Different ways to do the integration can be assessed, and this can be optimized through maximization of the correlation of EAI and SLEDAI three months later. The cross validation design will be used to evaluate and control the degree of overfitting. Using EAI the ability to predict disease activity 3 months later will be assessed by its ability to distinguish GC from PC and to predict changes in disease activity. The performance in measuring disease activity and change in disease activity can be described through ROC analysis as described above.

6. Validation

The number of variables being tested is high compared with the number of samples. This can lend itself to overfitting, with initially promising results not being able to be validated in later studies. A cross validation approach will be used in the training to get a measure of the extent of overfitting. However, a validation on an independent set of samples will be involved in later work. This is not part of this proposal, but this marker can be clinically applicable. Using the data obtained above, it can be determined whether AI, MAI, or EAI, should be validated and the specific way to compute the measure of interest. One specific algorithm will be taken for validation. In addition one or more specific endpoints will be specified. The sensitivity and specificity of AI can be assessed in the ability to distinguish GC from PC 3 months later to evaluate the ability of AI to predict disease activity. In another example the sensitivity and specificity of AI to predict significant disease activity change in 3 month using a specific Rel-AI-diff threshold can be assessed.

Example 7

Measuring Response of an SLE Patient to Drug Therapy

The methods of the provided invention will be used to measure the response of an SLE patient to drug therapy. Determination of whether an SLE patient being given an expensive drug with serious side effects is responding to the drug plays a role in both patient care and also for making the administration of such care cost effective. Many clinical indicators of disease activity respond to treatment imprecisely and after a time lag of up to several months. During this time, disease may progress and side effects may add complications to therapy. A prompt understanding of the drug response would allow patients to be switched to more effective therapies more rapidly.

In this Example, a 35 year old African American female with a prior diagnosis of lupus presents to her regular rheumatologist. The patient's disease status is assessed on a quarterly basis through a comprehensive clinical assessment in addition to laboratory testing including measurement of C3, anti-ds DNA antibody levels, blood counts, and urinalysis. During one visit the patient complains of skin lesions and fatigue, and urinalysis shows evidence of proteinuria and/or cell casts. The rheumatologist refers the patient to a nephrologist for a kidney biopsy to assess inflammatory status of the kidney and orders serum creatinine and 24 hour urine protein to creatinine ratio to assess the degree of the impairment of the kidney function. A kidney biopsy shows evidence of diffuse lupus nephritis, while the urine protein to creatinine test reveals evidence of nephrotic syndrome (urine protein to creatinine ratio of 3.6). Based on this information a diagnosis of acute lupus nephritis is given and the patient is begun on a course of drug therapy. There are several possible drugs that can be chosen at this point. Immunomodulators such as mycophenolate mofetil (Cellcept) are often used although sometimes in severe cases drugs such as Methotrexate, Azathiopurine (Imuran) Cyclophosphamide (cytoxan), are prescribed. Rituximab (Rituxan) is also sometime used as a second or third choice. One of these drugs is often used in combination with a systemic steroid such as Prednisone or methylprednisolone in order to suppress the acute symptoms. Here, mycophenolate mofetil is prescribed at 150 mg per day alongside 60 mg of prednisone. Given the many side effects of steroids, including the risk of osteoporosis, hyperglycemia, weight gain, and other Cushingoid symptoms in the long term, the patient's prednisone dose is tapered over ~6 weeks if the clinical picture allows that.

The first question that is determined is whether the patient is responding to therapy, and as a result, can the dose of steroid can be appropriately decreased. Therefore, during this period the patient's serum creatinine as well as urine protein and creatinine are followed to ensure the patient is responding to the medications. Frequent kidney biopsy can be done to detect whether the inflammatory damage is being reversed; however, routine use of kidney biopsy carries too great a risk and is too invasive to be practical. Current blood based markers that are being used to assess inflammatory status are of limited use in making this decision in that they are not sufficiently well correlated with underlying disease to be relied upon to risk the increased side effects that accompany high doses of steroids. Serum and urine function markers may have some delay in detecting improvement in inflammatory status and hence steroids may be tapered before these markers show a definitive change and hence extending the period of the renal flare. A slower taper, informed by more sensitive markers, in these cases could have shortened the flare period preventing further damage to kidney tissue. After the reduction of steroid to a maintenance dose of approximately 10 mg the patient may show persistently elevated levels of protein in the urine and the high urine protein to creatinine ratio of 2, and the physician must now decide whether to switch from Cellcept to another medication. Arguing in favor of this is the continued evidence of loss of kidney function but without an accurate measure of inflammatory kidney status, it can be difficult to know whether the disease itself is in remission having nevertheless done some level of irreversible kidney damage that is resulting in these persistent levels of proteinuria. Here again the existing blood based markers are imperfectly informative and a further kidney biopsies are not practical. This decision would be greatly aided by an accurate blood based measure of disease status.

AutoImm Load would be very helpful in this situation to assess the response to therapy by measuring disease activity either alone or in combination with other markers of disease activity. An algorithm for AutoImm Load will be developed using the study described above. The correlating clonotypes that will be used to calculate AutoImm Load will be measured using a calibration test. This calibration test will be done using blood from a patient at a time of peak disease activity, for example at the start of therapy. The calibration test will be performed using blood or alternatively using the tissue that is affected (e.g. kidney biopsy or skin biopsy). At a later time at which the response to therapy is to be assessed, a blood sample will be taken and used along with the calibration test to measure AutoImm Load. This will be used to make a treatment decision. If the correlating clonotypes are derived from a populations study, there is no need for the calibration test and a blood test at the time at which the response to therapy is to be assessed is sufficient to measure AutoImm Load in order to inform the treatment decision.

Example 8

Determination of Appropriate Time to Taper or Stop Therapy for an SLE Patient

The methods of the provided invention can be used to determine the appropriate time to taper or stop therapy for an SLE patient. In addition to the time lag that can be exhibited by the clinical measures of disease activity, a further difficulty lies in the lack of sensitivity of these measurements. Subclinical disease can nonetheless result in a re-flaring of the disease if therapy is tapered too early. As a result of this, courses of immunosuppressant therapy are typically administered for a time period that is much longer than is necessary for the average patient to ensure that the risk of re-flaring is low for the average patient yet may still be long enough for the tail end of distribution. Therefore significant over-treatment, causing side effects and costs are occurring in most patients, while under-treatment of some patients occurs causing potentially preventable re-flares. A method that could measure subclinical activity that was predictive of the risk of re-flaring would allow therapy to be tapered based on such measures instead of relying on overtreatment by design.

In this example, the patient from Example 7 is on prednisone and mycophenolate mofetil for a period of 6 months and urine protein to creatinine ratio returns to a level of 0.5. This level remains above the baseline level expected in healthy individuals but it is not clear that this level is not due to some kidney damage that is not reversible. Other clinical measures of inflammation are normal and the patient does not report any other symptoms. At the same time the patient is experiencing moderate levels of nausea and weight gain as possible side effects to the medications that additionally have serious long term side effects. The doctor is faced with a difficult decision: balancing the fear of tapering the Cellcept and/or steroid too quickly, which could result in renewed kidney inflammation and likely further long term irreversible kidney damage and the adverse reactions that can occur due to the medications. Here again an unambiguous assessment of the disease status without having to perform a kidney biopsy would play a role in making this decision. Attempt of reducing steroids is recommended through repeated trials of steroids leading to the recurrence of the same clinical dilemma. In fact this question arises at every time the patient is in remission and the patient is on steroids or immunomodulators.

AutoImm Load would be very helpful in this situation to assess whether or not to taper therapy by measuring disease activity either alone or in combination with other markers of disease activity. An algorithm for AutoImm Load will be developed using the study described above. The correlating clonotypes that will be used to calculate AutoImm Load will be measured using a calibration test. This calibration test will be done using blood from a patient at a time of peak disease activity, for example at the start of therapy. The calibration test could be performed using blood or alternatively using the tissue that is affected (e.g. kidney biopsy or skin biopsy). At a later time at which the level of disease activity is to be assessed, a blood sample can be taken and used along with the calibration test to measure AutoImm Load. This will be used to make a treatment decision and to evaluate whether the patient has any detectable disease activity. If the correlating clonotypes are derived from a populations study, there is no need for the calibration test and a blood test at the time at which the response to therapy is to be assessed is sufficient to measure AutoImm Load in order to inform the treatment decision.

Example 9

Prediction of Flares in an SLE Patient

One challenge in treating SLE patients is that represented by the fact that flares arise without warning, thus thwarting the physicians' efforts to treat the disease preventively. Waiting for flares to occur before beginning treatment subjects patients to potentially destructive clinical symptoms, can involve expensive and inconvenient hospitalization, and may cause long term organ damage to be done while also necessitating aggressive therapeutic interventions that are themselves fraught with side effects. A much more desirable paradigm would be a therapeutic paradigm in which flares are detected at a subclinical phase at which time therapy could be administered proactively saving significant suffering to the patient, resulting in less expensive hospitalizations and ultimately enabling better long term prognosis for the patients.

The patient from Example 7 is recovering from the acute flare described above, and the patient is tapered off of all therapies except Plaquinil and a low dose of 5 mg of Prednisone. Nevertheless this patient remains at a high risk of having another inflammatory episode. As a result, this patient will remain in the care of a rheumatologist who will continue following patient's clinical symptoms and laboratory tests. Unfortunately these symptoms and tests do not provide early warning for an imminent flare until patients actually have exhibited clinical symptoms of a flare and the sequence repeats itself. A highly specific marker of increasing subclinical activity could be included in the routine clinical assessment of the patient in order to detect unambiguous signs of a flare which may reach a clinically detectable stage within the subsequent 1-3 months. Beginning therapies earlier might make the flare less severe and may allow treatment to be accomplished with less long term organ damage or less steroids used than what is currently the case.

AutoImm Load would be very helpful in this situation to assess the likelihood of an incipient flare by measuring disease activity either alone or in combination with other markers of disease activity. This score either by itself or the rate of increase (velocity) or acceleration of this score can be used to assess the likelihood of progression to a flare. An algorithm for AutoImm Load could be developed using the study described above. The correlating clonotypes that will be used to calculate AutoImm Load could be measured using a calibration test. This calibration test could be done using blood from a patient at a time of peak disease activity, for example at the start of therapy. The calibration test could be performed using blood or alternatively using the tissue that is affected (e.g. kidney biopsy or skin biopsy). At a later time at which the response to therapy is to be assessed, a blood sample can be taken and used along with the calibration test to measure AutoImm Load. This can be used to make a treatment decision. If the correlating clonotypes are derived from a populations study, there is no need for the calibration test and a blood test at the time at which the flare risk is to be assessed is sufficient to measure AutoImm Load in order to inform the treatment decision.

Example 10

Objective Measure to Assess Subjective Symptoms of SLE Patients

SLE affects many organs and produces many potential symptoms including ones that are very common in the healthy populations. For example, if an SLE patient complains of a headache, the headache may be a sign of CNS lupus or can be due to the common headache. Similarly, if SLE patients complain of worsening fatigue over a period of time, the worsening fatigue may be due to deterioration of their disease or can be due to depression or other causes. The availability of an objective measure that reflects disease activity can be of great help in the management of SLE patients.

The patient in Example 7 presents to the rheumatologist with chief complaints of headache, fatigue, and difficulty with concentration. Patient's headache is recurrent and only transiently gets better with Motrin treatment. The patient's SLE is otherwise in good control. Relevant psychosocial stressors in the patient's life include that she is going through divorce. Physicians are in a dilemma when they face SLE patients with symptoms that are non-specific to SLE and are common in the general population. Is the patient suffering from CNS lupus? Or could she suffering from other common causes of her symptoms, like depression? Current laboratory tests currently lack the sensitivity and specificity to be relied on to distinguish these possibilities. A reliable test to measure SLE disease activity can be utilized routinely to help in distinguishing the two possibilities.

AutoImm Load would be very helpful in this situation to objectively assess the disease activity either alone or in combination with other markers of disease activity. An algorithm for AutoImm Load will be developed using the study described above. The correlating clonotypes that will be used to calculate AutoImm Load will be measured using a calibration test. This calibration test will be done using blood from a patient at a time of peak disease activity, for example at the start of therapy. The calibration test will be performed using blood or alternatively using the tissue that is affected (e.g. kidney biopsy or skin biopsy). At a later time at which the objective disease activity is to be assessed, a blood sample can be taken and used along with the calibration test to measure AutoImm Load. This will be used to make a treatment decision. If the correlating clonotypes are derived from a populations study, there is no need for the calibration test and a blood test at the time at which the objective disease activity is to be assessed is sufficient to measure AutoImm Load in order to inform the treatment decision.

Example 11

Measuring Response to Drug Therapy of an MS Patient

As stated above, one of the principle challenges in MS therapy is measuring how well and whether a patient is responding to a drug therapy. During progressive and late stage disease there are clinical assessments such as the Expanded Disability Status Score (EDSS) which measure the degree of physical impairment that has resulted from the disease. However, these assessments are not useful in early stage or relapsing/remitting disease. Clinical parameters around relapses can be used to assess disease progression, but these are coarse and lagging indicators, as patients can go several years between relapses, during which little evidence can be gleaned from clinical assessments. Lastly, brain imaging such as gadolinium enhanced MRI can be used to examine brain lesions. MS patients are typically given such an MRI on a yearly basis. However, such images lack specificity. Furthermore, as a measure on integrated brain damage, they are not good measures of current disease activity but rather reflect the history of the disease and its impact on the brain.

While it is true that the current clinical treatment paradigm for MS is that patients diagnosed with relapsing remitting disease should be under continuous therapy in order to delay the onset of progressive disease, the increasing repertoire of approved drugs to treat MS makes the lack of biological feedback increasingly problematic. The list shown above of approved drugs to treat MS continues to get longer as the substantial investment in MS therapies begins to bear fruit. Each of these drugs has serious side effects and is very expensive to administer, with costs from $30,000-$100,000 per year of treatment. Patients that are not well managed will sooner transition to progressive disease which is debilitating and causes expensive health care interventions including hospitalizations and long term care. Hence, the patient can be allowed to receive optimal therapy early in treatment.

Clinical Utility Example

Patient profile: A 30 year old female comes to the hospital with monocular visual impairment with pain. She is given a neurological assessment and a lumbar puncture to obtain cerebral spinal fluid which is used to assess whether clonal T cells are present. She also is referred for a brain MRI. Based on these tests, a diagnosis of MS is made. She is prescribed Betaseron 250 mcg per injection to be self administered subcutaneously every other day. At a follow-up visit six months later, the patient is complaining of depression and weight gain. No further neurological events have been reported to the physician. The doctor is now faced with a clinical dilemma. Should the doctor maintain the therapy as it is been administered? Should a new therapy be used? Should the doctor order an MRI incurring cost and subjecting the patient to additional contrast exposure? Should the doctor wait until the next scheduled MRI shows new lesions? Should the doctor wait to see if flares recur? All of these decisions would benefit from an unambiguous measure of whether the disease is active or not.

AutoImm Load would be very helpful in this situation to assess the response to therapy by measuring disease activity either alone or in combination with other markers of disease activity. An algorithm for AutoImm Load will be developed using the studies described herein. The correlating clonotypes that will be used to calculate AutoImm Load will be measured using a calibration test. This calibration test will be done using blood from a patient at a time of peak disease activity, for example at the start of therapy. The calibration test could be performed using blood or alternatively using the tissue that is affected (e.g. CSF). At a later time at which the response to therapy is to be assessed, a blood sample can be taken and used along with the calibration test to measure AutoImm Load. This can be used to make a treatment decision. If the correlating clonotypes are derived from a population study, there is no need for the calibration test and a blood test at the time at which the response to therapy is to be assessed is sufficient to measure AutoImm Load in order to inform the treatment decision.

Example 12

Prediction of MS Flares

As in all autoimmune diseases, the amelioration of flares is a principle goal of therapy. Not only are flares debilitating for the patient and expensive to treat, but it is increasingly believed that each flare contributes to longer term non reversible disease progression. Several therapies can be used to control incipient flares such as IV methylprednisolone or oral prednisone. Such medications have significant side effects and as such are not prescribed without evidence of an active flare. A measure of increasing subclincal activity that was correlated with subsequent clinical flares could be used to inform this sort of proactive flare treatment which could result in shorter and less damaging flares. In addition there are therapies that demonstrate high clinical efficacy for reduction of flares that carry risks of very significant and lethal of side effects. One such drug is Tysabri, a drug that has been shown to result both in improved clinical outcomes and to increase the risk of deadly brain infections such as PML. These risks have reduced the value of such drugs to last line therapy when other drugs are proving to no longer control progression and limited the value of these drugs as chronic treatments. A test that could predict when the flare state is incipient could increase the utility of such drugs as they could be used in a manner similar to steroids to control acute flare periods while minimizing the risks of lethal side effects.

Clinical Utility Example

The patient from Example 11 is on Betaseron for 3 years and reports a clinical flare that lasts a week. The patient's MRI at the end of the year shows significant new lesions (multiple discrete variable sized ovoid perpendicularly directed T2W and FLAIR hyperintense lesions (plaques), appearing iso-hypointense on T1W images and hyperintense on T2W images involving bilateral periventricular and subcortical white matter regions, including the calloso-septal interface). The doctor is concerned that the patient is at high risk of flares over the course of the next 12 months. A clinical dilemma presents itself. Does the doctor wait for further clinical symptoms to intervene with additional therapy? Should the doctor switch therapies? If so, should another class of injectable be used such as copaxone or should a new class of therapy be used such as Tysabri? Should steroids be prescribed? A test that could monitor sub clinical disease activity and show when the disease is increasing and when a flare is likely to result could be used to help make these clinical decisions.

AutoImm Load would be very helpful in this situation to assess the risk of flare by measuring disease activity either alone or in combination with other markers of disease activity. An algorithm for AutoImm Load could be developed using the studies described in this invention. The correlating clonotypes that will be used to calculate AutoImm Load could be measured using a calibration test. This calibration test could be done using blood from a patient at a time of peak disease activity, for example at the start of therapy. The calibration test could be performed using blood or alternatively using the tissue that is affected (e.g. CSF). At a later time at which the risk of flare is to be assessed, a blood sample can be taken and used along with the calibration test to measure AutoImm Load. This can be used to make a treatment decision. If the correlating clonotypes are derived from a population study, there is no need for the calibration test and a blood test at the time at which the flare risk is to be assessed is sufficient to measure AutoImm Load in order to inform the treatment decision.

Example 13

Monitoring Therapy Compliance for MS

Because of the relative infrequency of clinical symptoms in the early stages of the disease, the interactions between a patient and his or her physician are not very frequent. At the same time, the therapies that are being prescribed are both expensive and inconvenient for the patient, involving self injections that can cause painful reaction and side effects. There is as a result a significant degree of non compliance with therapeutic regimes which are hard for a physician to monitor as the interactions between the patient and doctor is not routine. A test that could measure the state of the sub clinical disease would allow both doctor and patient to see on a routine basis how well controlled the underlying disease is. Such methods have proved very effective in HIV patients in motivating them to pursue therapy effectively. A test blood test that was performed quarterly would allow the physician to see the patient and measure the state of the disease.

AutoImm Load would be very helpful in this situation to assess the compliance with therapy by measuring disease activity either alone or in combination with other markers of disease activity. An algorithm for AutoImm Load will be developed using the studies described herein. The correlating clonotypes that will be used to calculate AutoImm Load will be measured using a calibration test. This calibration test will be done using blood from a patient at a time of peak disease activity, for example at the start of therapy. The calibration test could be performed using blood or alternatively using the tissue that is affected (e.g. CSF). At a later time at which the compliance with therapy is to be assessed, a blood sample will be taken and used along with the calibration test to measure AutoImm Load. This will be used to make a treatment decision and to better guide the patient toward better compliance. If the correlating clonotypes are derived from a population study, there is no need for the calibration test and a blood test at the time at which the compliance with therapy is to be assessed is sufficient to measure AutoImm Load in order to inform the treatment decision.

Example 14

Amplification of Mouse TCRβ and IgH Sequences

An amplification and sequencing scheme for mouse TCRβ and IgH will be developed that is similar to that developed for humans. Similar methods to minimize the differences in amplification efficiency of different sequences and similar validation techniques using spikes and the 5' RACE technique described above will be applied. The minimum input amount of cDNA will be determined in a similar methodology as described for human samples. One difference in the amplification scheme between mouse and humans is that the two C segments for TCRβ in mouse do not have any polymorphisms in the 50 bp closest to the J/C junction. Therefore, in the scheme the primer for the first stage amplification will be placed at positions 25-50 and for the second stage amplification the primer will be placed at positions 1-25, and the primer will have a 5' tail for the latter primer containing the P5 sequence. The different sequences will improve specificity and is similar to the strategy used in humans except there is no need to "loop out" any bases for polymorphisms.

Example 15

Primary Analysis of Mouse Sequence Data

The analysis framework that will be used for analysis of mouse data is similar to that described above for the human data. One difference is that the mouse samples will be sequenced to less depth than the human samples. It is anticipated that the blood samples from the mouse will be 100 μl. In 100 μl of blood there are ~100K lymphocytes and hence sequencing to a depth much higher than 100K does not significantly improve the precision. Therefore, only 100K reads for each mouse sample will be obtained. Even though the number of reads will be smaller for mouse than humans, a larger fraction of mouse total and blood lymphocytes will be sampled. The number of total mouse lymphocytes is expected to be more than 3 orders of magnitude smaller than that of humans. Similarly 100 μl of blood will provide a better sampling (~10%) of the lymphocytes in the mouse blood at the time when compared to sampling obtained using 10 ml of human blood (0.2%).

Example 16

IgH and TCR Repertoire Analysis in Mouse SLE Model

A mouse model of SLE will be used to study the relationship between TCR/BCR repertoire and disease activity. The mouse model will be the B6 with the sle1 and sle3 loci from NZM2410. These B6.sle1.sle3 (BSS) mice develop SLE-like nephritis in a spontaneous fashion. Three types of cohorts will be studied. For all study points, blood BUN, creatinine, and anti-nuclear autoantibodies, urine protein, and creatinine level will be obtained. It will be determined whether a score generated from blood TCR/BCR repertoire correlates well with these measured indices of kidney disease. The first cohort will be similar to the human cohort described where longitudinal blood samples will be collected along with kidney function assessment. Specifically, 7 BSS mice will be followed on a monthly basis till month 8. At the end, these mice will be sacrificed and in addition to blood, spleen and kidney tissue are analyzed. As a control, 5 B6 mice will be assessed in a similar manner. The second cohorts will be cross sectional where different cohorts of animals will be sacrificed at specific times and spleen, kidney, and blood samples will be analyzed at that time. Specifically, 5 BSS mice will be sacrificed each month and blood, spleen, and kidney will be analyzed. As a control, two B6 control mice will be assessed in the same fashion. Finally a third cohort will be treated with steroids after disease onset and nephritis assessment and blood samples obtained on a regular basis after that. Specifically at 4 months of age, 20 mice that have the disease will be treated with steroids and then on a biweekly basis for the next 4 months blood is taken for TCR/BCR repertoire analysis and kidney function assessment. As a control 5 BSS mice will be treated with placebo and followed in a similar fashion. TCR and BCR repertoire analysis will be performed from all the study points (i.e. different time points and different tissues for the same time point). The analysis will involve 2 stage PCR, sequencing processing, and primary data analysis as described above.

Example 17

Identification and Dynamics of Clonotypes that Correlate with Mouse SLE

First, a set of clonotypes that correlate with renal function will be identified. As a measure of renal function, urine protein/creatinine ratio, serum creatinine, or BUN levels can be used. In the first and third cohorts, the correlation of the blood level of each HPC clonotype with each of the three measures can be assessed. In a similar manner to what is described in humans, it can be assessed whether there is a great increase in the number of clonotypes with high correlation to 1, 2, or all 3 of the renal function measures over random expectation (or permutation testing). Given that random expectation, the correlation threshold will be picked where only 10% of the clonotypes with a correlation level above that threshold are expected to have the observed correlation level by chance (10% false discovery). These clonotypes will be focused on, and this set will be defined as "correlating clonotypes".

In addition to this statistical method to identify correlating clonotypes, clonotypes might be identified relevant to disease by a "functional" method of enrichment of specific clonotypes in kidney tissue. By the functional method a set of clonotypes may be identified in cohort 2 that may be relevant to disease, and these will be called functionally-identified correlating clonotypes. The extent of overlap between the "statistical" definition and the "functional" definition of correlating clonotypes can be assessed. Cohorts 1 and 3 have kidney samples collected at the last time point. It can be assessed whether clonotypes enriched in these kidney samples are present in the blood and are among the clonotypes with higher correlation with renal function.

The dynamics of correlating clonotypes (statistically and functionally identified) can then be evaluated. For example, using data from cohort 2, the time course of the rise and fall (if any) of their levels will be evaluated in the three compartments: kidney, blood, and spleen.

In the statistically identified correlating clonotypes, a subset of the correlating clonotypes would be identified by virtue of their correlation with renal function. The correlating clonotypes can be identified without knowing the renal function data. In other words, the characteristics that distinguish the correlating clonotypes from those that are irrelevant to disease can be understood. In order to do that a set of clonotypes with low correlation to renal function will be identified as control non correlating clonotypes.

Characteristics of Clonotypes that Correlate with Disease

After identification of the two sets of clonotypes, correlating and not correlating, characteristics that distinguish these two sets will be searched for. Separate and combined analysis using the correlating clonotypes identified statistically and functionally will be performed. The same type of characteristics studied in humans will be assessed, for example the level of the clonotype, the presence of particular sequence motifs, and the sequence of other related clonotypes. As described for the human study, there is a significant risk of overfilling and hence cross validation technique or separate training and testing sets need to be employed.

One utility for the mouse experiment is the availability of cells allowing for assessment of whether correlating clonotypes are enriched in a specific subtype of cells. It will be studied whether correlating clonotypes are enriched in some cell subtypes; sequencing from the full set of lymphocytes and from the specific subtype where correlating clonotypes are enriched can be done, and this criteria of enrichment can be used as an extra characteristic to distinguish correlating clonotypes from other disease-irrelevant clonotypes. In order to know what cell subtypes clonotypes are enriched a couple approaches will be taken: hypothesis driven and hypothesis free. The first is to try a dozen candidate surface markers on T or B cells in a set of samples. For example, one candidate is CD69 on T cells to select activated T cells. For B cells studies have shown the increase of $CD27^{high}$ cells in active SLE, and therefore that is a good candidate for a marker of cells that may have enrichment of the correlating clonotypes. In each of these experiments, the specific cell subtypes is purified through FACS. Then a sequencing reaction is done for cDNA from the full complement of the lymphocytes as well as for cDNA from the lymphocytes that were purified by FACS from a collection of different samples. It will be assessed whether the two sets of correlating and non correlating clonotypes are present in different proportions in the full complement of lymphocyte compared to the FACS purified subset. Markers that have a large difference can be useful in identifying correlating clonotypes. Enrichment of clonotypes in subtypes of cells with these markers will be used in addition to the sequence parameters to detect correlating clonotypes.

In the hypothesis free approach, markers will be searched for which are differentially expressed in cells with a correlating clonotype from other cells. A few cases will be chosen where a specific TCR clonotype is clearly correlating with disease, and cases will be picked where that clonotype is highly enriched that it represents the majority of the clonotypes with the same V segment. FACS will be done using antibody to the specific V segment (antibodies against all V segments are commercially available) to select a population that is highly enriched for cells carrying the correlating clonotype. The RNA can be prepared from these cells and the expression of all the genes can be studied by performing an array experiment. As a control, total RNA from lymphocytes can be used and/or RNA from FACS purified cells carrying another irrelevant V segment. Markers that maximally distinguish the sample obtained from the FACS purified V segment with the correlating clonotype from the controls can be searched for. Markers, including surface markers (since it is much easier to do FACS with surface proteins) that distinguish the two populations can be found. If a consistent RNA marker from samples of several mice is observed it will be validated at the protein level. Using the same samples, antibodies against the marker protein will be used in a FACS assay to purify cells carrying the marker protein. More than one marker may be tested to increase the chance of validating one of them. The TCR and/or BCR from the purified cells will be sequenced. If the RNA results hold at the protein level then the correlating clonotypes should be enriched in the purified subset of cells. After validating that RNA results still hold at the protein level, the results will be validated in other samples. Samples that were not subject to the array analysis will be subjected to FACS analysis using the antibody to the marker protein(s). The TCR and/or BCR of the purified cells will be sequenced. It will be evaluated whether the correlating clonotypes are enriched in the cells purified using antibody to the specific marker(s). This will validate the utility of the marker(s) in the identification of correlating clonotypes.

Example 18

Use of IgH and TCRβ Repertoire to Measure Disease Activity

The algorithm for correlating clonotypes from above can be applied to identify in all samples of cohorts 1 and 3 correlating clonotypes by virtue of their sequence and/or markers. Using the level of the correlating clonotypes in each patient, an AI score can be generated that correlates with a measure of renal function. As described above, there is an overfitting risk and the cross validation technique and/or separate training and testing set need to be employed. The correlation of AI and renal function measures can be evaluated in a cross sectional manner (all study points of all mice). The question of whether the AI score changes in an individual mouse can also be evaluated when renal function changes. This can be evaluated by comparing the AI from high and low renal function in the same animal in a similar manner to what is described in humans.

Example 19

Linking of Sequences from the Same Cell

Two sequences can be amplified from the same cell, and during amplification they can be linked to form one amplicon. Information on the presence of these two sequences in the same cell can then be preserved even if the linked sequences are mixed with a pool of sequences from other samples.

An example of the utility of this linking scheme is for assessment of the diversity of TCRs. The diversity of TCR is generated from the diversity of each of TCRα and TCRβ. In addition, the combination of a TCRα and TCRβ in a cell adds significantly to the diversity. However, when nucleic acids are extracted from a sample with a plurality of T-cells, the information of which TCRα is present in the same cell as TCRβ is lost. A method that allows the preservation of this information is presented here. This method comprises separating the cells in distinct compartments, amplifying the desired sequence in a way that covalently links initially separate amplicons, and optionally mixing all the amplified sequences for later analysis. Several methods can be conceived to place each cell in a compartment. For example, one method is to put cells in a microdroplet or a micelle emulsion that can be used in PCR. These droplets can be filled in a directed manner or randomly filled in such a way that most droplets contain at most a single cell. Also, cell sorting can be used to place a single cell in a PCR container. Amplification of nucleic acid can then be performed in each droplet.

Scheme 1

As illustrated in FIG. 9, sequence 1 can be amplified using primer 1 and primer 2. Primer 2 carries a 5' overhang sequence that is not complementary to the genomic sequence (FIG. 9A, thin line). Similarly sequence 2 can be amplified using primer 3 and primer 4 (FIG. 9A). Primer 3 carries a 5' overhang sequence that is complementary to the overhang sequence of primer 2 (FIG. 9A, line dashed line). In this figure the two overhangs (or the two linking sequences) representing two complementary sequences are drawn in thin lines; one sequence is shown as a solid line and its complement is shown as a dashed line. Other complementary sequences are drawn to have the same solid colors: black, and grey for sequence 1 and 2, respectively.

After amplification with primers 1-4, each of the two amplification products has a linking sequences on one end and the two products can anneal to each other and strands can be extended to form a full double stranded molecule (FIG. 9B). This molecule now has sequence 1 and 2 linked to each other and can then be amplified with primers 1 and 4 (FIG. 9C).

All 4 primers can be put in the reaction at the same time to achieve sequence linking and amplification. It may be beneficial to add low concentration of primers 2 and 3. The low concentration of primer 2 and 3 will ensure that the two individual sequence amplicons will reach saturation early in the reaction allowing the linked amplicon to dominate the PCR reaction in the latter stages of the reaction. This will lead to the final reaction having a high concentration of the linked amplicon relative to the individual sequence amplicons.

Scheme 1(a)

Scheme 1(a) is a variant of Scheme 1 in which the linking sequence is identical to the primer 2 sequence (FIG. 10). Sequence 1 can be amplified using primer 1 and primer 2 with no overhanging sequences on the primers (FIG. 10A). Primer 3 carries a 5' overhang sequence that is complementary to primer 2 (FIG. 10A). Sequence 2 can be amplified using primer 3 and primer 4 creating a linking sequence that is complementary to Sequence 1 (FIG. 10A). Other complementary sequences are drawn to have the same colors: black, and grey for sequence 1 and 2, respectively.

After amplification with primers 1-4, the two products can anneal to each other via the Primer 2 sequence and strands can be extended to form a full double stranded molecule (FIG. 10B). This molecule now has sequence 1 and 2 linked to each other and can then be amplified with primer 1 and 4 (FIG. 10C).

Scheme 2

Scheme 2, shown in FIG. 11 is a similar scheme to scheme 1 except that the ultimate amplification is achieved with sequences that are not complementary to the genome. One advantage of this approach is that the priming sequences can be chosen to be ideal for amplification with no off target amplification. This can be helpful in cases where primers complementary to the genomic sequence to be amplified are not ideal. By using primers not complementary to the genome for amplification, low concentration of primers 1-4 can be used, minimizing off target amplification. Also, scheme 2 can be adapted to a multiplexing scheme in which more than a pair of primers is used without causing as many primer interactions. Each pair of sequences to be linked will have its own unique 4 primers that need not be at high concentration. One pair of amplification primers can amplify all the pairs of linked sequences (FIG. 11C).

Sequence 1 can be amplified using primer 1 and primer 2 (FIG. 11A). Primer 1 and 2 carry on their 5' ends distinct overhang sequences that are not complementary to the genomic sequence (FIG. 11A, dotted and thin lines, respectively). Similarly, sequence 2 can be amplified using primer 3 and primer 4 (FIG. 11A). Primer 3 and 4 carry on their 5' ends distinct overhang sequences that are not complementary to the genomic sequence (FIG. 11A). The overhang on primers 1 and 4 are labeled as "Amp 1" (dotted) and "Amp 2" (wavy) and are sequences not complementary to the genome ultimately used for amplification (FIG. 11A). Analogously to scheme 1, the overhangs of primer 2 (thin) and 3 (thin/dashed) are the linking sequences that are complementary to each other. Other complementary sequences are drawn to have the same colors: black and gray for sequence 1 and sequence 2, respectively.

After amplification with primers 1-4, each of the two amplification products has a linking sequences on one end and the two products can anneal to each other and strands can be extended to form a full double stranded molecule (FIG. 11B). This molecule now has sequence 1 and 2 linked to each other and can then be amplified with primer 5 and 6 (FIG. 11C).

Optionally, primers 1-4 can initially be used, and after the linking of the two sequences, primer 5 and 6 can be added. A more preferred embodiment will have all the primers added in the first step. Yet a more preferred embodiment will have all the primers present initially with the concentration of primers 1-4 lower than that of 5 and 6. This allows the full linking and amplification to occur in one step. The low concentration of primers 2 and 3 will ensure that the two individual sequence amplicons will reach saturation early in the reaction allowing the linked amplicon to dominate the PCR in the latter stages of the reaction. This will lead to the final reaction having a high concentration of the linked amplicon relative to the individual sequence amplicons. Furthermore, the low concentration of primers 1-4 minimizes any off target amplification that can occur if these primers were lower quality than primers 5 and 6.

The use of primers 5 and 6 for amplification enables more efficient multiplexing (FIG. 12). One pair of primers (primers 5 and 6) can be used to amplify all the linked sequences. The linking sequences can be designed in different ways for different applications. The example illustrated in FIG. 12 is for two pairs of sequences to be linked, but this scheme can be extended further to 10's, 100's, or 1000's of sequences. If there is a set of gene pairs to be linked (e.g., TCRα with TCRβ and IgH with IgK) then the linking sequences for each pair can be different. In this example linking sequencing for TCRα and β will be different from those of IgH and IgK as depicted by thick dashed lines (TCRα and TCRβ or thin dashed lines (IgH with IgK) (FIG. 12A). All the amplified sequences in this example are shown in the same color. The amplification primers for the all the linked sequences will be the same primers: 5 and 6 as depicted in FIG. 11. In other applications the same linking sequences can be used if there is no specific pairing.

Figure 13A:
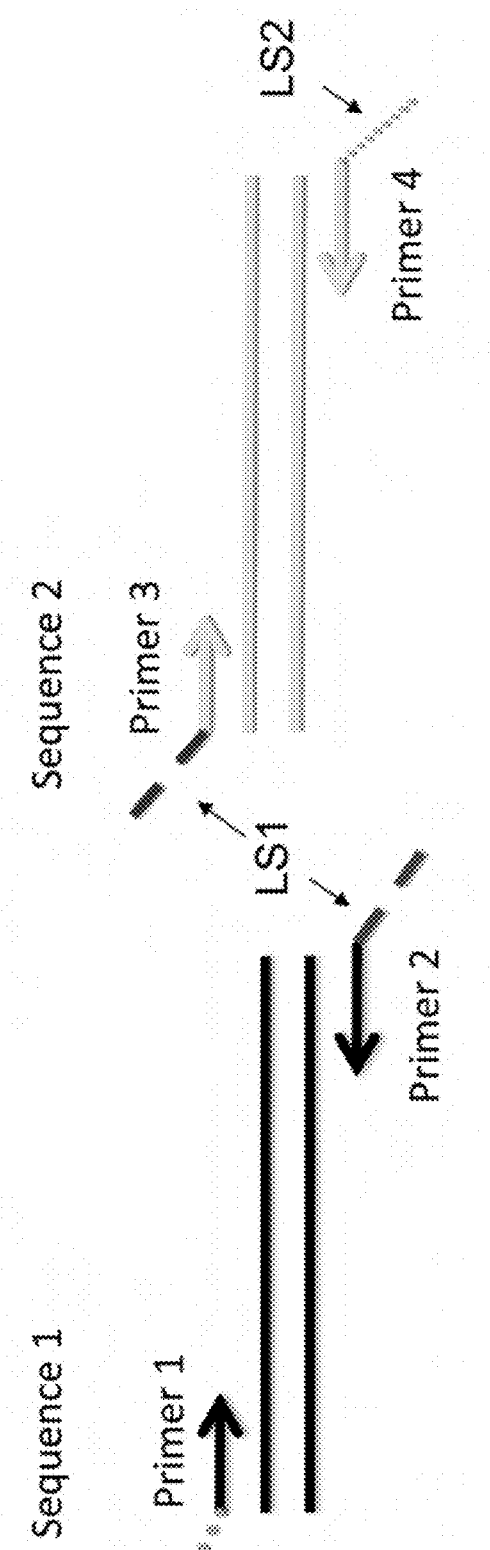
Figure 13D:
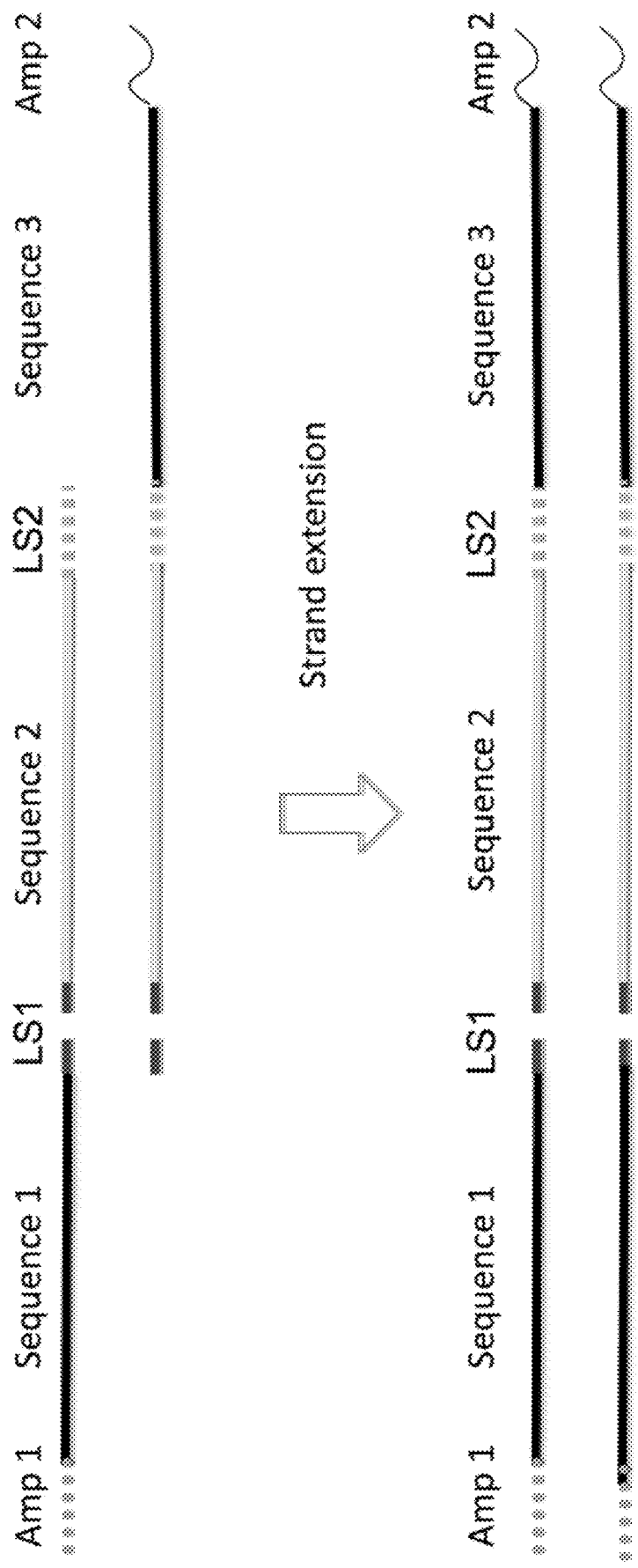

It is also conceived that more than 2 sequences can be linked. For example 3 or more sequences can be linked together (FIGS. 13A-13D). To create a molecule that links 3 sequences, one of the products can have two different linking sequences on its ends, each linking with one product (FIG. 13A). In the depicted example, sequence 2 has two linking sequences. The linking sequence of primer 3 allows the linking to sequence 1 through the linking sequence of primer 2 (linking sequence complementary pair LS1). Similarly, the linking sequence of primer 4 allows the linking to sequence 3 through the linking sequence of primer 5 (linking sequence complementary pair 2, LS2) (FIG. 13A). In another cycle the whole of sequence 2 becomes a linking sequence to link sequence 1 and sequence 3. The Amp1 and Amp 2 sequences complementary to primers 1 and 6 enable amplification after formation of a molecule with linked sequences 1-3.

Example 20

Monitoring for Metastatic Recurrence in Colon Cancer Patients

Many cancers that are detected at a treatable stage still carry an ongoing risk to the patient of metastatic tumor recurrence. Such recurrences are often detected late and at untreatable stages an can be fatal to the patients. One example of such a situation is that of recurrent colon cancer. Despite increasingly aggressive colon cancer screening programs, colon cancer represents one of the most common malignancies in the US. Approximately 150,000 patients per year are diagnosed with colon cancer at serious but treatable stages (Stage II and Stage III). These patients are treated by tumor resection followed by a course of chemotherapy. While these treatments are generally effective, there is nonetheless a significant chance that these patients will have metastatic recurrences of the primary tumor in the years following treatment. 50% of Stage III patients for instance will have a recurrence within 5 years of surgery. These recurrences can be either isolated (e.g. in the colon or liver) or multifocal. In either case but particularly if they are isolated, detecting them at an early stage can play a role in maximizing the chances of successful therapy (surgery and/or chemotherapy).

There are currently two tests used in post treatment surveillance. CT scan of the abdomen and chest is used to identify tumors visible on these images. Typically these scans are done at intervals of 6-12 months for the first 5 years post therapy. While these scans can reveal early stage malignancies, there clinical effectiveness is in debate. Drawbacks of these scans include the fact that they subject the patients to significant amounts of radiation which can itself cause further tumors and the significant expense. Another blood based test has been shown to have some value: CEA testing. This antibody test measures the level of a protein in serum that is specific to some colon tumors. The drawback to CEA testing is its lack of sensitivity (<60% of patients with positive CT scans have a positive CEA test).

In this embodiment of the invention, lymphocytes obtained from the resected primary tumor are used to develop an immune profile that can be used to add sensitivity to a blood based test for early cancer recurrence TCRs (and/or BCRs) of the lymphocytes found in the resected tumor can be amplified and sequenced. Clonotypes that are enriched in the tumor sample are likely relevant to the immune response to the tumor. Subsequent blood draws from the patient can be used to assess the level of these clonotypes. A rise in the level of these clonotypes can signal an immune response to a tumor recurrence. In this case the detection of the immune response may be more sensitive than the detection of the tumor marker itself.

Discovery Study for the Detection of Cancer Recurrence Using a Calibration Test

It is conceived that a discovery study can be performed to determine the likelihood of detection of recurrence given the profile of blood TCR (and/or BCR). Samples of resected tumor samples as well as follow up blood samples of patients with known outcome can be used for this study. TCR (and/or BCR) from all these samples can be sequenced. Candidates for the correlating clonotypes are those that are present in the TCR (and/or BCR) data from the tumor samples Given the known outcomes in this training study one can devise using the standard cross validation techniques, a model that generates a score (Recurrence Risk) given the level of the different clonotypes. This Recurrence score can thus be calculated in a new patient by measuring the clonotypes in the resected tumor (calibration point) and the data from the clonotypes found in the same patient's blood at a later time during the surveillance for recurrence. The use of the tumor data allows great reduction in the number of clonotypes present in blood that are considered in this analysis.

Discovery Study for the Detection of Cancer Recurrence Using a Calibration Test and a Population Study It is likely that not all clonotypes that are enriched in the tumor specimen are relevant to the immune response to the tumor. There might be some lymphocyte that expanded locally due to a favorable inflammatory condition. In another embodiment of this invention the discovery study can be done using the same samples but the study is used to identify parameters that distinguish "correlating" from "non correlating" clonotypes. These parameters can include 1) Sequence motif: The motif can be a specific V or J region, a combination VJ, or short sequences in DJ region that is associated with a clonotype being correlating; 2) Size of the clonotype; 3) Level: Absolute level (number of reads per million) or rank level; 4) Similarity to other clonotypes: the presence of other highly related clonotypes, like those with silent changes (nucleotide differences that code for same amino acids) or those with conservative amino acid changes; 5) For the BCRs the level of somatic mutations in the clonotype and/or the number of distinct clonotypes that differ by somatic mutations from some germline clonotype. 6) Presence in a cell carrying a specific marker. This study will then result in an algorithm that can predict which clonotypes are likely to be correlating with cancer recurrence in blood given a specific set of clonotypes present in a given tumor sample. These clonotypes can then be used to develop a score of Recurrence Risk in the same manner as described above.

Discovery Study for the Detection of Cancer Recurrence Using a Population Study

In another embodiment of this invention, the clonotypes measured in the resected tumor are used to generate a model that predicts correlating clonotypes in as yet unseen samples. This model can also be used to generate a Recurrence Risk score in a manner analogous to that described above. In this model there would be no need to measure the clonotypes in the resected cancer tissue in a new patient undergoing recurrence surveillance but rather the Recurrence Risk could be assessed by simply measuring the clonotypes in a given blood sample.

Discovery Study for the Detection of Primary Colon Cancer Using a Population Study As an extension it is conceived that detection of primary cancers can be achieved using the same methodology. With the primary cancers there is no tumor resected that can be used to enrich for relevant clonotypes. However, even in the presence of tumor resection data it is conceived that additional sequence and other parameters need to be used to identify relevant clonotypes and ultimately generate a score for likelihood of cancer detection. Therefore by extension if the algorithm is predictive enough one is able to detect the cancer from blood (or other bodily fluid) without the data from the resected tumor. In this embodiment of the invention, a discovery study with blood samples from patients preceding their diagnosis of primary cancer need to be available. In an analogous fashion to the one described above, parameters (sequence and other) can be identified to predict the clonotypes that are correlated to the immune system response to the tumor. A model can then be used to generate a Cancer Risk score that predicts the progression risk to colon cancer. This algorithm can then be applied to new patient's blood sample to measure the risk of primary colon cancer.

Example 21

Monitoring for Rejection in Heart Transplant Patients

Heart transplants are a relatively uncommon procedure as the supply of organs is very limited. 3,500 heart transplants performed every year worldwide. Each procedure is very expensive and the organs that are used are priceless. As a result the patients that receive these organs are treated extremely proactively. In order to measure the state of the immune reaction to the donated organ at a time at which interventions with immunosuppressants can be effective, patients are given periodic heart biopsies to measure inflammation of the organ. Based on these tests, aggressive courses of immunosuppressants may be given. These procedures have several limitations. As invasive surgical procedures they have risks to the patient. Furthermore they are expensive and can only be done at infrequent intervals. A blood based tests based on profiling the expression of a panel of 11 test genes (Allomap) have been shown to be quite sensitive in detecting organ rejection but lacks sufficient sensitivity to be used as a replacement for biopsy and is instead used to decide when to do a biopsy. In one embodiment of this invention TCR (and/or BCR) profiles are used to assess the state of "rejection" and generate a Rejection Risk score that predicts the likelihood of rejection in a specific time frame. It is conceived that a discovery study can be performed to determine the likelihood of rejection given the profile of blood TCR (and/or BCR). This can be used in the clinic to inform the immunosuppressive therapies that are being used.

Discovery of Correlating Clonotypes Using a Population Study

In this embodiment of the invention a population of post transplant patients with blood samples with known clinical outcome can be used. TCR (and/or BCR) from all these samples can be sequenced and correlation of individual clonotypes with rejection outcome can be used to distinguish correlating from non-correlating clonotypes. Subsequently, parameters can be derived that distinguish those two classes of clonotypes. These parameters can include 1) Sequence motif: The motif can be a specific V or J region, a combination VJ, or short sequences in DJ region that is associated with a clonotype being correlating; 2) Size of the clonotype; 3) Level: Absolute level (number of reads per million) or rank level; 4) Similarity to other clonotypes: the presence of other highly related clonotypes, like those with silent changes (nucleotide differences that code for same amino acids) or those with conservative amino acid changes; 5) For the BCRs the level of somatic mutations in the clonotype and/or the number of distinct clonotypes that differ by somatic mutations from some germline clonotype. 6) Presence in a cell carrying a specific marker. An alternative or supplemental method to define the correlating and non-correlating clonotype would come if the study samples have biopsy samples of the graft, particularly if it was in active rejection. It is expected that at that time there will be great enrichment of the correlating clonotypes. Parameters to distinguish these from the other clonotypes can be identified as discussed above.

The profile data from the blood samples is then used to predict the likelihood of rejection. Given the known outcomes in this training study one can devise, a model using the standard cross validation techniques that generates a Rejection Risk score given the level of the different clonotypes. Given the profile in a new blood sample of TCR (and/or BCR) at a specific point a Rejection Risk score relating to the likelihood of rejection can be generated Discovery of Correlating Clonotypes Using a Calibration Test In another embodiment a method of identifying correlating clonotypes can be implemented using a calibration test for each patient. This method involves a first biopsy sample be taken post transplant. The presence of biopsy material of the graft post transplant offers the possibility of analyzing TCRs from the biopsy sample to identify the correlating clonotypes as defined by those that are prevalent in this sample. This set of clonotypes can then be followed in blood and a score is generated for the likelihood of rejection. The algorithm to generate the Rejection Risk score is derived through a discovery study that is similar to the one described above that utilizes the available clinical data and the levels of the correlating clonotypes to generate a Rejection Risk score that approximates the likelihood of rejection.

In this embodiment a specific calibration test will be done using material from a first biopsy post transplant but further biopsies could be replaced by the use of blood samples whose clonotypes could be used along with this calibration test to measure a Rejection Risk score.

In addition to the graft biopsy, one can use the blood samples before transplant as another calibration point. Clonotypes that are prevalent in this sample are unlikely to be related to the rejection representing rather the history of prior antigens the patient has seen. Therefore when considering the blood samples after transplant one can subtract the clonotypes that were present before the transplant in determining the correlating clonotypes. These clonotypes can then be used to generate a model of Rejection Risk.

In this embodiment, two calibration tests would be can be used: one prior to transplant and one from a biopsy after transplant. These calibrations could then be used along with clonotypes derived from a blood test to measure Rejection Risk.

Discovery of Correlating Clonotypes Using a Calibration Test and a Population Study In another embodiment, the identification of the correlating clonotypes can be achieved through a combination of the above approaches. Specifically this can be achieved by using the population study to generate an algorithm to predict correlating clonotypes. In addition it can be achieved through calibration data from the same patient using graft biopsy and/or blood samples pre-transplant. A more preferred embodiment will employ both approaches: population-built algorithm and individual calibration to most accurately identify the correlating clonotypes. A Rejection Risk score is then generated using the level of these clonotypes to predict the likelihood of rejection through the use of the population study as a training set.

In this embodiment, two calibration tests can be used: one prior to transplant and one from a biopsy after transplant. These calibrations could then be used along with clonotypes derived from a blood test to measure Rejection Risk.

The prediction of GVHD can be done in a very similar manner with the same concept of the population study to generate an algorithm to predict correlating clonotypes. Also the "negative" calibration can be generated from the donor sample pre-transplantation. An approach using both the algorithm and calibration is likely to be more predictive of the correlating clonotypes. An algorithm to compute a score of the likelihood of GVHD given the level of the correlating clonotypes can be generated using a population study in a manner as described above. This algorithm can then be used for the prediction of the likelihood of GVHD in the next set of patients.

Example 22

Monitoring for PML Infection in MS Patients Treated with Natalizumab

One embodiment of the invention uses TCR and/or BCR profile to detect subclinical Progressive Multifocal Leukoencephalopathy (PML) in MS patients. PML is a serious and often fatal disease that causes often rapidly progressive demyelinating disease through killing oligodendrocytes that synthesize myelin. It is caused by JC virus that is present in a latent phase in the majority of the population. In a fraction of the immunosuppressed population (e.g., AIDS) the virus is reactivated leading to the development of this serious disease. In addition some patients who are being immunosuppressed through the use of medication like post transplant patients can also develop PML. Some specific medication has been linked to the risk of PML in specific patient populations. For example natalizumab (Tysabri) was associated with the development of more than 10 cases of PML among patients with multiple sclerosis (MS) leading to its withdrawal of the market for a period of time. Natalizumab is well accepted to be more effective than the other FDA approved medications for multiple sclerosis, but its use has been limited by the fear of PML development. Once PML is suspected, plasmapheresis can be performed to reduce the concentration of the drug in the patient. The overlap between symptoms of MS and PML can sometimes delay the detection of PML. Early detection of subclinical PML is urgently needed.

These clonotypes may be discerned from blood samples from a population where some patients developed PML. This population can be used to identify clonotypes that correlate with the later development of PML. With the availability of these clonotypes an algorithm to identify parameters that distinguish these from other clonotypes can be generated.

Discovery of Correlating Clonotypes Using a Population Study

In this case an algorithm is generated to predict the clonotypes that are relevant to the emergence of PML. The algorithm can be trained on a set of clonotypes deemed to be correlating with the disease. In this embodiment of the invention blood (or other body fluid) samples in a discovery study from a population of patients with a latent infection with JC virus some of whom go on to develop PML can be used. TCR (and/or BCR) from all these samples can be sequenced and correlation of individual clonotypes with infectious agent reactivation outcome can be used to distinguish correlating from non-correlating clonotypes. Parameters that distinguish those two classes of clonotypes can be identified. These parameters can include 1) Sequence motif: The motif can be a specific V or J region, a combination VJ, or short sequences in DJ region that is associated with a clonotype being correlating; 2) Size of the clonotype; 3) Level: Absolute level (number of reads per million) or rank level; 4) Similarity to other clonotypes: the presence of other highly related clonotypes, like those with silent changes (nucleotide differences that code for same amino acids) or those with conservative amino acid changes; 5) For the BCRs the level of somatic mutations in the clonotype and/or the number of distinct clonotypes that differ by somatic mutations from some germline clonotype. 6) Presence in a cell carrying a specific marker. An alternative or supplemental method to define the correlating and non-correlating clonotype would come from a set of patients who are mounting an immune response to the same infectious agent. Enriched clonotypes (particularly those that are at a significantly higher level than before the immune response) in these patients can be considered correlating and parameters that distinguish them from other clonotypes can be identified.

Similarly the correlating clonotypes can be identified from samples of patients with active PML or from in vitro studies to identify clonotypes that respond to JC virus antigen. The responding clonotypes may originate from one or a plurality of subjects that may be healthy or infected with the infectious agent. These clonotypes can be considered correlating and parameters that distinguish them from other clonotypes can be identified.

The profile data from the samples in the discovery study is then used to predict the likelihood of reactivation. Given the known outcomes in this training study one can devise using the standard cross validation techniques, a model that generates a PML Risk score given the level of the different clonotypes. So given the profile in a blood sample of TCR (and/or BCR) at a specific point a score relating to the likelihood of reactivation can be generated. This algorithm can now be used with data from a novel patient to predict the patient's correlating clonotypes as well as to generate a PML Risk score for the likelihood of reactivation.

In a very similar manner other infection-related outcomes can be studied. For example in addition to reactivation of latent infection, one can assess clearance of infection. Furthermore given the TCR and/or BCR repertoire one may be able to evaluate likelihood of having immunity for a specific infectious agent.

Example 23

Monitoring for Reactivation of Latent Infections

In another embodiment TCR and BCR profiling can be used to monitor infections that have periods of acute infection followed by latency and reactivation. Examples of such diseases include Hepatitis B and C as well as Herpes viruses. Predicting infections at early stage would be desirable.

Discovery of Correlating Clonotypes Using a Calibration Test

In another embodiment a method of identifying correlating clonotypes can be implemented using a calibration test for each patient. The presence of a biological sample from the same patient at a previous time point when the patient was mounting an immune response to the infectious agent can serve to identify the correlating clonotypes. This set of clonotypes can then be followed in blood and a Reactivation Risk score is generated for the likelihood of reactivation. The algorithm to generate the score is derived through a discovery study that is similar to the one described above that utilizes the available clinical data and the counts of the correlating clonotypes to generate a Reactivation Risk score that approximates the likelihood of reactivation. To use this score a sample taken from a new patient in clinical practice during a period of acute infection. This data would be used along with a subsequent sample taken during the latent period to measure the Reactivation Risk for clinical purposes.

Discovery of Correlating Clonotypes Using a Calibration Test and a Population Study In another embodiment, the identification of the correlating clonotypes can be achieved through a combination of the above approaches. Specifically this can be achieved by using the population study to generate an algorithm to predict correlating clonotypes. The correlating clonotypes can be obtained from a population study of patients with known outcome of the infection and/or a set of patients with active immune response to the infectious agent, and/or from in vitro experiments to identify clonotypes reactive with the infectious agent. In addition it can be achieved through calibration data from the same patient using older data points at the time of an active immune response against the relevant infectious agent. A more preferred embodiment will employ both approaches: population-built algorithm and individual calibration to most accurately identify the correlating clonotypes. A Reactivation Risk score is then generated using the level of these clonotypes to predict the likelihood of reactivation through the use of the population study as a training set. To use this score a sample taken from a new patient in the clinic during a period of acute infection is profiled. This data would be used along with a subsequent sample taken during the latent period to measure the Reactivation Risk for clinical purposes. A similar structure can be employed to study infectious agent clearance and or immunity to it.

Example 24

Monitoring for Allergic Response During Immunotherapy

Allergic rhinitis is a common condition afflicting ~11% of the US population. This is typically an allergy to pollen or dust. Eliminating the exposure is difficult and it involves vigilant effort. The most common treatments used in chronic rhinitis are decongestants, antihistamines, and nasal steroids. In severe cases immunotherapy is done. The goal of the immunotherapy is to de-sensitize the patient. First a challenge with many potential allergens is done to identify the specific allergen the patient is reacting to. Then the patient is injected with increasing amount of allergen over a period of months to years until a maintenance dose is achieved, and the treatment is then continued for several years. Typically the patient can feel an improvement in symptoms within 3-6 months, but that can also be as late as 12-18 months, but a large fraction of the patients do not benefit from the treatment or have relapses. One reason for the slow dose escalation is the risk of anaphylaxis if the patient is given a high dose of allergen before s/he sufficiently de-sensitized.

In one embodiment of this invention TCR (and/or BCR) profiles are used to assess the state of disease in allergic rhinitis and generate an Allergy Score that predicts how prone the patient to mount an allergic response should s/he be exposed to the relevant allergen. It is conceived that a discovery study can be performed to determine the likelihood of allergy response given the profile of blood TCR (and/or BCR). This can be used in tailoring the immunotherapy treatment. Possible clinical decision can be to discontinue the treatment if it is deemed ineffective, continue the injection regimen, or accelerate the treatment to reach the maintenance dose faster.

Discovery of Correlating Clonotypes Using a Population Study

In this embodiment of the invention a population of allergic rhinitis patients on immunotherapy with blood samples with known clinical outcome can be used. TCR (and/or BCR) from all these samples can be sequenced and correlation of individual clonotypes with allergy outcome can be used to distinguish correlating from non-correlating clonotypes. Subsequently, parameters can be derived that distinguish those two classes of clonotypes. These parameters can include 1) Sequence motif: The motif can be a specific V or J region, a combination VJ, or short sequences in DJ region that is associated with a clonotype being correlating; 2) Size of the clonotype; 3) Level: Absolute level (number of reads per million) or rank level; 4) Similarity to other clonotypes: the presence of other highly related clonotypes, like those with silent changes (nucleotide differences that code for same amino acids) or those with conservative amino acid changes; 5) For the BCRs the level of somatic mutations in the clonotype and/or the number of distinct clonotypes that differ by somatic mutations from some germline clonotype. 6) Presence in a cell carrying a specific marker. An alternative or supplemental method to define the correlating and non-correlating clonotype would use biopsy of positive allergy test material from patients positive for a specific allergen. At the site of injection of the allergen it is expected that there will be great enrichment of the correlating clonotypes. Parameters to distinguish these from the other clonotypes can be identified as discussed previously.

The profile data from the blood samples is then used to predict the allergy state. Given the known outcomes in this training study one can devise, a model using the standard cross validation techniques that generates an Allergy Score given the level of the different clonotypes. Given the profile in a new blood sample of TCR (and/or BCR) at a specific point, an Allergy Score can be generated to estimate the degree to which this patient is prone to mount an allergic response.

Discovery of Correlating Clonotypes Using a Calibration Test

In another embodiment a method of identifying correlating clonotypes can be implemented using a calibration test for each patient. This method involves a biopsy sample from a site with a positive allergen response be taken from the patient. This can be from the initial allergy test that was performed to determine the specific allergen the patient is responding to or sample from the site of any further treatment injections. This can be done more than once to ensure that the appropriate clonotypes are being followed in case there is some epitope spreading TCR and/or BCR from these biopsy samples can be used to identify the correlating clonotypes as defined by those that are prevalent in this sample. This set of clonotypes can then be followed in blood and a score is generated for the likelihood of allergy response. The algorithm to generate the Allergy Score is derived through a discovery study that is similar to the one described above that utilizes the available clinical data and the levels of the correlating clonotypes to generate an Allergy Score that estimates the allergy state.

Discovery of Correlating Clonotypes Using a Calibration Test and a Population Study In another embodiment, the identification of the correlating clonotypes can be achieved through a combination of the above approaches. Specifically this can be achieved by using the population study to generate an algorithm to predict correlating clonotypes. In addition it can be achieved through calibration data from the same patient using biopsy from a site with a positive allergen response. A more preferred embodiment will employ both approaches: population-built algorithm and individual calibration to most accurately identify the correlating clonotypes. An Allergy Score is then generated using the level of these clonotypes to predict the state of allergy through the use of the population study as a training set.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for monitoring an autoimmune disease, an infectious disease or a cancer of an individual by correlating clonotypes unique to the individual, the method comprising:
   (a) amplifying from a sample of nucleic acids from T cells and/or B cells and/or cell free DNA or RNA from the individual in a multiplex polymerase chain reaction (PCR) recombined nucleic acids comprising complementary determining region 3 (CDR3) sequences from T cell receptor genes or immunoglobulin genes;
   (b) spatially isolating individual molecules of the amplified recombined nucleic acids on a solid surface;
   (c) sequencing by synthesis using reversibly terminated labeled nucleotides die spatially isolated recombined nucleic acids to generate at least 10,000 sequence reads each having an error rate and at least 30 bp;
(d) combining the sequence reads into clonotypes of the recombined nucleic acids, wherein sequence reads are combined into different clonotypes whenever said sequence reads are distinct with a confidence of at least 99.9 percent based on error rates, frequencies and base divergences of the sequence reads;
(e) determining levels of clonotypes by counting sequence reads thereof; and
(f) monitoring the autoimmune disease, infectious disease or cancer from the levels of one or more correlating clonotypes of the autoimmune disease, infectious disease or cancer unique to the individual.

2. The method of claim 1 wherein said step of sequencing produces paired end reads and wherein said clonotypes are combined from the paired end reads.

3. The method of claim 1 wherein said step of sequencing includes re-amplifying said spatially isolated molecules of recombined nucleic acid.

4. The method of claim 1 wherein said step of sequencing comprises providing at least 100,000 sequence reads per run.

5. The method of claim 1 wherein said step of sequencing includes creating clusters of said spatially isolated recombined nucleic acids on said solid surface.

6. The method of claim 1 wherein said step of combining includes estimating a likelihood that a base of a sequence read is a sequencing error based on a quality score of the base.

7. The method of claim 1 wherein said sample comprises at least $10^5$ B-cells or at least $10^5$ T-cells and wherein said step of sequencing comprises at least $10^6$ reads per run.

8. A method for monitoring an autoimmune disease, an infectious disease or a cancer of an individual by correlating clonotypes unique to the individual, the method comprising:
(a) amplifying from a sample comprising T-cells and/or B-cells and/or cell-free DNA or RNA from the individual in a multiplex polymerase chain reaction (PCR) molecules of recombined nucleic acid comprising complementary determining region 3 (CDR3) sequences from T-cell receptor genes or immunoglobulin genes;
(b) spatially isolating individual molecules of the amplified recombined nucleic acids;
(c) sequencing by synthesis the spatially isolated recombined nucleic acids to provide sequence reads of CDR3 sequences, wherein each sequence read has an error rate and wherein said sequencing includes incorporating by a polymerase one or more nucleoside triphosphates at the end of a sequencing primer hybridized to said recombined nucleic acids and detection thereof by a change in current;
(d) combining the sequence reads into clonotypes of the recombined nucleic acids, wherein sequence reads are coalesced into different clonotypes whenever said sequence reads are distinct with a confidence of at least 99.9 percent based on error rates, frequencies and base divergences of the sequence reads;
(e) determining levels of clonotypes by counting sequence reads thereof; and
(f) monitoring said disease from the levels of one or more correlating clonotypes unique to the individual among the CDR3 sequences in the sample.

9. The method of claim 8 wherein said sample is blood.

10. The method of claim 8 wherein said step of sequencing provides at least 10,000 sequence reads and wherein said change in current is detected by a chemical-sensitive field effect transistor.

11. The method of claim 8 wherein said step of combining includes estimating a likelihood that a base of a sequence read is a sequencing error based on a quality score of the base.

12. The method of claim 8 wherein said sample comprises at least $10^5$ B-cells or at least $10^5$ T-cells and wherein said step of sequencing comprises at least $10^6$ sequence reads per run.

13. The method of claim 8 wherein said step of sequencing comprises generating at least 10,000 sequence reads per run and wherein said step of spatially isolating includes attaching said individual molecules of recombined nucleic acid to beads and transferring the beads to individual reaction chambers on a chemFET array.

14. The method of claim 8 wherein said step of spatially isolating includes dispersing said individual molecules into compartments of a water/oil emulsion to obtain one molecule in each compartment.

15. A method for monitoring an autoimmune disease, an infectious disease or a cancer of an individual by one or more correlating clonotypes unique to the individual, the method comprising:
(a) amplifying from a sample of nucleic acids from B-cells and/or cell free DNA or RNA from the individual in a multiplex polymerase chain reaction (PCR) recombined nucleic acids comprising complementary determining region 3 (CDR3) sequences from immunoglobulin genes, wherein each CDR3 sequence comprises a V segment;
(b) spatially isolating individual molecules of the amplified recombined nucleic acids on a solid surface;
(c) sequencing by synthesis using reversibly terminated labeled nucleotides the spatially isolated recombined nucleic acids to generate at least 10,000 sequence reads each having at least 30 bp and each having an error rate;
(d) combining the sequence reads of the recombined nucleic acids to identify clonotypes with V segments and somatic hypermutations therein with a confidence of at least 99.9 percent based on error rates, frequencies and base divergences of the sequence reads;
(e) determining levels of clonotypes by counting sequence reads thereof; and
(f) monitoring the autoimmune disease, infectious disease or cancer from the levels of one or more correlating clonotypes of the autoimmune disease, infectious disease or cancer unique to the individual.

16. The method of claim 15 wherein said CDR3 sequences are from said immunoglobulin genes and have a level of somatic mutations and wherein said correlating clonotypes of said autoimmune disease, infectious disease or cancer are distinguished among said CDR3 sequences by the level of somatic mutations in their clonotypes.

17. The method of claim 15 wherein said sequence reads are combined into different clonotypes whenever said sequence reads are distinct with a confidence of at least 99.9 percent.

18. The method of claim 15 wherein said step of sequencing produces paired end reads and wherein said clonotypes are combined from the paired end reads.

19. The method of claim 15 wherein said step of sequencing includes re-amplifying said spatially isolated molecules of recombined nucleic acid.

20. The method of claim 15 wherein said step of sequencing includes creating clusters of said spatially isolated recombined nucleic acids on said solid surface.

21. The method of claim 15 wherein said step of combining includes estimating a likelihood that a base of a sequence read is a sequencing error based on a quality score of the base.

22. The method of claim 15 wherein said step of monitoring includes determining said clonotypes correlated with said autoimmune disease, infectious disease or cancer with at least a frequency of 0.1 percent.

23. The method of claim 15 wherein said step of amplifying includes a multiplex PCR wherein each of said V segments has multiple primers.

* * * * *

SEQUENCE LISTING

```
<160> NUMBER OF SEQ ID NOS: 135

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aactatgttt tggtatcgtc agt                                           23

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttctggtacc gtcagcaac                                                19
```

```
<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agtgtatcct ggtaccaaca g                                             21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agtgtgtact ggtaccaaca g                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
actgtgtcct ggtaccaaca g                                             21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agtgtgtcct ggtaccaaca g                                             21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tctgtgtact ggtaccaaca g                                             21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccctttactg gtaccgacag                                               20
```

-continued

```
<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcctttactg gtaccgacag                                                    20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccctttactg gtaccgacaa a                                                  21

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttttggtacc aacaggtcc                                                     19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttttggtacc aacaggccc                                                     19

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aaccctttat tggtatcaac ag                                                 22

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgctatgtat tggtacaagc a                                                  21

<210> SEQ ID NO 15
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggcaatgtat tggtacaagc a                                             21

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tttctggtac agacagacca tga                                           23

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tactatgtat tggtataaac aggactc                                       27

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caaaatgtac tggtatcaac aa                                            22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atgttctggt atcgacaaga cc                                            22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atgtactggt atcgacaaga cc                                            22

<210> SEQ ID NO 21
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgccatgtac tggtatagac aag                                              23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atacttgtcc tggtatcgac aag                                              23

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atatgttctg gtatcgacaa ga                                               22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atatgtcctg gtatcgacaa ga                                               22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acatgtcctg gtatcgacaa ga                                               22

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
taatctttat tggtatcgac gtgt                                             24

<210> SEQ ID NO 27
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 27
gccatgtact ggtaccgaca                                           20

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tcatgtttac tggtatcggc ag                                        22

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
caacctatac tggtaccgac a                                         21

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
catgctaccc tttactggta cc                                        22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cacaataccc tttactggta cc                                        22

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
atacttctat tggtacagac aaatct                                    26

<210> SEQ ID NO 33
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 33
cactgtctac tggtaccagc a                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgtcatgtac tggtaccagc a                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aatgatacgg cgaccaccga g                                              21

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caagcagaag acggcatacg agat                                           24

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
agatcggaag agcacacgtc tgaactccag tcac                                34

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtgactggag ttcagacgtg tgctcttccg atct                                34

<210> SEQ ID NO 39
<211> LENGTH: 24
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 39
cctcagtgaa ggtctcctgc aagg                                            24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cctcggtgaa ggtctcctgc aagg                                            24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cctcagtgaa ggtttcctgc aagg                                            24

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gggctacagt gaaaatctcc tgcaagg                                         27

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aaacccacac agaccctcac gctgac                                          26

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aaacccacag agaccctcac gctgac                                          26

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
aaacccacac agaccctcac actgac                                          26

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46 ctgggggtc cctgagactc tcctg                                            25

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47 ctgggggtc ccttagactc tcctg                                            25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cagggcggtc cctgagactc tcctg                                           25

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cagggccgtc cctgagactc tcctg                                           25

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50 ctgggggtc cctgaaactc tcctg                                            25

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ctggcaggtc cctgagactc tcctg                                                25

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ctggagggtc cctgagactc tcctg                                                25

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctgggaggtc cctgagactc tcctg                                                25

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tgggggggcc ctgagactct cct                                                  23

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cttcggagac cctgtccctc acctg                                                25

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cttcggacac cctgtccctc acctg                                                25

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 57
cttcacagac cctgtccctc acctg                                            25

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cttcggagac cccgtccctc acctg                                            25

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cggggaccct gtccctcacc tg                                               22

<210> SEQ ID NO 60
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gatctcctgt aagggttctg gatacagct                                        29

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tcgcagaccc tctcactcac ctgtg                                            25

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tggatcaggc agtccccatc gagag                                            25

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
```
gctgggtgcg ccagatgccc                                                    20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tggatccgtc agcccccagg                                                    20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tggatccgtc agcccccggg                                                    20

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gtgcgacagg cccctggaca a                                                  21

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gggtgcgaca ggccactgga caa                                                23

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gtgcgccagg cccccggaca a                                                  21

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gggtgcgaca ggctcgtgga caa                                              23

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gggtgcaaca ggcccctgga aaa                                              23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gggtgcgaca ggctcctgga aaa                                              23

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gtgcgacagg cccccggaca a                                                21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gtgcgacagg cccccagaca a                                                21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tccgccagcc cccagggaag g                                                21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tccggcagcc cccagggaag g                                                21

```
<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tccggcagcc accagggaag g                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tccgccagca cccagggaag g                                              21

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tccggcagcc cgccgggaa                                                 19

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tccggcagcc gccggggaa                                                 19

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tccggcagcc cgctgggaag g                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tccgccagcc cctagggaag g                                              21
```

```
<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ggtccgccag gctccaggga a                                               21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gttccgccag gctccaggga a                                               21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ggtccgccag gcttccggga a                                               21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ggtccgtcaa gctccgggga a                                               21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gatccgccag gctccaggga a                                               21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ggtccgccaa gctccaggga a                                               21
```

```
<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ggtccgccag gctccaggca a                                          21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ggtccgccag gccccaggca a                                          21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ggtccgccag gctccgggca a                                          21

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gggtccgtca agctccaggg aagg                                       24

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ctgggtccgc caagctacag gaaa                                       24

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ggtccgccag cctccaggga a                                          21

<210> SEQ ID NO 94
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ggtccggcaa gctccaggga a                                              21

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ctaaaggctg aggacactgc cgtgt                                          25

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ctctgtgact cccgaggaca cggct                                          25

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
agtggagcag cctgaaggcc tc                                             22

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tgaccaacat ggaccctgtg gacac                                          25

<210> SEQ ID NO 99
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
acatggagct gagcagcctg agatc                                          25

<210> SEQ ID NO 100
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
acatggagct gagcaggctg agatc                                          25

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
acatggagct gaggagcctg agatc                                          25

<210> SEQ ID NO 102
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
acatggagct gaggagccta agatctga                                       28

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gagctctgtg accgccgcgg ac                                             22

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gagctctgtg accgccgtgg aca                                            23

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gagctctgtg accgctgcag acacg                                          25

<210> SEQ ID NO 106
<211> LENGTH: 23
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 106
gagctctgtg accgctgcgg aca                                             23

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gagctctgtg actgccgcag acacg                                           25

<210> SEQ ID NO 108
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gagctctgtg actgcagcag acacg                                           25

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gagctctgtg actgccgcgg aca                                             23

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gagctctgtg accgcggacg cg                                              22

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ggctctgtga ccgccgcgga c                                               21

<210> SEQ ID NO 112
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 112
gagctctgtg accgccgcag aca                                              23

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gagctctgtg accgctgaca cgg                                              23

<210> SEQ ID NO 114
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
caaatgaaca gcctgagagc cgaggaca                                         28

<210> SEQ ID NO 115
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
caaatgaaca gcctgaaaac cgaggaca                                         28

<210> SEQ ID NO 116
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
caaatgaaca gtctgaaaac cgaggaca                                         28

<210> SEQ ID NO 117
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
caaatgatca gcctgaaaac cgaggaca                                         28

<210> SEQ ID NO 118
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 118
caaatgaaca gtctgagaac tgaggacacc                                       30

<210> SEQ ID NO 119
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
caaatgaaca gtctgagagc cgaggaca                                         28

<210> SEQ ID NO 120
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
caaatgaaca gcctgagagc tgaggaca                                         28

<210> SEQ ID NO 121
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
caaatgagca gcctgagagc tgaggaca                                         28

<210> SEQ ID NO 122
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
caaatgaaca gcctgagaga cgaggaca                                         28

<210> SEQ ID NO 123
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
caaatgggca gcctgagagc tgaggaca                                         28

<210> SEQ ID NO 124
<211> LENGTH: 26
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 124
caaatgaaca gcctgagagc cgggga                                                    26

<210> SEQ ID NO 125
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
caaatgaaca gtctgagagc tgaggaca                                                  28

<210> SEQ ID NO 126
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
caaatgagca gtctgagagc tgaggaca                                                  28

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gccaggggga agaccgatgg                                                           20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
gccaggggga agacggatgg                                                           20

<210> SEQ ID NO 129
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
aatgatacgg cgaccaccga gatctgggaa gacgatgggc ccttggtgga                          50

<210> SEQ ID NO 130
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 130
aggacctgaa aaacgtgttc ccacccgagg t                              31

<210> SEQ ID NO 131
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
aggacctgaa caaggtgttc ccacccgagg t                              31

<210> SEQ ID NO 132
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cctccaccaa gggcccatcg gtcttccccc tggcgccctg ctccaggag            49

<210> SEQ ID NO 133
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
cttccaccaa gggcccatcc gtcttccccc tggcgccctg ctccaggag            49

<210> SEQ ID NO 134
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cttccaccaa gggcccatcg gtcttccccc tggcgccctg ctccaggag            49

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
agcgacctcg ggtgggaaca                                           20
```